US012569512B2

(12) United States Patent
Arnold et al.

(10) Patent No.: US 12,569,512 B2
(45) Date of Patent: Mar. 10, 2026

(54) HEPARAN SULFATE (HS) OLIGOSACCHARIDES EFFECT IN LIVER ISCHEMIA REPERFUSION INJURY

(71) Applicant: The University of North Carolina at Chapel Hill, Chapel Hill, NC (US)

(72) Inventors: Katelyn Arnold, Chapel Hill, NC (US); Jian Liu, Chapel Hill, NC (US); Rafal Pawlinski, Chapel Hill, NC (US); Brian Cooley, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 698 days.

(21) Appl. No.: 17/744,407

(22) Filed: May 13, 2022

(65) Prior Publication Data

US 2022/0265699 A1 Aug. 25, 2022

Related U.S. Application Data

(63) Continuation of application No. PCT/US2020/060581, filed on Nov. 13, 2020.

(60) Provisional application No. 62/934,845, filed on Nov. 13, 2019.

(51) Int. Cl.

| | |
|---|---|
| ***A61K 31/727*** | (2006.01) |
| ***A61P 1/16*** | (2006.01) |
| ***A61P 7/02*** | (2006.01) |

(52) U.S. Cl.

CPC .............. *A61K 31/727* (2013.01); *A61P 1/16* (2018.01); *A61P 7/02* (2018.01)

(58) Field of Classification Search

CPC ................................ A61K 31/727; A61P 1/16

See application file for complete search history.

(56) References Cited

U.S. PATENT DOCUMENTS

| | | | |
|---|---|---|---|
| 4,554,101 | A | 11/1985 | Hopp |
| 4,865,870 | A | 9/1989 | Hu et al. |
| 5,527,785 | A | 6/1996 | Bevilacqua et al. |
| 5,543,403 | A | 8/1996 | Petitou et al. |
| 5,817,487 | A | 10/1998 | Kobayashi et al. |
| 5,834,282 | A | 11/1998 | Habuchi et al. |
| 5,935,824 | A | 8/1999 | Sgariato |
| 6,255,088 | B1 | 7/2001 | Wong et al. |
| 6,608,044 | B1 | 8/2003 | Aderka et al. |
| 6,861,254 | B1 | 3/2005 | Rosenberg et al. |
| 6,977,248 | B1 | 12/2005 | Shukla et al. |
| 7,101,859 | B2 | 9/2006 | Yedgar et al. |
| 7,531,338 | B2 | 5/2009 | Liu |
| 9,951,149 | B2 | 4/2018 | Liu et al. |
| 10,286,047 | B2 | 5/2019 | Spirig et al. |
| 11,203,772 | B2 | 12/2021 | Xu et al. |
| 11,633,424 | B2 | 4/2023 | Liu et al. |
| 11,865,137 | B2 | 1/2024 | Arnold et al. |
| 11,903,963 | B2 | 2/2024 | Liu et al. |
| 11,993,627 | B2 | 5/2024 | Liu et al. |
| 2003/0083294 | A1 | 5/2003 | Sullenger |
| 2003/0099967 | A1 | 5/2003 | Deangelis |
| 2004/0087492 | A1 | 5/2004 | Yedgar et al. |
| 2004/0191870 | A1 | 9/2004 | Rosenberg et al. |
| 2004/0259142 | A1 | 12/2004 | Chai et al. |
| 2005/0090601 | A1 | 4/2005 | Dadalas et al. |
| 2005/0090661 | A1 | 4/2005 | Asari et al. |
| 2005/0101532 | A1 | 5/2005 | Yang et al. |
| 2005/0191288 | A1 | 9/2005 | Bennett et al. |
| 2005/0225562 | A1 | 10/2005 | Higgins et al. |
| 2005/0255562 | A1 | 11/2005 | Rosenberg et al. |
| 2005/0282775 | A1 | 12/2005 | Kennedy |
| 2006/0165673 | A1 | 7/2006 | Liu |
| 2006/0172931 | A1 | 8/2006 | San Antonio et al. |
| 2006/0229276 | A1 | 10/2006 | Hook et al. |
| 2008/0109236 | A1 | 5/2008 | DeAngelis |
| 2009/0035787 | A1 | 2/2009 | Lju |
| 2009/0155851 | A1 | 6/2009 | Sugiura et al. |
| 2009/0197308 | A1 | 8/2009 | Liu et al. |
| 2010/0125052 | A1 | 5/2010 | Lu et al. |
| 2010/0298260 | A1 | 11/2010 | Sundaram et al. |
| 2010/0305022 | A1 | 12/2010 | Shriver |
| 2011/0054236 | A1 | 3/2011 | Yang et al. |
| 2011/0281819 | A1 | 11/2011 | Kakehi et al. |
| 2012/0064044 | A1 | 3/2012 | Egan |

(Continued)

FOREIGN PATENT DOCUMENTS

| | | | |
|---|---|---|---|
| AU | 2003247808 | A1 | 1/2004 |
| CN | 103402526 | A | 11/2013 |

(Continued)

OTHER PUBLICATIONS

Cole, C. et al "Synthetic heparan sulfate oligosaccharides . . . " Plos One, vol. 5, iss 7, pp. 1-15. (Year: 2010).*

Arnold, Scientific reports, 2020, vol. 10(1), p. 17187, Oct. 14, 2020. (Year: 2020).*

Harada, Thromb Haemost 2007; 97: 81-87. (Year: 2007).*

Hagiwara, Critical Care 2008, 12:R43), abstract. (Year: 2008).*

Orgaran, Product Monograph—HIT for danaparoid sodium, Feb. 9, 2018. (Year: 2018).*

Advisory Action corresponding to U.S. Appl. No. 13/996,930 dated Dec. 9, 2016, 6 Pages.

(Continued)

*Primary Examiner* — Layla D Berry

(74) *Attorney, Agent, or Firm* — Jenkins, Taylor & Hunt, P.A.

(57) ABSTRACT

Disclosed is a method of treating liver ischemia reperfusion (I/R) injury in a subject. In some aspects, the method comprises providing a subject suffering from liver I/R injury or at risk of suffering liver I/R injury; and administering to the subject one or more heparan sulfate (HS) compounds. In some aspects, the one or more HS compounds comprises about 5 to about 18 saccharide units, optionally about 12 to about 18 saccharide units. In some aspects, the one or more HS compounds comprises about 12 saccharide units.

10 Claims, 18 Drawing Sheets

(56) References Cited

U.S. PATENT DOCUMENTS

| | | | |
|---|---|---|---|
| 2012/0308546 | A1 | 12/2012 | Kizhakkedathu et al. |
| 2012/0322114 | A1 | 12/2012 | Liu et al. |
| 2012/0322760 | A1 | 12/2012 | Fier et al. |
| 2013/0022647 | A1 | 1/2013 | Kizhakkedathu et al. |
| 2013/0296540 | A1 | 11/2013 | Xu et al. |
| 2013/0338097 | A1 | 12/2013 | Stephens et al. |
| 2016/0122446 | A1 | 5/2016 | Liu et al. |
| 2021/0137967 | A1 | 5/2021 | Liu et al. |
| 2021/0169923 | A1 | 6/2021 | Arnold et al. |
| 2021/0260098 | A1 | 8/2021 | Liu et al. |
| 2021/0332076 | A1 | 10/2021 | Liu et al. |
| 2022/0416486 | A1 | 12/2022 | Yamaguchi |
| 2024/0066048 | A1 | 2/2024 | Liu et al. |
| 2024/0216419 | A1 | 7/2024 | Arnold et al. |
| 2024/0309035 | A1 | 9/2024 | Liu et al. |

FOREIGN PATENT DOCUMENTS

| | | | | |
|---|---|---|---|---|
| CN | 111601603 | A | 8/2020 | |
| CN | 112437667 | A | 3/2021 | |
| CN | 105452479 | B | 5/2021 | |
| CN | 114980904 | A | 8/2022 | |
| EP | 0 394 971 | | 10/1990 | |
| EP | 0 565 863 | A | 10/1993 | |
| JP | 2002-534375 | A | 10/2002 | |
| JP | 2005-508827 | A | 4/2005 | |
| JP | 2011-168591 | A | 9/2011 | |
| JP | 2014-501730 | A | 1/2014 | |
| JP | 2016-523535 | A | 8/2016 | |
| JP | 2021502470 | A | 1/2021 | |
| JP | 2021528421 | A | 10/2021 | |
| JP | 2023501568 | A | 1/2023 | |
| JP | 2023-166387 | A | 11/2023 | |
| JP | 2024056723 | A | 4/2024 | |
| JP | 7495061 | B | 6/2024 | |
| JP | 753872482 | | 8/2024 | |
| WO | WO 89/04328 | | 5/1989 | |
| WO | WO 93/05167 | A1 | 3/1993 | |
| WO | WO 96/14425 | | 5/1996 | |
| WO | WO0151003 | A2 | 7/2001 | |
| WO | WO2003018598 | | 3/2003 | |
| WO | WO 2004/005475 | A2 | 1/2004 | |
| WO | WO2005/118609 | | 12/2005 | |
| WO | WO 2009/079693 | A1 | 7/2009 | |
| WO | WO 2012/088416 | A2 | 6/2012 | |
| WO | WO 2012/116048 | A1 | 8/2012 | |
| WO | WO 2014/204929 | A2 | 12/2014 | |
| WO | WO 2018/165656 | A1 | 9/2018 | |
| WO | WO 2019/010216 | A1 | 1/2019 | |
| WO | WO-2019090203 | A1 * | 5/2019 | ........... A61K 31/702 |
| WO | WO 2019/246264 | | 12/2019 | |

OTHER PUBLICATIONS

Aikawa, J.I., et al., "Molecular Cloning and Expression of a Third Member of the Heparan Sulfate/Heparin GlcNAc N-Deacetylase/N-Sulfotransferase Family," The Journal of Biological Chemistry, vol. 274, No. 5, 1999, pp. 2690-2695.

Aikawa, J.I., et al., "Multiple Isozymes of Heparan Sulfate/Heparin GlcNAc N-Deacetylase/GlcN N-Sulfotransferase," The Journal of Biological Chemistry, vol. 276, No. 8, pp. 5876-5882 (Feb. 23, 2001).

Antoine, D.J., et al., "Mechanistic Biomarkers Provide Early and Sensitive Detection of Acetaminophen-Induced Acute Liver Injury at First Presentation to Hospital," Hepatology vol. 58, pp. 777-787 (2013).

Applicant-Initiated Interview Summary corresponding to U.S. Appl. No. 13/996,930 dated Jan. 23, 2017.

Arnold, K., et al., "Design of Anti-Inflammatory Heparan Sulfate to Protect Against Acetaminophen-Induced Acute Liver Failure," Sci. Transl. Med., vol. 12, No. 535, pp. 1-26, Article ID eaav8075 (Mar. 18, 2020).

Arnold, K., et al., "Potential Use of Anti-Inflammatory Synthetic Heparan sulfate to attenuate liver damage," Biomedicines 2020 8(11), 503.

Arungundram, S., et al., "Modular Synthesis of Heparan Sulfate Oligosaccharides for Structure-Activity Relationship Studies," J. Am. Chem. Soc., vol. 131, pp. 17394-17405, Dec. 2, 2009.

Axelsson, J., et al., "Inactivation of Heparan Sulfate 2-O-Sulfotransferase Accentuates Neutrolphil Infiltration During Acute Inflammation in Mice," Blood, vol. 120, pp. 1742-1751 (2012).

Bailey, G.P., et al., "Delays During the Administration of Acetylcysteine for the Treatment of Paraacetamol Overdose," Br. J. Clin. Pharmacol. vol. 62, pp.

Baleux, F., et al., "A Synthetic CD4-Heparan Sulfate Glycoconjugate Inhibits CCR5 And CXCR4 HIV-1 Attachment and Entry," Nat. Chem. Biol., vol. 5, No. 10, pp. 743-748, Oct. 2009.

Beeson, J.G., et al., "Inhibition of Binding of Malaria-Infected Erythrocytes by a Tetradecasaccharide Fraction from Chondroitin Sulfate A," Infection and Immunity, vol. 66 No. 7 pp. 3397-3402 (Year: 1998).

Belot, F., et al., "Syntheses of Chondroitin 4- and 6-Sulfate Pentasaccharide Derivatives Having a Methyl Beta-D-Glucopyranosiduronic Acid at the Reducing End," Carbohyd. Res., vol. 326, pp. 88-97. (Year: 2000).

Bianchi, M.E., et al., "High-Mobility Group Box 1 Protein Orchestrates Responses to Tissue Damage via Inflammation, Innate and Adaptive Immunity, and Tissue Repair," Immunol. Rev. vol. 280, pp. 74-82 (2017).

Bitter T., et al., "A Modified Uronic Acid Carbazole Reaction," Anal. Biochem., vol. 4, pp. 330-334, 1962.

Blieden, M., et al., "A Perspective on the Epidemiology of Acetaminophen Exposure and Toxicity in the United States," Expert Rev. Clin. Pharmacol. vol. 7, pp. 341-348 (2014).

Bourgeaux, V., et al., "Two-Step Enzymatic Synthesis of UDP-N-Acetylgalactosamine," Bioorg. Med. Chem. Lett., vol. 15, pp. 5459-5462 (2005).

Bowman, K.G., et al., "Carbohydrate Sulfotransferases: Medliators of Extracellular Communication," Chemistry & Biology, vol. 6, pp. R9-R22 (Jan. 1999).

Bradbury, E.J., et al., "Chondroitinase ABC Promotes Functional Recovery After Spinal Cord Injury," Nature, vol. 416, pp. 636-640 (2002).

Brinkmann, V., et al., "Neutrophil Extracellular Traps Kill Bacteria," Science, vol. 303, pp. 1532-1535, 2004.

Broun, P., et al., "Catalytic plasticity of fatty acid modification enzymes underlying chemical diversity of plant lipids," Science, vol. 282, pp. 1315-1317 (1998).

Brown, J. M., et al., "A Sulfated Carbohydrate Epitope Inhibits Axon Regeneration After Injury," Proc. Natl. Acad. Sci. USA, vol. 109, pp. 4768-4773 (2012).

Brown, L., et al., "Cardenolide Analogues. 11. Improved Method for the Use of Fetizon's Reagent in the Synthesis of Cardiac Glycosides," Drug Research, vol. 31, No. 7, pp. 1059-1064 (1981).

Burkart, M. D., et al., "Regeneration of PAPS for the Enzymatic Synthesis of Sulfated Oligosaccharides," J. Org. Chem., vol. 65, pp. 5565-5574 (2000).

Cai. C., et al., "Towards the Chemoenzymatic Synthesis of Heparan Sulfate Oligosaccharides: Oxidative Cleavage of P-Nitrophenyl Group With Ceric Ammonium Salts," Tetra. Lett., vol. 54, No. 33, pp. 4471-4474 (2013).

Capila, I., et al., "Heparin—Protein Interactions," Angew. Chem. Int. Ed., vol. 41, pp. 390-412 (2002).

Carfi, A., et al., "Herpes Simplex Virus Glycoprotein D Bound to the Human Receptor HveA," Molecular Cell, vol. 8, pp. 169-179 (Jul. 2001).

Cassinelli, G., et al., "Old and New Applications of Non-Anticoagulant Heparin," International Journal of Cardiology, 212S1 pp. S14-S21 (2016).

Casu, B., et al., "Heparin-Like Compounds Prepared by Chemical Modification of Capsular Polysaccharide From *E. Coli* K5," Carbohydrate Research vol. 263, pp. 271-284 (1994).

Chan, S., et al., "Regulation of Pfemp1-VAR2CSA Translation by a Plasmodium Translation-Enhancing Factor," Nature Microbiology, vol. 2, Article No. 17068 (May 8, 2017).

(56) References Cited

OTHER PUBLICATIONS

Chen, G, Y., et al., "Sterile Inflammation: Sensing and Reacting to Damage," Nat. Immunol. vol. 10, pp. 826-837 (2010).
Chen, J., et al., "Using an Enzymatic Combinatorial Approach to Identify Anticoagulant Heparan Sulfate Structures," Chemistry and Biology, Current Biology, London, GB, vol. 14., No. 9, pp. 986-993 (Sep. 19, 2007).
Chen, M., et al., "Determination of the Substrate Specificities of N-Acetyl-D-glucosaminyltransferase," Biochemistry, vol. 45, pp. 12358-12365, 2006.
Chen, R., et al., "Release and Activity of Histone in Disease," Cell Death and Disease, vol. 5, No. 8, e1370, Aug. 14, 2014.
Chen., et al., Towards De Novo Synthesis of Structure-Defined Oligosaccharides with Heparan Sulfate Biosynthetic Enzymes, PhD dissertation. 1-167, (Date Created: Aug. 2008; Date Deposited: Oct. 11, 2010.).
Clark, S. R., et al., "Platelet TLR4 activates neutrophil extracellular traps to ensnare bacteria in septic blood," Nat Med., vol. 13, No. 4, pp. 463-469, 2007.
Communication of European publication number and information on the application of Article 67(3) EPC corresponding to European Application No. 14812890.3 dated Mar. 31, 2016.
Communication of European publication number corresponding to European Patent application No. 20887629.2 dated Jul. 20, 2022.
Communication of the extended European search report corresponding to European Application No. 14812890.3 dated Dec. 21, 2016.
Communication of the extended European Search report corresponding to European Patent Application No. 20887629.2 dated Oct. 27, 2023.
Communication pursuant to Article 94(3) EPC Corresponding to European Patent Application No. 19822610.2- 1109 dated Sep. 30, 2024, p. 5.
Communication under Rule 71(3) EPC (Intention to Grant) corresponding to European Patent Application No. 18873131.9-1109 dated Oct. 16, 2024, 7 Pages.
Conrad, H, E., "Heparin-Binding Proteins," J. of Medicinal Chemistry, vol. 42, No. 4, pp. 777-778 (1998).
Copeland, R., et al., "Using a 3-O-Sulfated Heparin Octasaccharide to Inhibit the Entry of Herpes Simplex Virus Type 1," Biochemistry, vol. 47, pp. 5774-5783 (2008).
Corrected Notice of Allowance corresponding to U.S. Appl. No. 16/492,858 dated Sep. 20, 2022.
Coutant. C., et al., "2-Deoxy-2-Trichloroacetamido-D-Glucopyranose Derivatives in Oligosaccharide Synthesis: From Hyaluronic Acid to Chondroitin 4-Sulfate Trisaccharides" J Chem Soc Perkin Trans 1, pp. 1573-1581 (Year: 1995).
Crowther, M. A., et al., "Mechanisms Responsible for the Failure of Protamine to Inactivate Low-Molecular-Weight Heparin," British Journal of Hematology, vol. 116, pp. 178-186 (2002).
Darden, T., et al., "Particle Mesh Ewald: an N.Log(N) Method for Ewald Sums in Large Systems," J. Chem. Phys. 1993, vol. 98, No. 12, pp. 10089-10092.
Das, S.K., et al., "Synthesis of Conformationally Locked I-Iduronic Acid Derivatives: Direct Evidence for a Critical Role of the Skew-Boat 280 Conformer in the Activation of Antithrombin by Heparin," Chem. Eur. J., vol. 7, No. 22, pp. 4821-4834 (2001).
Davenport, A., "Review Article: Low-Molecular-Weight Heparin as an Alternative Anticoagulant to Unfractionated Heparin for Routine Outpatient Haemodialysis Treatments," Nephrology, vol. 14, pp. 455-461 (2009).
Deagostini, A.I., et al., "Human Follicular Fluid Heparan Sulfate Contains Abundant 3-O-Sulfated Chains with Anticoagulant Activity," J. Biol. Chem., vol. 283, pp. 28115-28124, Oct. 17, 2008.
Decision to Grant corresponding to Japanese Patent Application No. 2016521505 dated Feb. 3, 2020.
Decision to Grant corresponding to Japanese Patent Application No. 2019549419 dated Jul. 11, 2023.
Dooley, T.P., "Cloning of the Human Phenol Sulfotransferase Gene Family: Three Genes Implicated in the Metabolism of Catecholamines, Thyroid Hormones and Drugs," Chemico-Biological Interactions, vol. 109, pp. 29-41 (1998).
Dou, W., et al., "Role of Deacetylase Activity of N-Deacetylase/N-Sulfotransferase 1 in Forming N-Sulfated Domain in Heparan Sulfate", The Journal of Biological Chemistry, vol. 290, No. 33, pp. 20427-20437 (Aug. 14, 2015).
Edens, R.E., et al., "Gradient Polyacrylamide Gel Electrophoresis for Determination of Molecular Weights of Heparin Preparations and Low-Molecular-Weight Heparin Derivatives," J. Pharm. Sci., vol. 81, No. 8, pp. 823-827 (Aug. 1992).
Eller, S., et al., "Automated Solid-Phase Synthesis of Chondroitin Sulfate Glycosaminoglycans," Angew. Chem. Int. Ed., vol. 52, pp. 5858-5861 (2013).
Esko, J,D., et al., "Molecular diversity of heparan sulfate," J. Clin. Invest., vol. 108, pp. 169-173 (2001).
European Search Report corresponding to European Patent Application No. 18764628.6 dated Dec. 2, 2020.
European Search Report corresponding to European Patent Application No. 18873131.9 dated Jul. 12, 2021.
Patent Certificate for European Patent No. 3691653 dated Mar. 12, 2025.
Extended European Search Report Corresponding to European Patent Application No. 19822610.2 dated Mar. 29, 2022.
Falany, C.N., "Introduction: Changing view of sulfation and the cytosolic Sulfotransferases," vol. 11, The FASEB Journal, pp. 1-2 (Jan. 1997).
Feltracco, P., et al., "Perioperative thrombotic complications in liver transplantation." World J. Gastroenterol., vol. 21, pp. 8004-8013 (2015).
Feng, S., et al., "Characteristics Associated with Liver Graft Failure: the Concept of a Donor Risk Index." Am. J. Transplant., vol. 6, pp. 783-790 (2006).
Feyerabend, T.B., et al., "Heparan sulfate C5-epimerase is essential for heparin biosynthesis in mast cells," Nat. Chem. Biol., vol. 2, No. 4, pp. 195-196 (Apr. 2006).
Fiser, A., et al., "Modeller: Generation and Refinement of Homology-Based Protein Structure Models," Methods Enzymol, vol. 374, pp. 461-491, 2003.
Frank, R.D., et al., "A non-anticoagulant synthetic pentasaccharide reduces inflammation in a murine model of kidney ischemia-reperfusion injury," Thromb Haemost, vol. 96, pp. 802-806. (Dec. 2006).
Freeman, C,G., et al., "The accumulation of circulating histones on heparan sulphate in the capillary glycocalyx of the lungs." Biomater., vol. 34, pp. 5670-5676 (2013).
Fried, M., et al., "Designing a VAR2CSA-based vaccine to prevent placental malaria." Vaccine, vol. 33, pp. 7483-7488 (2015).
Fukuta, M., et al., "Molecular cloning and expression of human chondroitin 6-sulfotransferase," Biochimica et Biophysica Acta, vol. 1399, pp. 57-61 (1998).
Fuster, J. J., et al., "The sweet and sour of cancer: glycans as novel therapeutic targets," Nat. Rev. Cancer, vol. 5, No. 7, pp. 1-27 (Jul. 2005).
Gama, C.I., et al., "Sulfation patterns of glycosaminoglycans encode molecular recognition and activity," Nat. Chem. Biol., vol. 2, No. 9, pp. 467-473 (Sep. 2006).
Ganey, P.E., et al. "Role of the Coagulation System in Acetaminophen-Induced Hepatotoxicity in Mice." Hepatology, vol. 46(4), pp. 1177-1186 (2007).
Goddard-Borger, E. D., et al., "An Efficient, Inexpensive and Shelf-Stable Diazotransfer Reagent: Imidazole-1-sulfonyl Azide Hydrochloride." Org. Lett., vol. 9, pp. 3797-3800 (2007).
Guerrini, M., et al., "An unusual antithrombin-binding heparin octasaccharide with an additional 3-O-sulfated glucosamine in the active pentasaccharide sequence," Biochem. J., vol. 449, pp. 343-351, 2013.
Guerrini, M., et al., "Antithrombin-binding oligosaccharides: structural diversities in a unique function?," Glycoconj. J., vol. 31, 409, pp. 9, Aug. 2014.

(56) References Cited

OTHER PUBLICATIONS

Guerrini, M., et al., "Oversulfated chondroitin sulfate is a contaminant in heparin associated with adverse clinical events," Nat. Biotechnol., vol. 26, No. 6, pp. 669-675 (Jun. 2008).
Habuchi, H., et al., "Molecular Characterization and Expression of Heparan-sulfate 6-Sulfotransferase—Complete cDNA Cloning in Human and Partial Cloning in Chinese Hamster Ovary Cells," The Journal of Biological Chemistry. vol. 273, No. 15, pp. 9208-9213 (Apr. 10, 1998).
Habuchi, O., et al., "Purification of Chondroitin 6-Sulfotransferase Secreted from Cultured Chick Embryo Chondrocytes," The Journal of Biological Chemistry, vol. 268(29), pp. 21968-21974 (1993).
Hajmohammadi, S., "Normal levels of anticoagulant heparan sulfate are not essential for normal hemostasis," The Journal of Clinical Investigation, vol. 111, pp. 989-999, No. 7, Apr. 2003.
Hansen, S.U., Tetrasaccharide iteration synthesis of a heparin-like dodecasaccharide and radiolaballing for in vivo tissue distribution studies, Nature Communications 4, Article No. 2016 (2013).
Harada, N., et al., "Dalteparin, a low molecular weight heparin, attenuates inflammatory responses and reduces ischemia-reperfusion-induced liver injury in rats." Crit. Care Med., vol. 34, Article No. 8, (2006).
Harris, E.N., et al., "Endocytic Function, Glycosaminoglycan Specificity, and Antibody Sensitivity of the Recombinant Human 190-kDa Hyaluronan Receptor for Endocytosis (HARE)," J. Biol. Chem., vol. 279, No. 35, pp. 36201-36209 (Aug. 27, 2004).
Heard, K.J., "Acetylcystein for acetaminophen poisoning," N. Eng. J. Med. vol. 359, pp. 285-292 (2008).
Hirsch, J., et al., "Beyond Unfractionated Heparin and Warfarin Current and Future Advances," Circulation, vol. 116, pp. 552-560 (2007).
Hirsch, J., et al., "Heparin and Low-Molecular-Weight Heparin the Seventh ACCP Conference on Antithrombotic and Thrombolytic Therapy," CHEST, vol. 126, pp. 188S-203S (2004).
Hsieh, P-H., Uncovering the Relationship between Sulphation Patterns and conformation of Iduronic Acid in Heparan Sulphate, Scientific Reports, Article No. 29602 (2016).
Hsieh, P-H., et al., "Chemoenzymatic synthesis and structural characterization of 2-O-sulfated glucuronic acid containing heparan sulfate hexasaccharides." Glycobiology vol. 24, pp. 681-692 (2014).
Hu, Y-P., et al.,"Synthesis of 3-O-sulfonated heparan sulfate octasaccharides that inhibit the herpes simplex virus type 1 host-cell interaction," Nat Chem, vol. 3, pp. 557-563, Jul. 2011.
Huang, C. C., et al., "Enhancing UCSF Chimera through web services," Nucleic Acids Res., vol. 42, pp. W478-W484, May 26, 2014.
Huebener, P., el al., "The HMGB1/RAGE axis triggers neutrophil-mediated injury amplification following necrosis." J. Clin. Invest., vol. 125, pp. 539-550 (2015).
Humphrey, W., "VMD: Visual Molecular Dynamics," J. Mol. Graph., vol. 14, pp. 33-38, 1996.
Iba et al., "Danaparoid sodium attenuates the increase in inflammatory cytokines and preserves organ function in endotoxemic rats," Critical Care, vol. 12, Article No. R86 (7 pages) (2008).
Iba, T., et al., "Advance in the management of sepsis-induced coagulopathy and disseminated intravascular coagulation." J. Clin. Med., vol. 8, Article No. 728 (16 pages) (2019).
Intention to Grant corresponding to European Patent Application No. 11849994.6 dated Apr. 7, 2021.
Intention to Grant corresponding to European Patent Application No. 11849994.6 dated Sep. 1, 2021.
Intention to Grant corresponding to European Patent Application No. 14812890.3 dated Oct. 27, 2021.
International Preliminary Report on Patentability corresponding to International Application No. PCT/US2018/040774 dated Jan. 7, 2020.
International Preliminary Report on Patentability corresponding to International Application No. PCT/US2019/037993 dated Dec. 22, 2020.
International Preliminary Report on Patentability Corresponding to International Patent Application No. PCT/US2020/060581 dated May 17, 2022.
International Preliminary Report on Patentability corresponding to International Application No. PCT/US2014/042683 dated Dec. 22, 2015.
International Preliminary Report on Patentability corresponding to International Application No. PCT/US2011/066843 dated Jun. 25, 2013.
International Preliminary Report on Patentability Corresponding to International application No. PCT/US2018/021986 dated Sep. 10, 2019.
International Preliminary Report on Patentability corresponding to international application No. PCT/US2018/059152 dated May 5, 2020.
International Search Report and the Written Opinion of the International Searching Authority Corresponding to International Application No. PCT/US2018/040774 dated Sep. 18, 2018.
International Search Report and the Written Opinion of the International Searching Authority corresponding to international application No. PCT/US2018/059152 dated Mar. 6, 2019.
International Search Report and Written Opinion of the International Searching Authority Corresponding to International Patent Application No. PCT/US2020/060581 dated Feb. 11, 2021.
International Search Report corresponding to International Application No. PCT/US2019/037993 dated Oct. 18, 2019.
International Search Report corresponding to International Application No. PCT/US2014/042683 dated Oct. 9, 2014.
International Search Report Corresponding to International application No. PCT/US 2018/021986 dated Aug. 1, 2018.
Jackson, S,P., et al., "Thromboinflammation: challenges of therapeutically targeting coagulation and other host defense mechanisms." Blood, vol. 133, pp. 906-918 (2019).
Jaeschke, H., et al., "Complement activates Kupffer cells and neutrophils during reperfusion after hepatic ischemia." Am. J. Physiol-Gastroint. Liver Physiol., vol. 264, pp. G801-G809 (1993).
Jaimes, F., et al., "Unfractioned heparin for treatment of sepsis: a randomized clinical trial (The HETRASE Study)." Crit. Care Med., vol. 37, pp. 1185-1196 (2009).
Jemth, P., et al., "Oligosaccharide library-based assessment of heparan sulfate 6-0-sulfotransferase substrate specificity," Journal of Biological Chemistry, vol. 278, No. 27, pp. 24371-24376 (Jul. 4, 2003).
Jin, L., et al., "The anticoagulant activation of antithrombin by heparin," Proc. Natl. Acad. Sci., vol. 94, pp. 14683-14688, Dec. 1997.
Kakkar, A, K., et al., "Low Molecular Weight Heparin, Therapy With Dalteparin, and Survival in Advanced Cancer: the Fragmin Advanced Malignancy Outcome Study (FAMOUS)," J. Clin. Oncol., vol. 22, No. 10, pp. 1944-1948 (May 15, 2004).
Kakuta, Y., et al., "Heparan sulphate N-sulphotransferase activity: reaction mechanism and substrate recognition," Biochem. Soc. Trans., vol. 31 (pt2), pp. 331-334 (2003).
Kamimura, K., et al., Regulation of Notch signaling by *Drosophila heparan*sulfate 3-O sulfotransferase, J Cell biol. Sep. 27, 2004: 166(7) :1069-79.
Kaneko, J., et al., "Coagulation and fibrinolytic profiles and appropriate use of heparin after living-donor liver transplantation." Clin. Transplant., vol. 19, pp. 804-809 (2005).
Kirschner, K. N., et al., "GLYCAM06: a Generalized Biomolecular Force Field. Carbohydrates," J. Comput. Chem., vol. 29, No. 4, pp. 622-655, Mar. 2008.
Kisselev, L., "Polypeptide release factors in prokaryotes and eukaryotes: same function, different structure," Structure, vol. 10, pp. 8-9 (2002).
Kollman, P., A., et al., "Calculating Structures and Free Energies of Complex Molecules: Combining Molecular Mechanics and Continuum Models," Acc. Chem. Res., vol. 33, pp. 889-897, 2000.
Konishi. T., et al., "Hepatic ischemia/reperfusion: mechanisms of tissue injury, repair, and regeneration." Gene Expr., vol. 17, pp. 277-287 (2017).

(56) References Cited

OTHER PUBLICATIONS

Kopec, A, K., et al., "Fibrin(ogen) drives repair after acetaminophen-induced liver injury via leukocyte aMb2 integrin-dependent upregulation of Mmp12." J. Hepatol., vol. 66, pp. 787-797 (2017).
Kreimann, M., et al., "Binding of anti-platelet factor 4/heparin antibodies depends on the thermodynamics of conformational changes in platelet factor 4," Blood, vol. 124, No. 15, pp. 2442-2449, Oct. 9, 2014.
Kreuger,J., et al., "Interactions between heparan sulfate and proteins: the concept of specificity," J. Cell Biol., vol. 174, No. 3, pp. 323-327 (Jul. 31, 2006).
Kuberan, B., et al., "Enzymatic synthesis of antithrombin III-binding heparan sulfate pentasaccharide," Nature Biotechnology, vol. 21, No. 11, 1343-1346 (Nov. 2003).
Kuberan, B., et al., The Journal of Biological Chemistry, "Chemoenzymatic Synthesis of Classic and Non-classical Anticoagulant Heparan Sulfate Polysaccharides", 2003, vol. 278, No. 52, pp. 52613-52621 (Year: 2003).
Kubes, et al., "Sterile inflammation in the liver." Gastroenterology, vol. 143, pp. 1158-1172 (2012).
Langdown, J.; Belzar, K. J.; Savory, W. J.; Baglin, T. P.; Huntington, J. A. J. Mo/. Biol. 2009, 386, 1278.
Laremore, T. et al "Ionic liquid matrix for direct UV-MALDI-TOF-MS Analysis of Dermatan Sulfate and Chondroitin Sulfate Oligosaccharides." Anal. Chem., vol. 79, pp. 1604-1610. (Year: 2007).
Laurent et al., "The Molecular-Weight-Dependence of the Anti-Coagulant Activity of Heparin," Biochem. J., vol. 175, pp. 691-701 (1978).
Ledin et al., "Heparan Sulfate Structure in Mice with Genetically Modified Heparan Sulfate Production," J. Biol. Chem., vol. 279, No. 41, pp. 42732-42741 (2004).
Lee, "Acetaminophen toxicity: changing perceptions on a social/medical issue." Hepatology, vol. 46, pp. 966-970 (2007).
Lee, M.K., and Lander, A.D., (1991) Proc. Natl. Acad. Sci. USA 88, 2768-2772.
Li et al., "Biosynthesis of Heparin/Heparan Sulfate cDNA Cloning and Expression of D-Glucuronyl C5-Epimerase From Bovine Lung," J. Biol. Chem., vol. 272, No. 4, pp. 28158-28163 (Oct. 31, 1997).
Li et al., "Enzymatic Synthesis of Homogeneous Chondroitin Sulfate Oligosaccharides." Angew. Chemie., vol. 129(39), pp. 11946-11949 (2017).
Li et al., "Enzymatic synthesis of homogenous chondroitin sulfate e oligosaccharides," Abstract of Glycobiol., vol. 28(12) (2018) [Abstract].
Li J. Su W, and Liu J. "Enzymatic synthesis of homogeneous chondroitin sulfate oligosaccharides." Angew Chem Int Ed. 2017; 56:11784-7.
Li, J., et al., "Enzymatic Synthesis of Chondroitin Sulfate E to Attenuate Bacteria Lipopolysaccharide-induced Organ Damage," ACS Central Science, vol. 6, No. 7, pp. 1199-1207, Jul. 1, 2020.
Li, L., et al., "Top-down approach for the direct characterization of low molecular weight heparins using LC-FT-MS," Anal. Chem., vol. 84, No. 20, pp. 8822-8829, Oct. 16, 2012.
Liliensiek et al., "Receptor for advanced glycation end products (RAGE) regulates sepsis but not the adaptive immune response." J. Clin. Invest. vol. 113, pp. 1641-1650 (2004).
Lindahl et al., "Regulated Diversity of Heparan Sulfate," The Journal of Biological Chemistry, vol. 273, No. 39, pp. 24979-24982 (Sep. 25, 1998).
Lindahl, U.; Backstrom, G.; Thunberg, L.; Leder, I. G. Proc. Natl. Acad. Sci. 1980, 77, 6551-6555.
Linhardt et al., "Production and Chemical Processing of Low Molecular Weight Heparins," Seminars in Thrombosis and Hemostasis, vol. 25, Suppl.3, pp. 5-16 (1999).
Liu et al., "Anticoagulant heparan sulfate: structural specificity and biosynthesis," Appl Microbiol Biotechnol., vol. 74, pp. 263-272 (2007).
Liu et al., "Cell Surface Heparan Sulfate and Its Roles in Assisting Viral Infections," Medicinal Research Reviews, vol. 22, No. 1, pp. 1-25 (2002).
Liu et al., "Characterization of a Heparan Sulfate Octasaccharide that Binds to Herpes Simplex Virus Type 1 Glycoprotein D," The Journal of Biological Chemistry, vol. 277, No. 36, pp. 33456-33467 (Sep. 6, 2002).
Liu et al., "Expression of Heparan Sulfate D-Glucosaminyl 3-O-Sulfotransferase Isoforms Reveals Novel Substrate Specificities," The Journal of Biological Chemistry, vol. 274, No. 8, pp. 5185-5192 (Feb. 19, 1999).
Liu et al., "Heparan Sulfate D-Glucosaminyl 3-O-Sulfotransferase-3A Sulfates N-Unsubstituted Glucosamine Residues," The Journal of Biological Chemistry vol. 274, No. 53, pp. 38155-38162 (Dec. 31, 1999).
Liu et al., "Purification of Heparan Sulfate D-Glucosaminyl 3-O-Sulfotransferase," The Journal of Biological Chemistry, vol. 271, No. 43, pp. 27072-27082 (Oct. 25, 1996).
Liu et al., Chemoenzymatic Design of Heparan Sulfate Oligosaccharides, J Biol Chem, vol. 285, No. 44, pp. 34240-34249 (Oct. 29, 2010).
Liu et al., "Enzymatic Placement of 6-O-Sulfo Groups in Heparan Sulfate," Biochemistry 2011, 50, 4382-4391.
Liu et al., "Lessons learned from the contamination of heparin," Nat. Prod. Rep., vol. 26, pp. 313-321 (2009).
Liu, J. et al., "Chemoenzymatic synthesis of heparan sulfate and heparin", Royal Society of Chemistry, vol. 31, pp. 1676-1685 (Year: 2014).
Loganathan et al., "Structural Variation in the Antithrombin III Binding Site Region and Its Occurrence in Heparin from Different Sources," Biochemistry, vol. 29, pp. 4362-4368 (1990).
Lopin et al., "From Polymer to Size-Defined Oligomers: an Expeditious Route for the Preparation of Chondroitin Oligosaccharides." Angew. Chem. Int. Ed., vol. 45, pp. 2574-2578 (2006).
Lopin-Bon et al., "Stereocontrolled preparation of biotinylated chondroitin sulfate E di-, tetra-, and hexasaccharide conjugates." Carbohydr. Res., vol. 402, pp. 35-43 (2015).
Lu et al., "Innate Immune Regulations and Liver Ischemia-Reperfusion Injury." Trasplantation, vol. 100, pp. 2601-2610 (2016).
Lundbäck et al., "A novel high mobility group box 1 neutralizing chimeric antibody attenuates drug-induced liver injury and postinjury inflammation in mice." Hepatology vol. 64, pp. 1699-1710 (2016).
Ly et al., "The proteoglycan bikunin has a defined sequence." Nat. Chem. Biol., vol. 7, pp. 827-833 (2011).
Macchione et al., "Synthesis of chondroitin sulfate oligosaccharides using N-tetrachlorophthaloyl and N-trifluoroacetyl galactosamine building blocks," European Journal of Organic Chemistry, pp. 3868-3884 (2014).
Mackman, "Triggers, targets and treatments for thrombosis," Nature, vol. 451, No. 21, pp. 914-918 (Feb. 21, 2008).
Mahe, I.; Chidac, J.; Helfer, H.; Nobel, S. J. Thromb. Haemost. 2016, 14, 2017.
Man et al., "Tolerance of the liver to intermittent pringle maneuver in hepatectomy for liver tumors." JAMA Sirgery, vol. 134, pp. 533-539 (1999).
Martinez-Gonzalez et al., "New Challenges for a Second-Generation Low-Molecular-Weight Heparin: Focus on Bemiparin," Expert Rev. Cardiovasc. Ther., vol. 8, No. 5, pp. 625-634 (2010).
Maza, S., et al., "Synthesis of chondroitin/dermatan sulfate-like oligosaccharides and evaluation of their protein affinity by fluorescence polarization." Org. Biomol. Chem., vol. 11, pp. 3510-3525 (2013).
Mazany et al., "Human chondroitin 6-sulfotransferase: cloning, gene structure, and chromosomal localization," Biochimica et Biophysica Acta, vol. 1407, pp. 92-97 (1998).
McGowan, K. E.; Makari, J.; Diamantouros, A.; Bucci, C.; Rempel, P.; Selby, R.; Geerts, W. Blood 2016, 127, 1954.
Miyachi et al., "Syntheses of chondroitin sulfate tetrasaccharide structures containing 4,6-disulfate patterns and analysis of their interaction with glycosaminoglycan-binding protein." Bioorg. Med. Chem. Lett., vol. 25, pp. 1552-1555 (2015).
Miyata et al., "Persistent cortical plasticity by upregulation of chondroitin 6-sulfation." Nat. Neurosci., vol. 15, pp. 414-422 (2012).
Mizumoto et al., "Molecular interactions between chondroitin-dermatan sulfate and growth factors/receptors/matrix proteins." Curr. Opin. Struct. Biol., vol. 34, pp. 35-42 (2015).

(56) References Cited

OTHER PUBLICATIONS

Monneau et al., "The sweet spot: how GAGs help chemokines guide migrating cells." J. Leukoc. Biol. vol. 99, pp. 935-953 (2016).
Moon et al., "Dissecting the substrate recognition of 3-O-suflotransferase for the biosynthesis of anticoagulant heparin," Proceedings of the National Academy of Sciences, vol. 109, No. 14, pp. 5265-5270 (2012).
Mossanen et al., "Acetaminophen-induced acute liver injury in mice." Lab. Anim. vol. 49, pp. 30-36 (2015).
Mousa, "Drug Discovery and Evaluation: Pharmacological Assays" (ed. Vogel, H.), 393-456 (Springer-Verlag Berlin, Heidelberg, New York (2008).
Mousa, "Heparin and Low-Molecular Weight Heparins in Thrombosis and Beyond," Meth. Mol. Biol., vol. 663, pp. 109-132 (2010).
Mousa, "In Vitro Methods of Evaluating Antithrombotics and Thrombolytics," Meth. Mol. Biol., vol. 663, pp. 1-28 (2010).
Munoz et al., "Enzymatic synthesis of heparin related polysaccharides on sensor chips: Rapid screening of heparin-protein interactions," Biochemical and Biophysical Research Communications, Academic Press Inc., Orlando, FL, US, vol. 339, No. 2, pp. 597-602 (Jan. 13, 2006).
Nadanaka et al., "Characteristic Hexasaccharide Sequences in Octasaccharides Derived from Shark Cartilage Chondroitin Sulfate D with a Neurite Outgrowth Promoting Activity," The Journal of Biological Chemistry, vol. 273(6), pp. 3296-3307 (1998).
Nagano et al., "Chondroitin sulfate protects vascular endothelial cells from toxicities of extracellular histones." Eur. J. Pharmacol., vol. 826, pp. 48-55 (2018).
Nam et al., "Syndecan-1 Limits the Progression of Liver Injury and Promotes Liver Repair in Acetaminophen-Induced Liver Injury in Mice." Hepatology, vol. 66(5), pp. 1601-1615, doi: 10.1002/hep.29265 (2017).
Nastuk et al., "Expression Cloning and Characterization of NSIST, a Novel Sulfotransferase Expressed by a Subset of Neurons and Postsynaptic Targets," The Journal of Neuroscience, vol. 18, No. 18, pp. 7167-7177 (Sep. 15, 1998).
Nelson, R.M., et al., "Heparin Oligosaccharides Bind L- and P-Selectin and Inhibit Acute Inflammation," Blood, vol. 82, No. 11, pp. 3253-3258, Dec. 1, 1993.
Noti et al., "Chemical Approaches to Define the Review Structure-Activity Relationship of Heparin-like Glycosaminoglycans," Chemistry & Biology, vol. 12, pp. 731-756 (Jul. 2005).
Notice of Allowance and Interview Summary corresponding to U.S. Appl. No. 14/898,865 dated Dec. 15, 2017.
Notice of Allowance and Interview Summary corresponding to U.S. Appl. No. 17/254,145 dated Jan. 30, 2023.
Notice of Allowance corresponding to U.S. Appl. No. 17/254,145 dated Dec. 8, 2022.
Notice of Allowance corresponding to U.S. Appl. No. 16/492,858 dated Sep. 12, 2022.
Notice of Allowance corresponding to U.S. Appl. No. 16/492,858 dated Feb. 10, 2023.
Notice of Allowance corresponding to U.S. Appl. No. 16/761,159 dated Aug. 24, 2023.
Notice of Allowance corresponding to U.S. Appl. No. 16/761,159 dated Dec. 4, 2023.
Notice of Allowance corresponding to U.S. Appl. No. 16/492,858 dated May 24, 2023.
Notice of Allowance corresponding to U.S. Appl. No. 16/492,858 dated Sep. 7, 2023.
Notice of Allowance corresponding to U.S. Appl. No. 16/492,858 dated Dec. 21, 2023.
Notice of Publication Corresponding to European Patent Application. No. 19822610.2 dated Mar. 31, 2021.
Notice of Publication Corresponding to European Patent application No. 18764628.6 dated Nov. 20, 2019.
Notice of Publication Corresponding to European Patent Application No. 18873131.9 dated Jul. 15, 2020.
Oduah et al., "Heparin: Past, present, and future." Pharmaceuticals (Basel), vol. 9, Article No. 38 (2016).
Office Action (Annex to the communication) corresponding to European Patent Application No. 18873131.9 dated Apr. 4, 2024, 7 Pages.
Office Action (Decision to grant) corresponding to European Patent Application No. 18873131.9 dated Feb. 13, 2025, 3 Pages.
Office Action (Decision of Rejection) corresponding to Chinese Patent Application No. 20180020095.X dated Dec. 1, 2022, p. 10 (Translation).
Office Action (Final) corresponding to U.S. Appl. No. 16/625,342 dated Nov. 4, 2022.
Office Action (Non- Final Rejection) corresponding to U.S. Appl. No. 18/138,596 dated Jun. 5, 2024.
Office Action (Non- Final Rejection) corresponding to U.S. Appl. No. 18/406,942 dated Aug. 12, 2024.
Office Action (Notice of Allowance) corresponding to U.S. Appl. No. 16/625,342 dated Jan. 10, 2024.
Office Action (Notice of Allowance) corresponding to U.S. Appl. No. 16/625,342 dated Jan. 19, 2024.
Office Action (Notice of Allowance) corresponding to U.S. Appl. No. 16/625,342 dated Apr. 26, 2024.
Office Action (Notice of Reasons for Rejection) corresponding to Japanese Patent Application No. 2020-570916 dated Jun. 20, 2023.
Office Action (Notice of Reasons for Rejection) corresponding to Japanese Patent Application No. 2020-570916 dated Jan. 16, 2024.
Office Action (Notice of Reasons for Rejection) corresponding to Japanese Patent Application No. 2023-129964 dated Oct. 8, 2024, 14 pages.
Office Action (Notice of Reasons for Rejection) corresponding to Japanese Patent Application No. 2022-527682 dated Oct. 29, 2024, p. 8.
Office Action (Restriction Requirement) corresponding to U.S. Appl. No. 16/625,342 dated Dec. 16, 2021.
Office Action (Restriction Requirement) corresponding to U.S. Appl. No. 17/254,145 dated Nov. 26, 2021.
Office Action (Restriction Requirement) corresponding to U.S. Appl. No. 16/761,159 dated Jun. 10, 2022.
Office Action (Restriction Requirement) corresponding to U.S. Appl. No. 16/492,858 dated Jun. 30, 2021.
Office Action (Restriction Requirement) corresponding to U.S. Appl. No. 18/222,910 dated Dec. 6, 2024, 9 Pages.
Office Action (Restriction Requirement) corresponding to U.S. Appl. No. 18/222,910 dated Feb. 26, 2025, 11 Pages.
Office Action corresponding to Chinese Application No. 202080092829.2 dated Jun. 21, 2023.
Office Action (Decision of Rejection) corresponding to Chinese Application No. 202080092829.2 dated Mar. 3, 2024, p. 19.
Office Action corresponding to Chinese Patent Application No. 201880020095.X dated Jun. 8, 2022.
Office Action corresponding to Chinese Patent Application No. 201480044429.9 dated Aug. 30, 2018, p. 43.
Office Action corresponding to Chinese Patent Application No. 201480044429.9 dated Apr. 9, 2019.
Office Action corresponding to Chinese Patent Application No. 201480044429.9 dated Mar. 3, 2020.
Office Action corresponding to Chinese Patent Application No. 201880020095.X dated Sep. 22, 2021.
Office Action corresponding to Chinese Patent Application No. 2018800850125 dated Jan. 20, 2023.
Office Action corresponding to Chinese Patent Application No. 201880020095.X dated Apr. 18, 2023.
Office Action corresponding to Chinese Patent Application No. 201980044697.3 dated Jul. 7, 2023.
Office Action corresponding to Chinese Patent Application No. 201880085012.5 dated Nov. 30, 2023.
Office Action corresponding to Chinese patent Application No. 202310342719.2 dated May 8, 2023.
Office Action corresponding to Chinese Patent Application No. 202080092 dated Jun. 21, 2023.
Office Action corresponding to Chinese patent Application No. 202310342719.2 dated Feb. 28, 2024.
Office Action corresponding to Chinese patent Application No. 202310342719.2 dated Jul. 24, 2024, 8 Pages.

(56) References Cited

OTHER PUBLICATIONS

Office Action corresponding to Chinese patent Application No. 202310342719.2 dated Oct. 16, 2024, p. 11.
Office Action corresponding to European Patent Application No. 11849994.6 dated May 24, 2018.
Office Action corresponding to European Patent Application No. 11849994.6 dated Jan. 22, 2020.
Office Action corresponding to European Patent Application No. 14812890.3 dated Jun. 23, 2020.
Office Action corresponding to European Patent Application No. 18873131.9-1112 dated Aug. 14, 2023.
Office Action corresponding to European Patent Application No. 18764628.6 dated Nov. 16, 2023.
Office Action corresponding to Japanese Patent Application No. 2019-549419 dated Dec. 23, 2022, p. 3.
Office Action corresponding to Japanese Patent Application No. 2016-521505 dated Jul. 19, 2018.
Office Action corresponding to Japanese Patent Application No. 2016-521505 dated Jun. 21, 2019.
Office Action corresponding to Japanese Patent Application No. 2019-549419 dated Mar. 22, 2022.
Office Action corresponding to Japanese Patent Application No. 2020-544568 dated Jan. 10, 2023.
Office Action corresponding to Japanese Patent Application No. 2024-008526 dated Dec. 24, 2024, p. 4.
Office Action Corresponding to Japanese Patent Application Serial No. 2020-544568 dated Sep. 26, 2023.
Office Action corresponding to U.S. Appl. No. 12/178,434 dated Oct. 28, 2011.
Office Action corresponding to U.S. Appl. No. 12/178,434 dated Apr. 19, 2011.
Office Action corresponding to U.S. Appl. No. 12/178,434 dated Jan. 26, 2011.
Office Action corresponding to U.S. Appl. No. 16/492,858 dated Jan. 13, 2022.
Office Action corresponding to U.S. Appl. No. 16/625,342 dated Mar. 21, 2022.
Office Action corresponding to U.S. Appl. No. 16/761,159 dated Jan. 11, 2023.
Office Action corresponding to U.S. Appl. No. 17/254,145 dated Feb. 16, 2022.
Office Action corresponding to U.S. Appl. No. 13/996,930 dated Oct. 8, 2015.
Office Action corresponding to U.S. Appl. No. 13/996,930 dated May 26, 2016.
Office Action corresponding to U.S. Appl. No. 13/996,930 dated Dec. 21, 2017.
Office Action corresponding to U.S. Appl. No. 13/996,930 dated Jul. 30, 2018.
Office Action corresponding to U.S. Appl. No. 13/996,930 dated Nov. 22, 2019.
Office Action corresponding to U.S. Appl. No. 16/625,342 dated Jun. 15, 2023.
Official Action corresponding to U.S. Appl. No. 14/898,865 dated Mar. 23, 2017.
Oliveira et al., "Neutrophils: a cornerstone of liver ischemia and reperfusion injury." Lab. Invest., vol. 96, pp. 51-62 (2018).
Ong et al., "Expression Cloning of a Human Sulfotransferase that Directs the Synthesis of the HNK-1 Glycan on the Neural Cell Adhesion Molecule and Glycolipids," The Journal of Biological Chemistry, vol. 273, No. 9, pp. 5190-5195 (Feb. 27, 1998).
Onufriev, A; Bashford, D.; Case, D. A Proteins 2004, 55, 383.
Ouyang et al., "Molecular Cloning and Expression of Human and Mouse Tyrosylprotein Sulfotransferase-2 and a Tyrosylprotein Sulfotransferase Homologue in Caenorhabditis elegans," The Journal of Biological Chemistry, vol. 273, No. 38, pp. 24770-24774 (Sep. 18, 1998).
Park et al., "Cell surface heparan sulfate proteoglycans: selective regulators of ligand-receptor encounters." J. Biol. Chem. vol. 275, pp. 29923-29926 (2000).
Patel, V. N.; Lombaert, I. M.A.; Cowherd, S. N.; Shworak, N.; Xu, Y.; Liu, J.; Hoffman, M. P. Developmental Cell 2014, 29, 662.
Pempe, et al., "Probing Structural Selectivity of Synthetic Heparin Binding to Stabilin Protein Receptors," Journal of Biol. Chem., vol. 287, No. 25, pp. 20774-20783 (Jun. 15, 2012).
Pettersen, E. F.; Goddard, T. D.; Huang, C. C.; Couch, G. S.; Greenblatt, D. M.; Meng. E. C.; Ferrin, T. E. J. Comp. Chem. 2004, 25, 1605.
Pierce et al., "Inflammatory response to trauma: implications for coagulation and resuscitation." Curr. Opin. Anesthesio., vol. 27, pp. 246-252 (2014).
Proudfoot et al., "Glycosaminoglycan binding and oligomerization are essential for the in vivo activity of certain chemokines." Proc. Natl. Acad. Sci. USA vol. 100, pp. 1885-1890 (2003).
Pulsipher et al., "Directing Neuronal Signaling through Cell-Surface Glycan Engineering." J. Am. Chem. Soc., vol. 136, pp. 6794-6797 (2014).
Raman, R.; Venkataraman, G.; Ernst, S.; Sasisekharan, R. Proc. Natl. Acad. Scl. 2003, 100, 2357.
Razi et al., "Structural and functional properties of heparin analogues obtained by chemical sulphation of *Escherichia coli* K5 capsular polysaccharide," Biochem. J., vol. 389, pp. 465-472 (1995).
Rejection decision corresponding to Chinese Patent Application No. 201880085012.5 dated Feb. 23, 2024.
Rohrmann et al., "Two N-acetylgalactosaminyltransferase are involved in the biosynthesis of chondroitin sulfate," European Journal of Biochemistry, vol. 148, pp. 463-469 (1985).
Roman-Blas et al., "The combined therapy with chondroitin sulfate plus glucosamine sulfate or chondroitin sulfate plus glucosamine hydrochloride does not improve joint damage in an experimental model of knee osteoarthritis in rabbits." Eur. J. Pharmacol., vol. 794, pp. 8-14 (2017).
Rosenberg et al., "Heparan Sulfate Proteoglycans of the Cardiovascular System Specific Structures Emerge But How Is Synthesis Regulated?" J. Clin. Invest., vol. 99, No. 9, pp. 2062-2070 (May 1997).
Saeki et al., "Molecular Cloning, Expression, and Characterization of a Novel Mouse Liver SULTIBI Sulfotransferase," J. Biochem., vol. 124, pp. 55-64 (1998).
Sala et al., "UDP-N-trifluoroacetylglucosamine as an alternative substrate in N-acetylglucosaminyltransferase reactions", Carbohydrate Research, vol. 306, pp. 127-136 (1998).
Sarris et al., "Inflammatory chemokines direct and restrict leukocyte migration within live tissues as glycan-bound gradients." Curr. Biol. vol. 22, pp. 2375-2382 (2012).
Sattelle, B. M., et al., "Free energy landscapes of iduronic acid and related monosaccharides," J Am Chem Soc, vol. 132, pp. 13132-13134, Sep. 29, 2010.
Sattelle, B. M.; Almond, A. Glycobiology 2011, 21, 1651.
Schroeder et al., "Protamine neutralization of low molecular weight heparins and their oligosaccharide components," Anal Bioanal Chem, vol. 399, pp. 763-771 (2011).
Schworer, R.; Zubkova, 0. V.; Turnbull, J. E.; Tyler, P. C. Chem. Eur. J. 2013, 19, 6817.
Sheng et al., "The Dominating Role of N-Deacetylase/N-Sulfotransferase 1 in Forming Domain Structures in Heparan Sulfate," The Journal of Biological Chemistry, vol. 286, No. 22, pp. 19768-19776 (Jun. 3, 2011).
Shiori et al., "Sequence determination of synthesized chondroitin sulfate dodecasaccharides." Glycobiology, vol. 26, pp. 592-606 (2016).
Shively et al., "Formation of Anhydrosugars in the Chemical Depolymerization of Heparin," Biochemistry, vol. 15, No. 18, pp. 3932-3942 (1976).
Shriver et al., "Glycomics: a Pathway to a Class of New and Improved Therapeutics," Nat. Rev. Drug Discov., vol. 3, pp. 863-873 (Oct. 2004).
Shriver, Z., et al., "Heparin and Heparan Sulfate: Analyzing Structure and Microheterogeneity," Handb Exp. Pharmacol, 207, pp. 159-176. (2012).
Shukla et al., "A Novel Role for 3-O-Sulfated Heparan Sulfate in Herpes Simplex Virus 1 Entry," Cell, vol. 99, pp. 13-22 (Oct. 1, 1999).

(56) References Cited

OTHER PUBLICATIONS

Shukla et al., "Herpesviruses and heparan sulfate: an intimate relationship in aid of viral entry," The Journal of Clinical Investigation, vol. 108, No. 4, pp. 503-510 (Aug. 2001).
Shworak et al., "Molecular Cloning and Expression of Mouse and Human cDNAs Encoding Heparan Sulfate D-Glucosaminyl 3-O-Sulfotransferase," The Journal of Biological Chemistry, vol. 272, No. 44), pp. 28008-28019 (1997).
Silk, E., et al., "The role of extracellular histone in organ injury", Cell Death & Disease, vol. 8, No. 5, 1, e2812, pp. 1-11 May 1, 2017.
Singh, A; Tessier, M. B.; Pederson, K.; Wang, X.; Venot, A P.; Boons, G.-J.; Prestegard, J. H.; Woods, R. J. Can. J. Chem. 2016, 10.1139/cjc.
Sismey-Ragatz, et al, "Chemoenzymatic Synthesis with Distinc Pasteurella Heparosan Synthases," J. Biol. Chem., vol. 282, No. 39, pp. 28321-28327 (Jul. 11, 2007).
Solera et al., "Chondroitin sulfate tetrasaccharides: synthesis, three-dimensional structure and interaction with midkine." Chemistry, vol. 22, pp. 2356-2369 (2016).
Sommers, C.D., et al., "Heparin and homogeneous model heparin oligosaccharides form distinct complexes with protamine: Light scattering and zeta potential analysis," Journal of Pharmaceutical and Biomedical Analysis, vol. 140, pp. 113-121. (Year: 2017).
Stabler et al., "Chondroitin sulphate Inhibits NF-κB activity induced by interaction of pathogenic and damage associated molecules." Osteoarthritis and Cartilage, vol. 25, pp. 166-174 (2017).
STN record for Chen et al., dissertation, "Towards de novo synthesis of structure-defined oligosaccharides with heparan sulfate u biosynthetic enzymes", entered into STN: Apr. 20, 2009. 1 page.
Sugigura et al., "Molecular dissection of placental malaria protein VAR2CSA interaction with a chemo-enzymatically synthesized chondroitin sulfate library." Glycoconj. J., vol. 33, pp. 985-994 (2016).
Sugiura et al., "Baculovirus Envelope Protein ODV-E66 Is a Novel Chondroitinase with Distinct Substrate Specificity." J. Biol. Chem., vol. 286, pp. 29026-29034 (2011).
Sugiura et al., "Construction of a Chondroitin Sulfate Library with Defined Structures and Analysis of Molecular Interactions." J. Biol. Chem., vol. 287, pp. 43390-43400 (2012).
Sugiura et al., "Sequential synthesis of chondroitin oligosaccharides by immobilized chondroitin polymerase mutants." Glycoconj. J., vol. 25, pp. 521-530 (2008).
Sugumaran, G., et al., "Simultaneous Sulfation of endogenous Chondroitin Sulfate and Chondroitin-derived Oligosaccharides" The Journal of Biological Chemistry vol. 261 No. 27 pp. 12659-12664, Oct. 1986.
Sundaram, M. et al., "Rational design of low-molecular weight heparins with improved in vivo activity," Proc. Natl. Acad. Sci., vol. 100, No. 2, pp. 651-656 (Jan. 21, 2003).
Supplemental Notice of Allowability and Interview Summary corresponding to U.S. Appl. No. 14/898,865 dated Jan. 12, 2018.
Szajek et al., "The US regulatory and pharmacopeia responses to the global heparin contamination crisis." Nat. Biotechnol. vol. 34, pp. 625-630 (2016).
Szatmary, P., et al., Biology, role and therapeutic potential of circulating histenes in acute inflammatory disorders, J Cell Mol med. Aug. 7, 2018;22 (10:4617-4629.
Takagaki et al., "Enzymatic Reconstruction of a Hybrid Glycosaminoglycan Containing 6-Sulfated, 4-Sulfated, and Unsulfated N-Acetylgalactosamine" Biochemical and Biophysical Research Communications vol. 258 pp. 741-744 (Year: 1999).
Takagaki, K., et al., "Chimeric Glycosaminoglycan Oligosaccharides Synthesized by Enzymatic Reconstruction and Their Use in Substrate Specificity Determination of *Streptococcus* Hyaluronidase," The Japanese Biochemical Society, vol. 127, No. 4, pp. 695-702, Apr. 2000.
Tamura et al., "Synthesis of chondroitin sulfate E octasaccharide in a repeating region involving an acetamide auxiliary." Carbohydr. Res., vol. 343, pp. 39-47 (2008).
Tecle, E.; Diaz-Balzac, C. A.; Bulow, H. E. G3 (Bethesda) 2013, 3, 541.
Teng et al., "Molecular functions of syndecan-1 in disease." Matrix Biol., vol. 31, pp. 3-16 (2012).
Thacker, B. E.; Seamen, E.; Lawrence, R.; Parker, M. W.; Xu, Y.; Liu, J.; Vander, K. C. W.; Eska, J. D. ACS Chem. Biol. 2016, 11, 971.
Tohu et al., Anti-Xa and Anti-IIa Drugs Alter International Normalized Ratio Measurements: Potential Problems in the Monitoring of Oral Anticoagulants Clin. Appl. Thrombos Hemostas, vol. 10, pp. 301-309 (2004).
Tsau, C.; Ito, M.; Gromova, A.; Hoffman, M. P.; Meech, R.; Makarenkova, H. P. Development 2011, 138, 3307.
Tsung et al., "HMGB1 release induced by liver ischemia involves Toll-like receptor 4-dependent reactive oxygen species production and calcium-mediated signaling." J. Exp. Med., vol. 204, pp. 2913-2923 (2007).
Tsung et al., "The nuclear factor HMGB1 mediates hepatic injury after murine liver ischemia-reperfusion." J. Exp. Med., vol. 201, pp. 1135-1143 (2005).
Uchimura et al., "Molecular Cloning and Characterization of an N-Acetylglucosamine-6-O-sulfotransferase," The Journal of Biological Chemistry, vol. 273, No. 35, pp. 22577-22583 (Aug. 28, 1998).
Vann et al., "The Structure of the Capsular Polysaccharide (K5 Antigen) of Urinary-Tract-Infective *Escherichia coli* 010 : K5 : H4 a Polymer Similar to Desulfo-Heparin," Eur. J. Biochem, vol. 116, pp. 359-364 (1981).
Venereau et al., "HMGB1 as biomarker and drug target." Pharmacol. Res. vol. 111, pp. 534-544 (2016).
Vives, R, R., et al., "Sequence analysis of heparan sulphate and heparin oligosaccharides", Biochem. J, 1999, vol. 339, pp. 767-773.
Wang et al., "*E. coli* K5 fermentation and the Preparation of Heparosan, a Bioengineered Heparin Precursor," Biotechnol. Bioeng, vol. 107, No. 7, pp. 968-977 (Dec. 15, 2010).
Wang et al., "Edothelial heparan sulfate deficiency impairs L-selectin- and chemokine-mediated neutrophil trafficking during inflammatory responses." Nat. Immunol. vol. 6, pp. 902-910 (2005).
Wang, Z., et al., "Synthesis of 3-O-sulfated oligosaccharides to understand the . . . ", J Am Chem Soc Apr. 12, 2017;139(14) :5249-5256.
Weber et al., "Renal dysfunction in liver transplant recipients: Evaluation of the critical issues." Liver Transplant., vol. 18, pp. 1290-1301 (2012).
Weitz et al., "Beyond heparin and warfarin: the new generation of anticoagulants," Expert Opin. Investig. Drugs, vol. 16, No. 3, pp. 271-282 (2007).
Weitz, "Potential of new anticoagulants in patients with cancer," Thromb. Res., vol. 125 (Suppl 2), pp. S30-S35 (2010).
Wildhagen et al., "Nonanticoagulant heparin prevents histone-mediated cytotoxicity in vitro and improves survival in sepsis." Blood vol. 123, pp. 1098-1101 (2014).
Written Opinion corresponding to International Application No. PCT/US2019/037993 dated Oct. 18, 2019.
Written Opinion of the International Searching Authority Corresponding to International Application No. PCT/US2018/021986 dated Aug. 1, 2018.
Xu et al., Chemoenzymatic Synthesis of Homogeneous Ultralow Molecular Weight Heparins, Science, vol. 334, No. 6055, pp. 498-501 (Oct. 2011).
Xu et al., "Heparan sulfate is essential for high mobility group protein 1 (HMGB1) signaling by the receptor for advanced glycation end products (RAGE)." J. Biol. Chem. vol. 286, pp. 41736-41744 (2011).
Xu et al., "Homogeneous and reversible low-molecular-weight heparins with reversible anticoagulant activity." Nat. Chem. Biol. vol. 10, pp. 248-250 (2014).
Xu et al., Synthetic oligosaccharides can replace animal-sourced low-molecular weight heparins Sci. Transl. Med. vol. 9, eaan5954 (2017).
Xu J, Zhang X, Monestier M, Esmon NL, and Esmon CT. Extracellular histones are mediators of death through TLR2 and TLR4 in mouse fatal liver injury. J Immunol. 2011; 187:2626-31.

(56) References Cited

OTHER PUBLICATIONS

Xu J, Zhang X, Pelayo R, Monestier M, Ammollo CT, Semeraro F, et al. Extracellular histones are major mediators of death in sepsis. Nat Med. 2009:15:1318-21.
Xu, D. et al., "Engineering sulfotransferases to modify heparan sulfate," Nat Chem Biol, vol. 4, No. 3, pp. 200-202 (Mar. 2008).
Xu, D.; Esko, "Demystifying Heparan Sulfate-Protein Interactions," J. Annu Rev Biochem. 2014, 83, 129.
Xu, D.; Olson, J.; Cole, J. N.; van Wijk, X. M.; Brinkmann, V.; Zychlinsky, A.; Nizet, V.; Eska, J. D.; Chang, Y. C. Infect. Immun. 2015, 83, 3648.
Xu, et al., "Homogeneous low-molecular-weight heparins with reversible anticoagulant activity," Nat Chem Biol., vol. 10, pp. 248-252 (2014).
Xu, Y., et al., "Structure Based Substrate Specificity Analysis of Heparan Sulfate 6-O-Sulfotransferases," ACS Chemical Biology, Nov. 7, 2016, 12(1), pp. 73-82.
Xue et al., "Impact of donor binding on polymerization catalyzed by KfoC by regulating the affinity of enzyme for acceptor." Biochim. Biophys. Acta, vol. 1860, pp. 844-855 (2016).
Yang et al., "An Approach to Synthesize Chondroitin Sulfate-E (CS-E) Oligosaccharide Precursors." J. Organic Chem., vol. 83, pp. 5897-5908 (2018).
Yang et al., "Middle region of the Borrelia burgdorferi surface-located protein 1 (Lmp1) interacts with host chondroitin-6-sulfate and independently facilitates infection." Cell Microbiology, vol. 18, 97-110 (2016).
Yang, "Inflammation plays a dual role in acetaminophen hepatotoxicity." Translational Medicine Journal, vol. 5, No. 3, pp. 129-133 (Jun. 2016).
Yang, J.; Hsieh, P.; Liu, X.; Zhou, W.; Zhang, X.; Zhao, J.; Xu, Y.; Zhang, F.; Linhardt, R. J.; Liu, J. Chem Comm 2017, 53, 1743.
Yang, Z.; et al., "UCSF Chimera, MODELLER, and IMP: an Integrated Modeling System," J. Struct. Biol. 2012; 179, 269.
Yoshinari et al., "Molecular Cloning, Expression, and Enzymatic Characterization of Rabbit Hydroxysteroid Sulfotransferase AST-RB2 (ST2A8), "J. Biochem., vol. 123, pp. 740-746 (1998).
Yu et al., "Highly Efficient Chemoenzymatic Synthesis Beta1-3-Linked Galactosides," Chemical Communications, vol. 46(40), pp. 7507-7509 (2010).
Yusa et al., "N-Linked Oligosaccharides on Chondroitin 6-Sulfotransferase-1 Are Required for Production of the Active Enzyme, Golgi Localization, and Sulfotransferase Activity toward Keratan Sulfate." J. Biol. Chem., vol. 281, pp. 20393-20403 (2006).
Zhang et al., "6-O-Sulfotransferase-1 Represents a Critical Enzyme in the Anticoagulant Heparan Sulfate Biosynthetic Pathway", J. Biol. Chem., vol. 276, pp. 42311-42321 (2001).
Zhang et al., "Solution Structures of Chemoenzymatically Synthesized Heparin and Its Precursors," J. Am. Chem. Soc., vol. 130, pp. 12998-13007 (2008).
Zhang et al., "The Effect of Precursor Structures on the Action of Glucosaminyl 3-O-Sulfotransferase-1 and the Biosynthesis of Anticoagulant Heparan Sulfate," J. Biol. Chem., vol. 276, No. 31, pp. 28806-28813 (2001).
Zhang, Z. et al., "Oversulfated chondroitin sulfate: impact of a heparin impurity, associated with adverse clinical events, on low-molecular-weight heparin preparation," J. Med. Chem., vol. 51, No. 18, pp. 5498-5501, Sep. 25, 2008).
Zhao et al. "Enzymatic route to preparative-scale synthesis of UDP-GlcNAc/GalNAc, their analogues and GDP—fucose," Nat. Protoc., vol. 5, No. 4, pp. 636-646 (2010).
Zhou et al. "Expression of heparin sulfate sulfotransferases in Kluyveromyces lactis and preparation of 3'-phsphoadenosie-5'-phosphosulfate," Glycobiology, vol. 21, No. 6, pp. 771-780 (2011).
Zitvogel et al., "Decoding cell death signals in inflammation and immunity." Cell, vol. 140, pp. 798-804 (2010).
Zong, C.; Huang, R.; Condac, E.; Chiu, Y.; Xiao, W.; Li, Z. Q.; Lu, W.; Ishihara, M.; Wang, S.; Ramiah, A.; Stickney, M.; Azadi, P.; Amster, I. J.; Moremen, K. W., Wang, L.; Sharp, J. S.; Boons, G.-J. J. Am. Chem. Soc. 2016, 138. 13059.
Ham, H., et al., "Design of an Ultralow Molecular Weight Heparin that Resists Heparanase Biodegradation," Journal of Medicinal Chemistry, vol. 66, 2023, pp. 2194-2203.
Office Action (Notice of Allowance) corresponding to U.S. Appl. No. 18/406,942 dated Apr. 30, 2025, p. 9.
Office Action (Notice of allowance) corresponding to Japanese Patent Application No. 2024-008526 dated Jul. 8, 2025, p. 5.
Office Action (Notice of Allowance) corresponding to U.S. Appl. No. 18/406,942 dated Jun. 20, 2025, p. 2.
Office Action (Notice of Reasons for Rejection) corresponding to Japanese Patent Application No. 2022-527682 dated Apr. 15, 2025, p. 8.
Office Action (Decision to Grant) corresponding to Japanese Patent Application No. 2023-129964 dated May 27, 2025, 8 pages.
Patent Certificate Received in Chinese patent Application No. 202310342719.2 dated May 30, 2025.
Office Action (Notice of Allowance) corresponding to U.S. Appl. No. 18/406,942 dated Aug. 4, 2025, p. 2.

* cited by examiner

IR 12-mer-1

12-mer-3

IR 12-mer-1

12-mer-3

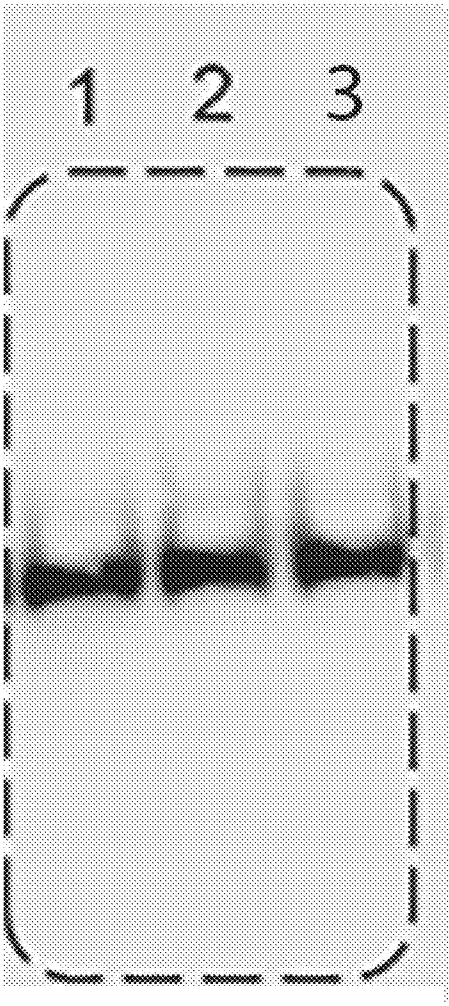
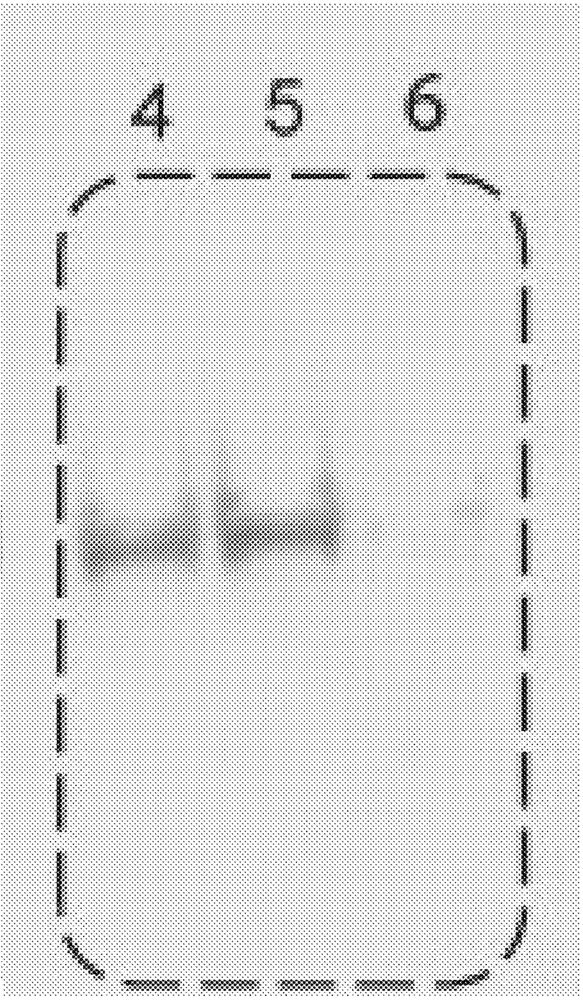
30 KDa
Fig. 8A
Fig. 8B

R =  , $-OCH_3$ , Biotin

X = $-NO_2$ , $-OH$ , $-NH_2$ , $-NHCOCH_3$ , $-OCH_3$ $R_1$ = $-SO_3H$ or -H $R_2$ =  , $-OCH_3$ , Biotin

X= $-NO_2$ , $-OH$ , $-NH_2$ , $-NHCOCH_3$ , $-OCH_3$

Sham

IR 18-mer

HEPARAN SULFATE (HS) OLIGOSACCHARIDES EFFECT IN LIVER ISCHEMIA REPERFUSION INJURY

CROSS-REFERENCE TO RELATED APPLICATIONS

This application is a continuation of PCT International Patent Application No. PCT/US2020/060581, filed on Nov. 13, 2020, herein incorporated by reference in its entirety, which claims benefit of U.S. Provisional Patent Application Ser. No. 62/934,845, filed Nov. 13, 2019, herein incorporated by reference in its entirety.

STATEMENT OF FEDERAL SUPPORT

This invention was made with government support under Grant Numbers HL094463, HL144970, GM128484, and HL142604 awarded by the National Institutes of Health. The government has certain rights in the invention.

TECHNICAL FIELD

The subject matter disclosed herein relates generally to methods and compositions for treating liver ischemia reperfusion (I/R) injury. More specifically, disclosed herein are heparan sulfate oligosaccharide compounds, and methods of using the same, to treat liver ischemia reperfusion (I/R) injury.

BACKGROUND

Liver ischemia reperfusion (IR) injury is a major complication of surgery during liver transplantation and hepatic tumor resection [1]. Liver surgery often requires the use of the Pringle maneuver to reduce blood loss at the expense of potential IR injury [2]. The initial injury starts with the ischemia phase where blood flow is disrupted to the tissue resulting in a lack of oxygen and flow of nutrients. When blood flow is restored to the tissue, it reestablishes oxygen and nutrients to the ischemic tissue. However, this actually enhances the initial ischemic injury by inducing thromboinflammation which is characterized by disturbances in hemostasis and inflammation [1]. Currently, there are no approved drugs to protect against the liver damage caused by IR injury.

Thrombosis and inflammation are traditionally viewed as separate processes. However, growing evidence supports the relationship between thrombosis and inflammation stimulating and reinforcing one another which is collectively described as thromboinflammation [3]. Thromboinflammation is evident in IR injury [3], sepsis [4], and trauma [5].

Damage to the endothelium is central to thromboinflammation pathogenesis. The endothelium acts as an anti-adhesive barrier for the circulatory system by presenting proteoglycans on the cell surface. The heparan sulfate (HS) chains on these proteoglycans can bind to antithrombin III and inhibit coagulation factors FXa and thrombin. The endothelium loses this anti-adhesive and anti-coagulant barrier in thromboinflammatory conditions. Furthermore, tissue factor lies beneath the endothelium and is exposed during vessel wall injury, where it can serve as a potent activator of extrinsic coagulation pathway and subsequent thrombin generation [3]. Additionally, IR injury causes hypoxic cells to release high mobility group box 1 (HMGB1) [6]. HMGB1 has been shown to recruit neutrophils through receptor for advanced glycation end products (RAGE) activation after liver IR [7]. Neutrophil recruitment and infiltration cause further cell death by releasing proteases including myeloperoxidase (MPO) [8]. Severe thromboinflammation can extend beyond the primary affected tissue and lead to multi-organ system failure [3]. Therapeutics that lessen the degree of thromboinflammation are highly desirable to improve patient outcomes [9].

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list or suggest all possible combinations of such features.

Provided in accordance with the presently disclosed subject matter are methods of treating liver ischemia reperfusion (I/R) injury in a subject. In some embodiments, the method comprises providing a subject suffering from liver I/R injury or at risk of suffering liver I/R injury; and administering to the subject one or more heparan sulfate (HS) compounds. In some embodiments, the administering provides anti-inflammation and/or anti-coagulant activity in the subject. In some embodiments, the one or more HS compounds comprises about 5 to about 18 saccharide units, optionally about 12 to about 18 saccharide units. In some embodiments, the one or more HS compounds comprises about 12 saccharide units. In some embodiments, at least one of the one or more HS compounds binds HMGB1.

In some embodiments, the one or more HS compounds comprises the following formula:

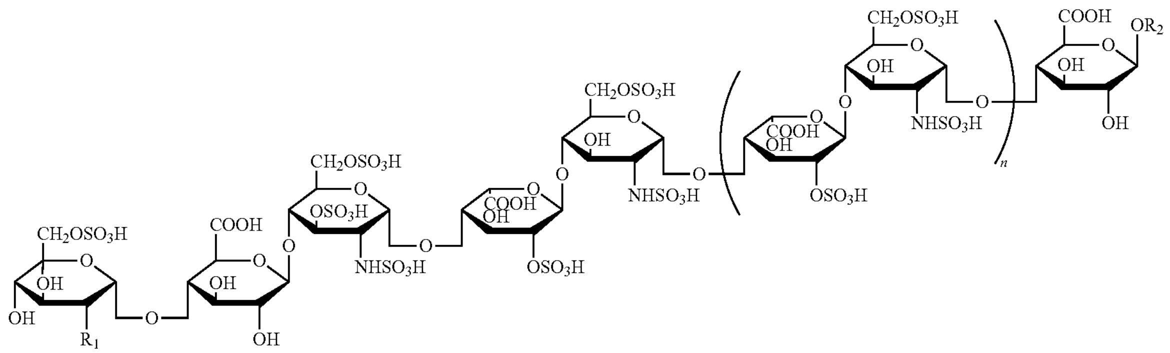

wherein $R_1$ is —$NHSO_3H$ or —$NHCOCH_3$, $R_2$ is —H, alkyl, aryl, substituted alkyl, substituted aryl, or a functional handle and n is an integer of 0-6.

In some embodiments, the one or more HS compounds comprises the following structure:

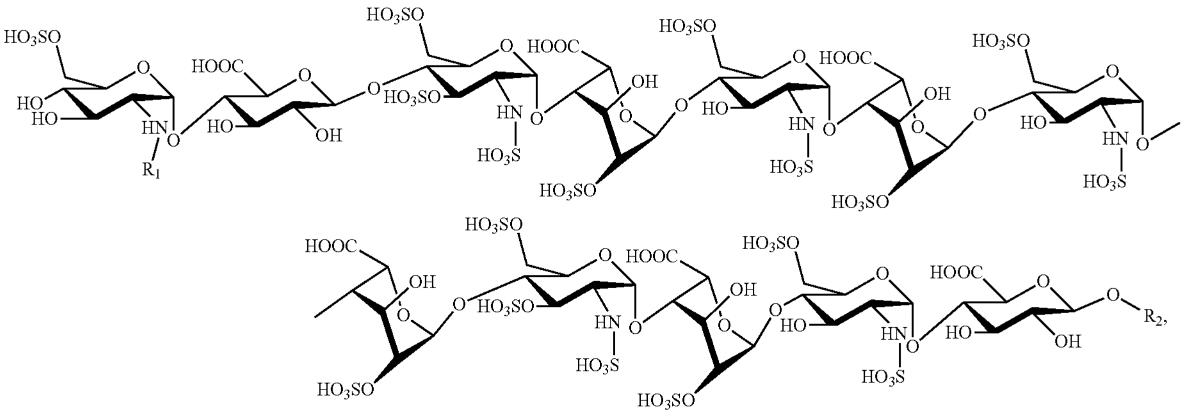

wherein $R_1$ is —$SO_3H$ or —$COCH_3$ and $R_2$ is —H, alkyl, aryl, substituted alkyl, substituted aryl, or a functional handle.

In some embodiments, the one or more HS compounds comprises the following structure:

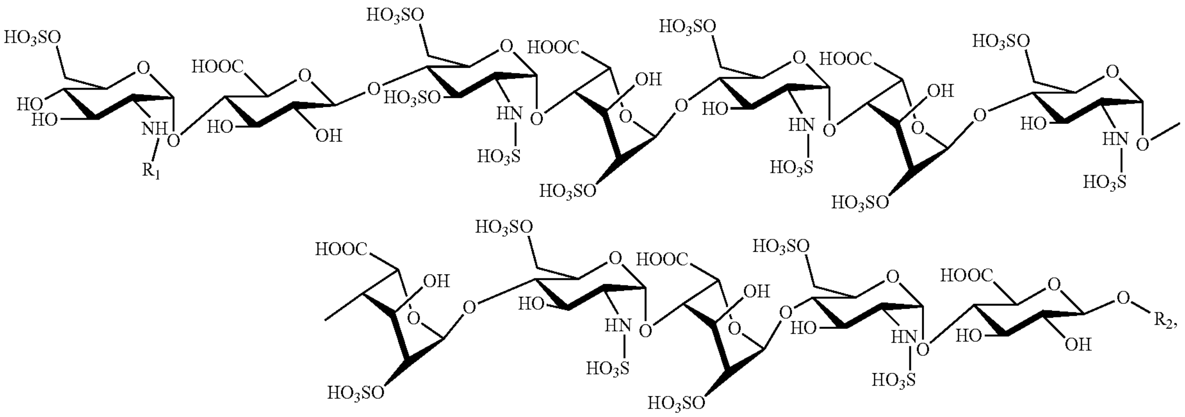

wherein $R_1$ is —$SO_3H$ or —$COCH_3$ and $R_2$ —H, alkyl, aryl, substituted alkyl, substituted aryl, or a functional handle.

In some embodiments, the one or more HS compounds comprises the following formula

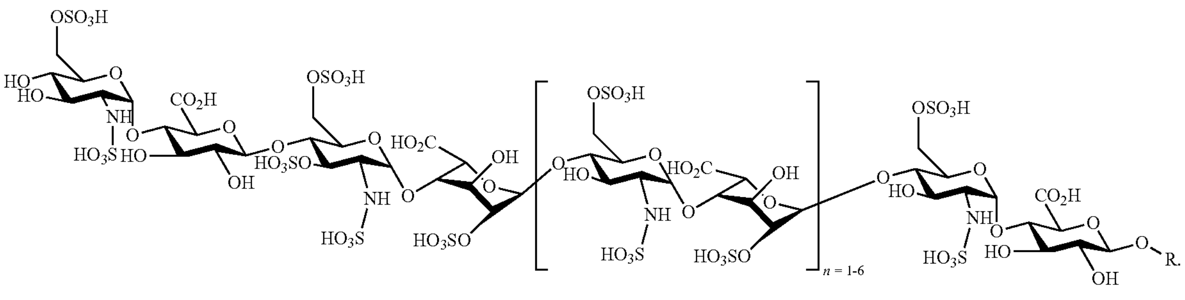

wherein R is —H, alkyl, aryl, substituted alkyl, substituted aryl, or a functional handle.

In some embodiments, the one or more HS compounds comprises the following formula:

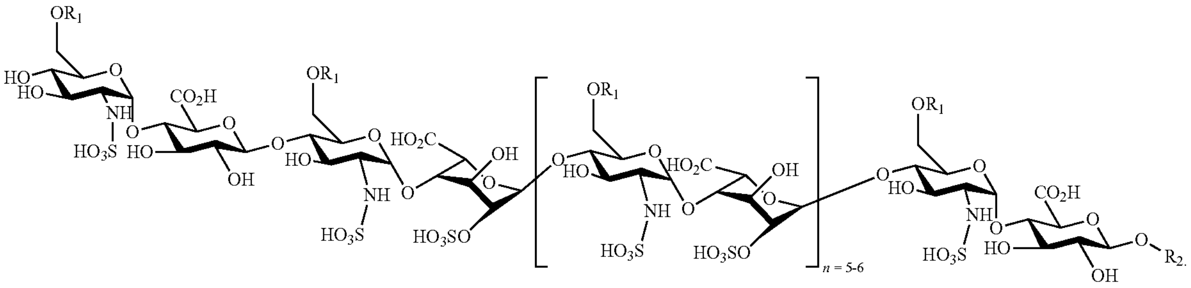

$R_1$ = —$SO_3H$ or —H wherein $R_1$ is —$SO_3H$ or —H and $R_2$ is —H, alkyl, aryl, substituted alkyl, substituted aryl, or a functional handle.

In some embodiments, the one or more HS compounds exists in non-anticoagulant heparin and low-molecular weight heparin and comprises one of the following structural formulas:

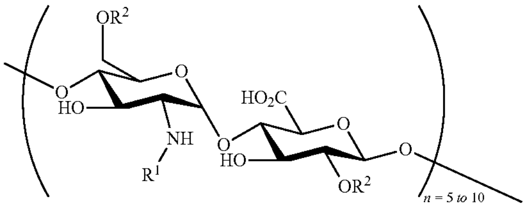

$R^1$ = —$COCH_3$ or —$SO_3H$ $R^2$ = —H or —$SO_3H$

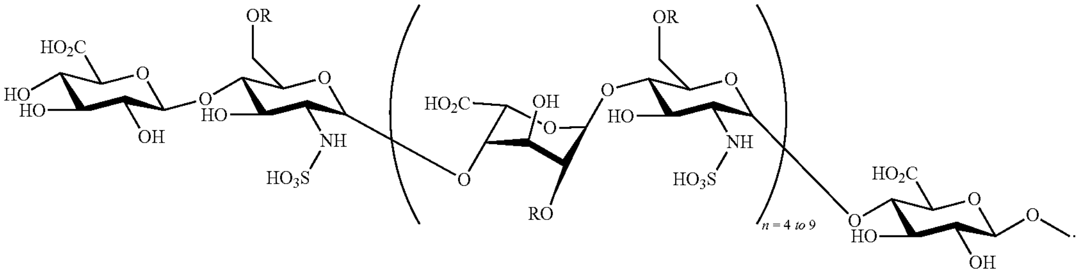

R = —H or —$SO_3H$

In some embodiments, the one or more HS compounds comprises the following formula:

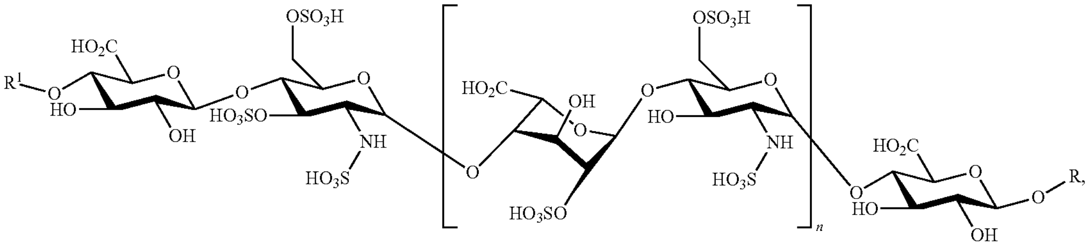

wherein R is —H, alkyl, aryl, substituted alkyl, substituted aryl, or a functional handle; and wherein $R^1$ and n are defined as follows:

in embodiment 1, R1=H, n=1;

in embodiment 2, R1=H, n=2;

in embodiments 3 ($OSO_3H$) and 4 (OH),

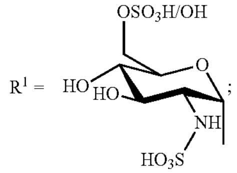

n = 1 in embodiments 5 ($OSO_3H$) and 6 (OH),

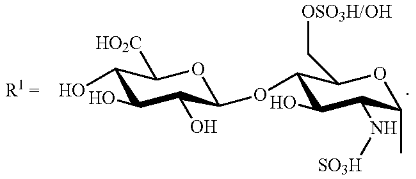

n = 1

In some embodiments, the one or more HS compounds comprises the following formula:

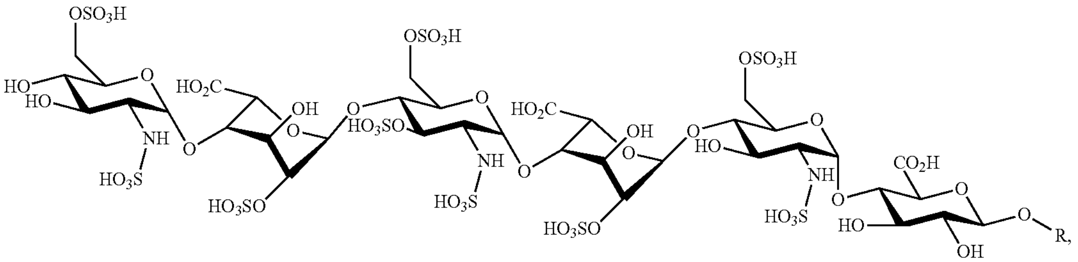

wherein R is —H, alkyl, aryl, substituted alkyl, substituted aryl, or a functional handle.

In some embodiments, the subject in need of treatment is a mammalian subject. In some embodiments, the one or more HS compounds is administered as part of a pharmaceutical composition. In some embodiments, the pharmaceutical composition comprises a HS compound and a pharmaceutically acceptable carrier or adjuvant for administration of the HS compound.

In some embodiments, the administering comprises administering two or more HS compounds, optionally wherein the two or more HS compounds are administered separately but at the same time, optionally wherein the two or more HS compounds are administered at different times, optionally wherein the two or more HS compounds are administered in a single composition.

Provided in accordance with the presently disclosed subject matter heparan sulfate (HS) compounds. In some embodiments, one or more HS compounds are provided as compositions for use in treating liver ischemia reperfusion (I/R) injury in a subject. In some embodiments, the composition comprises: one or more heparan sulfate (HS) compound, optionally wherein the one or more HS compounds comprises about 5 to about 18 saccharide units, optionally about 12 to about 18 saccharide units, further optionally wherein the one or more HS compounds comprises about 12 saccharide units. In some embodiments, administering the composition to the subject provides anti-inflammation and/or anti-coagulant activity in the subject.

In some embodiments, the one or more HS compounds comprises the following formula:

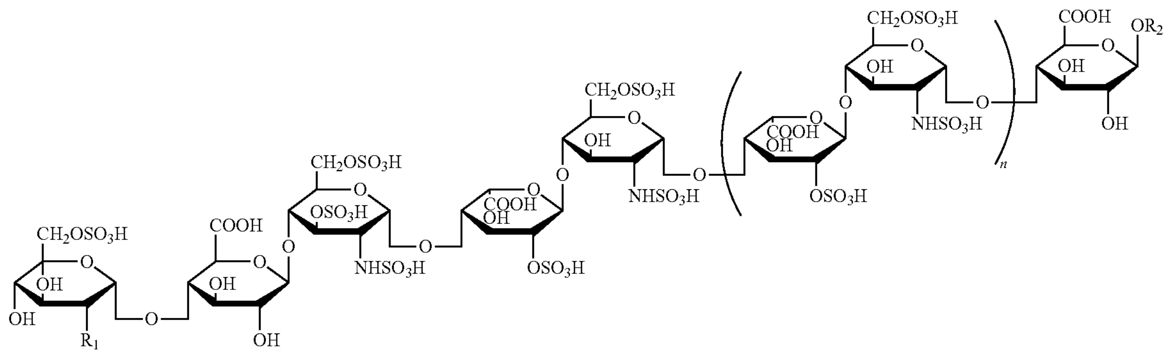

wherein $R_1$ is —$NHSO_3H$ or —$NHCOCH_3$, $R_2$ is —H, alkyl, aryl, substituted alkyl, substituted aryl, or a functional handle and n is an integer of 0-6.

In some embodiments, the one or more HS compounds comprises the following structure:

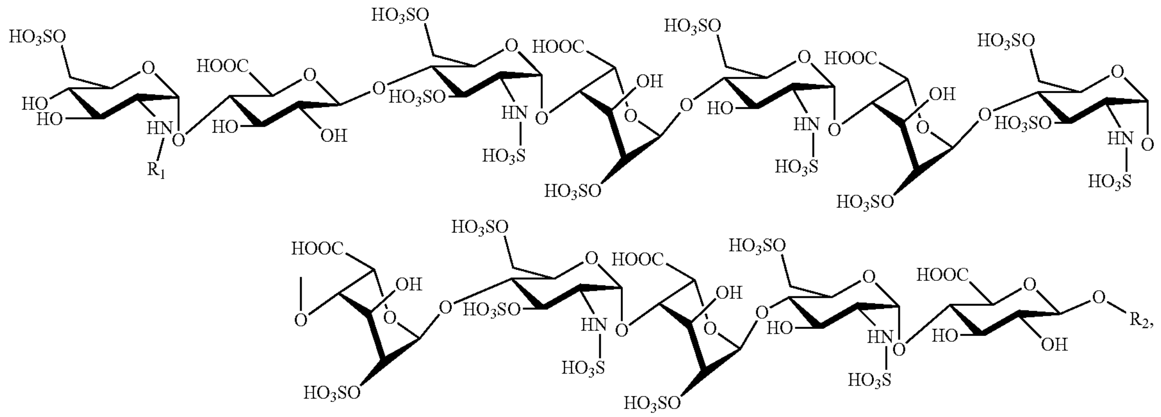

wherein $R_1$ is —$SO_3H$ or —$COCH_3$ and $R_2$ is —H, alkyl, aryl, substituted alkyl, substituted aryl, or a functional handle.

In some embodiments, the one or more HS compounds comprises the following structure:

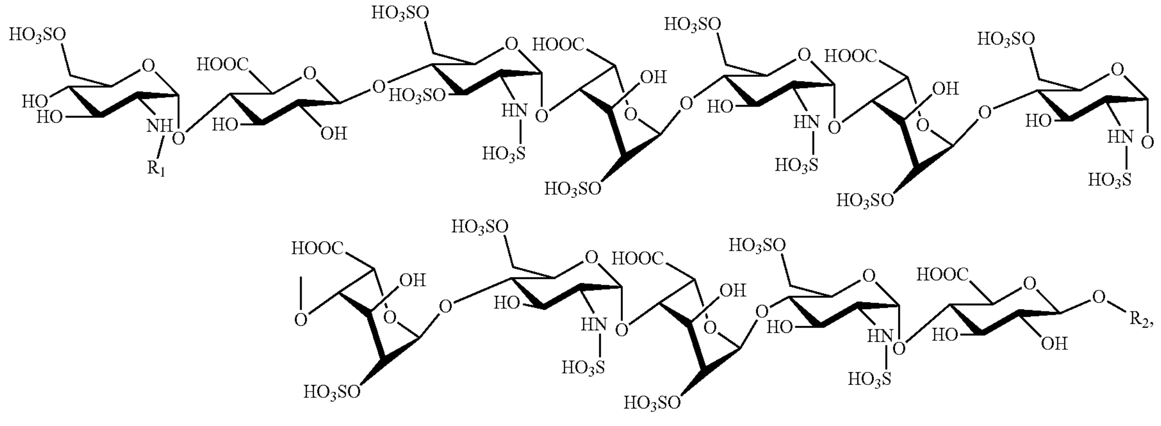

wherein $R_1$ is —$SO_3H$ or —$COCH_3$ and $R_2$—H, alkyl, aryl, substituted alkyl, substituted aryl, or a functional handle.

In some embodiments, the one or more HS compounds comprises the following formula:

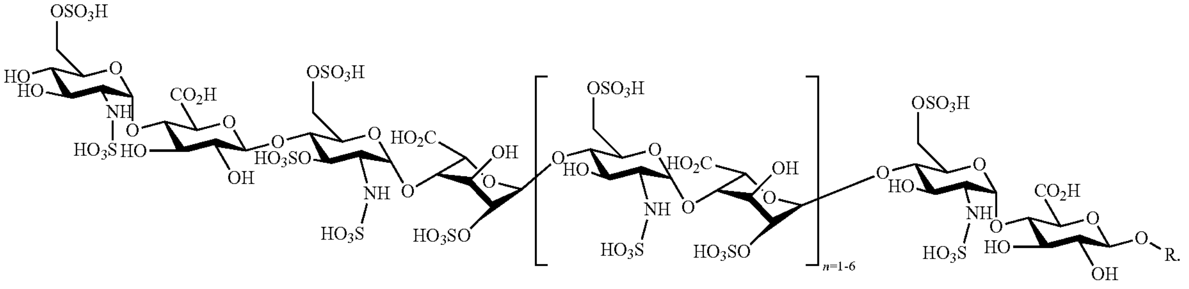

wherein R is —H, alkyl, aryl, substituted alkyl, substituted aryl, or a functional handle.

In some embodiments, the one or more HS compounds comprises the following formula:

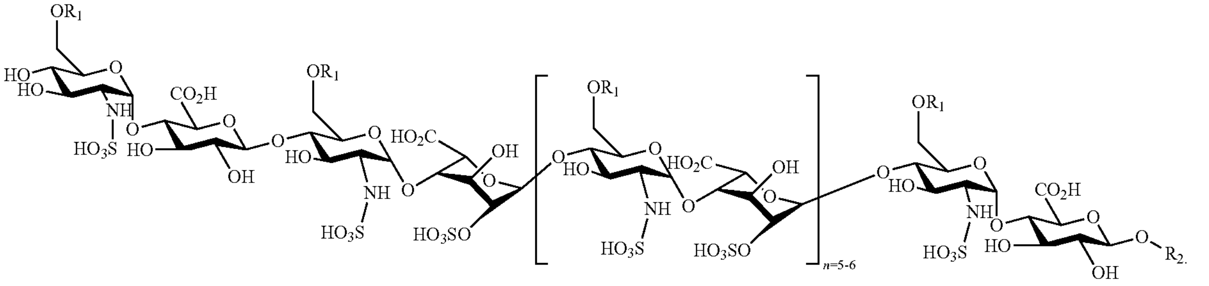

$R_1$ = -$SO_3H$ or -H wherein $R_1$ is —$SO_3H$ or —H and $R_2$ is —H, alkyl, aryl, substituted alkyl, substituted aryl, or a functional handle.

In some embodiments, the one or more HS compounds exists in non-anticoagulant heparin and low-molecular weight heparin and comprises one of the following structural formulas:

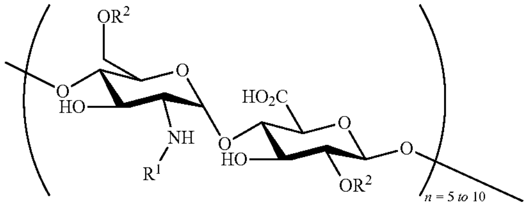

$R^1$ = —$COCH_3$ or —$SO_3H$ $R^2$ = —H or —$SO_3H$

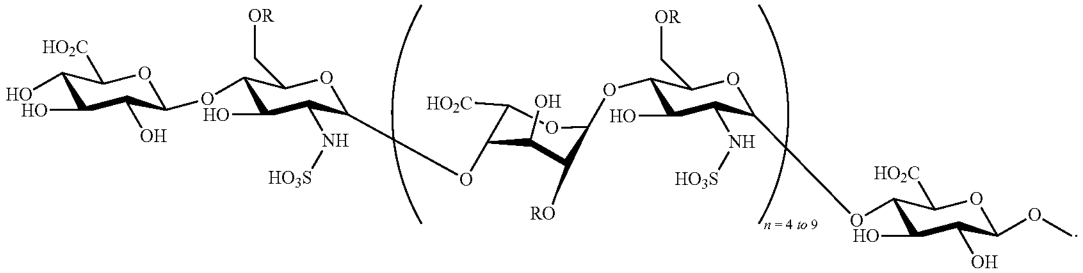

R = —H or —$SO_3H$

In some embodiments, the one or more HS compounds comprises the following formula:

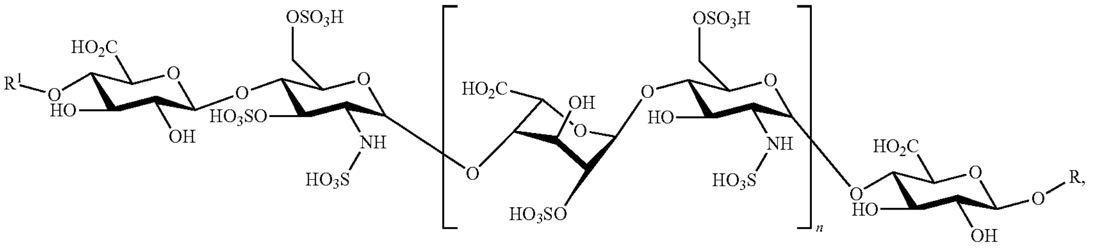

wherein R is —H, alkyl, aryl, substituted alkyl, substituted aryl, or a functional handle; and wherein $R^1$ and n are defined as follows:

in embodiment 1, R1=H, n=1;

in embodiment 2, R1=H, n=2;

in embodiments 3 ($OSO_3H$) and 4 (OH),

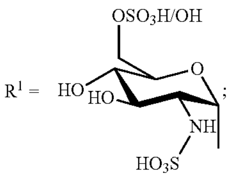

n = 1 in embodiments 5 ($OSO_3H$) and 6 (OH),

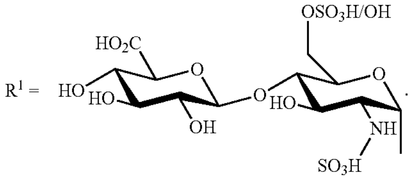

n = 1

In some embodiments, the one or more HS compounds comprises the following formula:

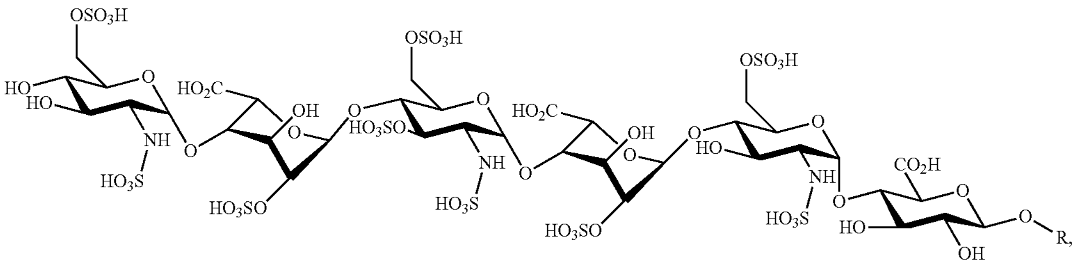

wherein R is —H, alkyl, aryl, substituted alkyl, substituted aryl, or a functional handle.

In some embodiments, wherein the one or more HS compounds binds HMGB1. In some embodiments, the subject in need of treatment is a mammalian subject. In some embodiments, the composition comprises a pharmaceutically acceptable carrier or adjuvant for administration of the one or more HS compounds. In some embodiments, the composition comprises two or more HS compounds.

Accordingly, it is an object of the presently disclosed subject matter to provide methods and compositions for treating liver ischemia reperfusion (I/R) injury. This and other objects are achieved in whole or in part by the presently disclosed subject matter. Further, objects of the presently disclosed subject matter having been stated above, other objects and advantages of the presently disclosed subject matter will become apparent to those skilled in the art after a study of the following description, drawings and examples.

BRIEF DESCRIPTION OF THE DRAWINGS

The presently disclosed subject matter can be better understood by referring to the following figures. The figures are not intended to limit the scope of this presently disclosed subject matter, but merely to clarify and exemplify the presently disclosed subject matter.

FIG. 1A is an illustrated timeline of liver IR model. FIG. 1B is a bar graph showing plasma ALT concentration. P=0.0083. FIG. 1C is a bar graph showing percent area of hepatic necrotic area determined by H&E staining and quantified using original magnification of 100× images. P=0.0077. FIG. 1D is a bar graph showing neutrophil infiltration into ischemic lobe quantified by immunohistochemical staining from 200× magnification images. P=0.0018. Figure lE is a bar graph showing plasma HMGB1 concentration. P=0.0129. FIG. 1F is a bar graph showing plasma syndecan-1 concentration. P=0.0170. Data represent mean±SEM. Sham n=4-5, IR n=4-8. *P<0.05 and **P<0.01 by Student t-test.

FIG. 2A is an illustration of 12-mer structures prepared by chemoenzymatic synthesis. FIG. 2B is a bar graph showing in vitro FXa activity determination for 12-mers with fondaparinux as a positive control. FIG. 2C is a set of images showing Western analysis of HMGB1 pulldown from liver lysate using biotinylated 12-mers.

FIG. 4A. Percent area of hepatic necrotic area determined by H&E staining and quantified using original magnification of 100× images. Sham vs IR, P=0.0078; 12-mer-1 vs. IR, P=0.0287; 12-mer-3 vs IR, P=0.1059. Data represent mean±SEM. Sham n=3, IR n=4,12-mer-1 n=6, and 12-mer-3 n=5. *P<0.05 and P<0.01 vs. IR by one way ANOVA followed by Dunnett's test. FIG. 4B-FIG. 4**E. Representative images of H&E stained liver tissue. 100× magnification. 200 μm scale bar.

FIG. 5A. MPO activity measured in sham or ischemic liver lysate. Sham vs IR, P=0.0121; 12-mer-1 vs IR, P=0.0229. FIG. 5B. Quantitation of average neutrophils per 100× field of view. Sham vs IR, P=0.0248; 12-mer-1 vs IR, P=0.0142; 12-mer-3 vs IR, P=0.0705. Data represent mean±SEM. Sham n=6, IR n=3-4, 12-mer-1 n=4-6, 12-mer-3 n=6. *P<0.05 by one way ANOVA followed by Dunnett's test. FIG. 5C-FIG. 5F. Representative images of neutrophil immunohistochemically stained liver tissue. 200× magnification. 200 μm scale bar. Pink arrows indicate stained neutrophils.

FIG. 6A. Illustration of 6-mer-AXa structure. FIG. 2A legend applies. FIG. 6B. Western analysis of HMGB1 pulldown from liver lysate using biotinylated 6-mer-AXa with 12-mer-3 and 12-mer-1 as a positive control. FIG. 6C. Plasma FXa activity was measured from mice that underwent a sham or IR procedure with administration of 12-mer-3+6-mer-AXa or 6-mer-AXa alone. IR vs. 12-mer-3+6-mer-AXa, P=0.0089; IR vs 6-mer-AXa, P=0.0252. FIG. 6D. Plasma ALT. IR vs Sham, P=0.0026; IR vs 12-mer-3+6-mer-AXa, P=0.0086. Data represent mean±SEM. Sham n=4, IR n=3-5, 12-mer-3+6-mer-AXa n=6, 6-mer-AXa n=6.

FIG. 7A. Sample input. Lane 1: 12-mer-4; Lane 2: 12-mer-2; Lane 3: 12-mer-3; Lane 4: 12-mer-1. FIG. 7B. Sample elution. Lane 5: 12-mer-4; Lane 6: 12-mer-2; Lane 7: 12-mer-3; Lane 8: 12-mer-1.

FIGS. 8A and 8B show full western blot images from HMGB1 pulldown using 12-mer-1 and 6-mer-AXa oligosaccharides. FIG. 8A. Sample input. Lane 1: 12-mer-3; Lane 2: 12-mer-1; Lane 3: 6-mer-AXa. FIG. 8B. Sample elution. Lane 4: 12-mer-3; Lane 5: 12-mer-1; Lane 6: 6-mer-AXa.

FIG. 11A. Experimental design for the IR procedure. FIG. 11B. Graph showing plasma ALT levels measured in sham, IR, and 18-mer treated IR mice. 18-mer significantly reduces ALT levels compared to IR. Data represent mean±SEM. N=5 for sham and n=7 for IR and 18-mer. One-way ANOVA with Dunnett's post-hoc test. *P<0.05, P<0.01. FIG. 11C. Graph showing quantification of necrotic area from H&E stained ischemic liver lobes; FIG. 11D-FIG. 11**F. Representation images of liver tissue stained with hematoxylin and eosin (H&E) for quantitation of necrosis. Original magnification 100×, scale bar 200 μm.

FIG. 12A. Plasma HMGB1 levels, measured by ELISA, are decreased in the 18-mer treated group compared to IR. FIG. 12B. Although not statistically significant. TNF-α plasma levels are trending towards a decrease in the 18-mer treated group. FIG. 12C. Plasma IL-6 levels, measured by ELISA, are decreased in the 18-mer treated group. FIG. 12D. Neutrophil infiltration, measured by immunohistochemistry, was decreased in 18-mer treated group.

DETAILED DESCRIPTION

Figure 1A:
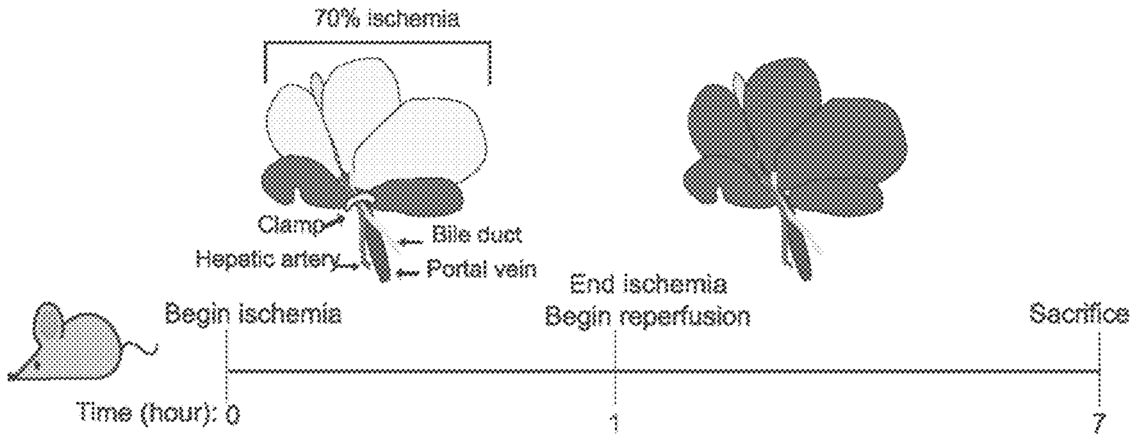
FIGS. 1A to 1F show a mouse model of liver IR increases liver injury markers.

The presently disclosed subject matter now will be described more fully hereinafter, in which some, but not all embodiments of the presently disclosed subject matter are described. Indeed, the presently disclosed subject matter can be embodied in many different forms and should not be construed as limited to the embodiments set forth herein; rather, these embodiments are provided so that this disclosure will satisfy applicable legal requirements.

Heparan sulfate (HS) is structurally similar to the anticoagulant drug heparin. HS and heparin are comprise disaccharide repeating units of glucuronic acid (GlcA) or iduronic acid (IdoA) linked to glucosamine residues that carry sulfo groups [10]. Heparin has higher sulfation and more IdoA residues than HS. Clinical studies using heparin and low molecular weight heparin (LMWH) to treat thromboinflammatory diseases like sepsis and IR are inconclusive on its effect [11,12]. Heparin and its derivatives are complex, structurally uncharacterized oligosaccharide mixtures containing variations in chain length and chemical modifications. The structural heterogeneity makes it difficult to define the relationship of oligosaccharide structure to its biological function. Furthermore, the lack of structurally homogeneous HS oligosaccharides hampers the efforts to exploit the characteristics of HS for use as a therapeutic agent [13]. To address this issue, a chemoenzymatic method to synthesize structurally specific HS oligosaccharides with high efficiency has been developed [14-16]. In accordance with particular aspects of the presently disclosed subject matter, it is demonstrated that certain oligosaccharides that possess anticoagulant activity and anti-inflammation activity (e.g., bind to HMGB1) are more effective in reducing IR-mediated liver injury compared to oligosaccharide that only bind to HMGB1 or only have anticoagulant activity. By using synthetic HS oligosaccharides, rather than heparin or LMWH, the hepatoprotective effect of oligosaccharides can be distinguished.

HS is a sulfated glycosaminoglycan abundant on the cell surface and in the extracellular matrix and has several biological activities including anticoagulation and anti-inflammation. Liver ischemia reperfusion injury is associated with coagulation and inflammatory responses. In accordance with the presently disclosed subject matter, HS oligosaccharides with defined sulfation patterns were synthesized and it was shown that synthetic anticoagulant HS oligosaccharides limit liver ischemia reperfusion injury in a mouse model. Using a small targeted HS library, in accordance with particular aspects of the presently disclosed subject matter, it was demonstrated that an oligosaccharide that possesses both anticoagulant activity and binding affinity to HMGB1, an inflammatory target, decreases injury greater than oligosaccharides that only bind to HMGB1 or only have anticoagulant activity. The presently disclosed HS oligosaccharides provides a new therapeutic option for decreasing liver damage resulting from ischemia reperfusion injury.

By way of elaboration and not limitation, in some embodiments of the presently disclosed subject matter, a hepatoprotection effect from an HS compound disclosed herein involves consideration of size and/or sulfation pattern. In one non-limiting example, a 12-mer oligosaccharide having a sulfation pattern providing anticoagulant activity and anti-inflammation activity provides a hepatoprotection effect. In another non-limiting example, a 12-mer oligosaccharide having a sulfation pattern providing an anti-inflammation activity provides a hepatoprotection effect when administered with a 6-mer having a sulfation pattern anticoagulant activity. In another non-limiting example, an 18-mer HS oligosaccharide having a sulfation pattern that nonanticoagulant and that provides anti-inflammation activity provides hepatoprotection.

In some embodiments of the presently disclosed subject matter, it is shown that a heparan sulfate (HS) 12-mer that can reduce the liver damage caused by ischemia reperfusion injury. The presently disclosed subject matter reduces inflammation responses that damage hepatocytes for liver transplantation and surgery. In some embodiments, the HS compound comprises about 5 to about 18 saccharide units, including 5, 6, 7, 8, 9, 10, 11, 12, 13, 14, 15, 16, 17, or 18 saccharide units. Representative HS compounds are also disclosed in the Figures. In some embodiments, the HS compound is substituted with —H, alkyl, aryl, substituted alkyl, or substituted aryl. In some embodiments, the HS compound is substituted with a functional handle.

I. DEFINITIONS

The terminology used herein is for the purpose of describing particular embodiments only and is not intended to be limiting of the presently disclosed subject matter.

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one skilled in the art. While the following terms are believed to be well understood by one of ordinary skill in the art, the following definitions are set forth to facilitate explanation of the presently disclosed subject matter.

In describing the presently disclosed subject matter, it will be understood that a number of techniques and steps are disclosed. Each of these has individual benefit and each can also be used in conjunction with one or more, or in some cases all, of the other disclosed techniques.

Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of a composition, mass, weight, temperature, time, volume, concentration, percentage, etc., is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, nitro, amino, arylamino, acyl, hydroxyl, aryloxyl, alkoxyl, alkylthio, arylthio, aralkyl, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

The term "aralkyl" refers to an -alkyl-aryl group, optionally wherein the alkyl and/or aryl group comprises one or more alkyl or aryl group substituents.

In some embodiments, the term "bivalent" refers to a group that can bond (e.g., covalently bond) or is bonded to two other groups, such as other alkyl, aralkyl, cycloalkyl, or aryl groups. Typically, two different sites on the bivalent group (e.g., two different atoms) can bond to groups on other molecules. For example, the bivalent group can be an alkylene group.

"Alkylene" can refer to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene ($—CH_2—$); ethylene ($—CH_2—CH_2—$); propylene ($—(CH_2)_3—$); cyclohexylene ($—C_6H_{10}—$); —CH═CH—CH═CH—; —CH═CH—$CH_2$—; $—(CH_2)_q—N(R)—(CH_2)_r—$, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl ($—O—CH_2—O—$); and ethylenedioxyl ($—O—(CH_2)_2—O—$). An alkylene group can have about 2 to about 3 carbon atoms and can further have 6-20 carbons.

"Arylene" refers to a bivalent aryl group.

"Functional handle" is used to refer to chemical groups that facilitate the chemoenzymatic synthesis. In some embodiments, a functional handle is with or without UV absorbance and/or binds or does not bind to a C18-column. In some embodiments, the functional handle can also be referred to as a detectable tag. In some embodiments, the functional handle comprises an alkyl, aryl, substituted alkyl, or substituted aryl group as defined herein, such as p-nitrophenyl.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

II. COMPOUNDS, COMPOSITIONS, AND METHODS

The presently disclosed subject matter provides HS compounds, and compositions comprising the same, including pharmaceutical and/or therapeutic compositions comprising a HS compound, as disclosed herein. In some embodiments, a pharmaceutical composition can comprise one or more HS compounds, as disclosed herein. Methods of treating subjects with the HS compounds are also disclosed.

In some embodiments, the presently disclosed subject matter provides a heparan sulfate (HS) compound. In some embodiments, the presently disclosed subject matter provides a composition, such as a pharmaceutical composition, comprising one or more HS compounds as disclosed herein. Thus, in some embodiments, the HS compound is administered as part of a pharmaceutical composition. In some embodiments, the pharmaceutical composition comprises one or more HS compounds and a pharmaceutically acceptable carrier or adjuvant for administration of the one or more HS compounds. In some embodiments, a method of treating liver ischemia reperfusion (I/R) injury in a subject is provided. In some embodiments, the method comprises providing a subject suffering from liver I/R injury or at risk of suffering liver I/R injury; and administering to the subject one or more HS compounds as disclosed herein. In some embodiments, the one or more HS compounds have sulfation patterns and/or size based on saccharide units that provides anti-inflammation and/or anti-coagulant activity administering the composition to the subject provides anti-inflammation and/or anti-coagulant activity in the subject.

Figure 6A:
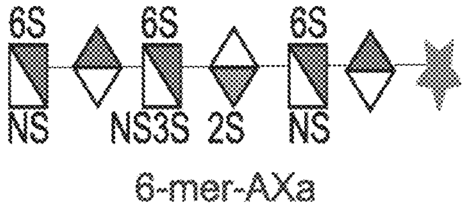
FIGS. 6A through 6D show HMGB1 binding and anticoagulation are necessary for hepatoprotection.
Figure 10:
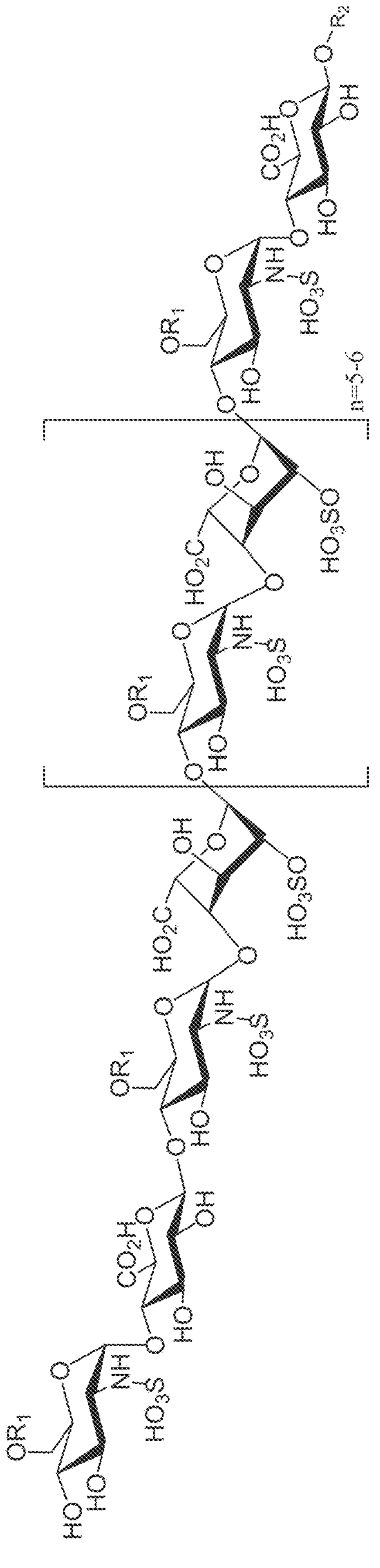
FIG. 10 is a structural formula for representative HS non-anticoagulant 16-18-mer structures of the presently disclosed subject matter. These structures are non-anticoagulant. 18-mer (n=6), used in liver IR, structure includes $R_1$=H and $R_2$=phenyl with X=nitro (para-nitrophenyl), e.g., a functional handle. $R_2$ can also be defined as —H, alkyl, aryl, substituted alkyl, or substituted aryl.
Figure 10:
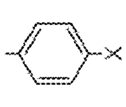

In some embodiments, the HS compound comprises about 5 to about 18 saccharide units, optionally about 12 to about 18 saccharide units. In some embodiments, the HS compound comprises about 12 saccharide units. In some embodiments, the HS compound binds HMGB1. In some embodiments, the HS compound is 12-mer-1, 12-mer-2, 12-mer-3, or 12-mer-4, shown schematically in FIG. 2A. In some embodiments, the HS compound is 6-mer-AXa (shown schematically herein in FIG. 6A). In some embodiments, the HS compound is an 18-mer as shown in FIG. 10 and as discussed in the Examples. Representative synthesis routes for the HS compounds having varying sulfation patterns and size based on saccharide units are provided in the Examples. Approaches for screening for anti-inflammation activity and anti-coagulant activity are provided in the Examples as well.

By way of elaboration and not limitation, in some embodiments of the presently disclosed subject matter, a hepatoprotection effect from an HS compound disclosed herein involves consideration of size and/or sulfation pattern. In one non-limiting example, a 12-mer oligosaccharide having a sulfation pattern that provides anticoagulant activity and anti-inflammation activity provides a hepatoprotection effect. In some embodiments, an 11-mer or a 13-mer having the same or similar sulfation pattern should behave similarly. In another non-limiting example, a 12-mer oligosaccharide having a sulfation pattern that provides an anti-inflammation activity provides a hepatoprotection effect when administered with a 6-mer having a sulfation pattern that provides anticoagulant activity. Here as well, an 11-mer or a 13-mer having the same or similar sulfation pattern should behave similarly. In another non-limiting example, an HS compound on the larger end of the range of sizes disclosed herein, such as an 18-mer HS oligosaccharide having a sulfation pattern that is nonanticoagulant and that provides anti-inflammation activity provides hepatoprotection.

The presently disclosed subject matter reduces inflammation responses that damage hepatocytes for liver transplantation and surgery. In some embodiments, the HS compound comprises about 5 to about 18 saccharide units, including 5, 6, 7, 8, 9, 10, 11, 12, 13, 14, 15, 16, 17, or 18 saccharide units. Representative HS compounds are also disclosed in the Figures. In some embodiments, the HS compound is substituted with —H, alkyl, aryl, substituted alkyl, or substituted aryl. In some embodiments, the HS compound is substituted with a functional handle.

In some embodiments, it is demonstrated that both anti-inflammation (such as via HMGB1 inhibition) and anti-coagulant activity provides protection in an IR model. These activities can come from one molecule (for example, the HS compound referred to herein as 12-mer-1 or as 12-mer AXa) or from the combination dose of two molecules (for example, the HS compound referred to herein as 6-mer-AXa (shown schematically herein in FIG. 6A)+12-mer NS2S6S (also referred to herein as 12-mer-3). Thus, in some embodiments, provided is a combination treatment comprising administering one or more HS compounds having a sulfation pattern and size based on number of saccharide units that provides both anti-inflammation (such as via HMGB1 inhibition) and anti-coagulant activity to a subject need thereof, such as a subject suffering from liver I/R injury or at risk of suffering liver I/R injury. Approaches for assessing anti-inflammation and anti-coagulant activity and HS compounds structures related thereto, including sulfation patterns and size based on number of saccharide units, are disclosed herein, including the Examples. In some embodiments the combination treatment comprises administering 6-mer-AXa+12-mer NS2S6S (also referred to herein as 12-mer-3).

In some embodiments, when two or more HS compounds are administered, the two or more HS compounds are administered separately but at the same time. In some embodiments, the two or more HS compounds are administered at different times but sufficiently proximate to each other to have a desired therapeutic effect. In some embodiments, the two or more HS compounds are administered in a single composition or formulation.

In some embodiments, the HS compound comprises the following formula:

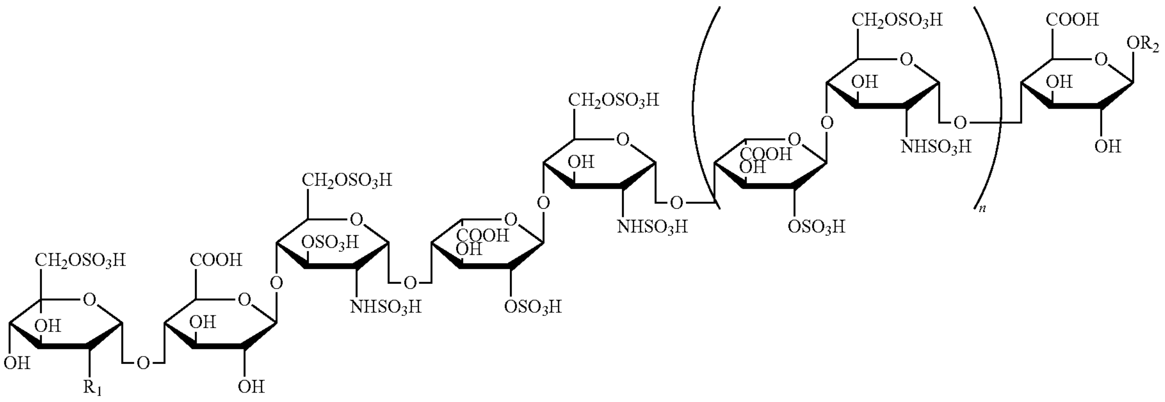

wherein $R_1$ is —$NHSO_3H$ or —$NHCOCH_3$, $R_2$ is —H, alkyl, aryl, substituted alkyl, substituted aryl, or a functional handle and n is an integer of 0-6.

In some embodiments, the HS compound comprises the following structure:

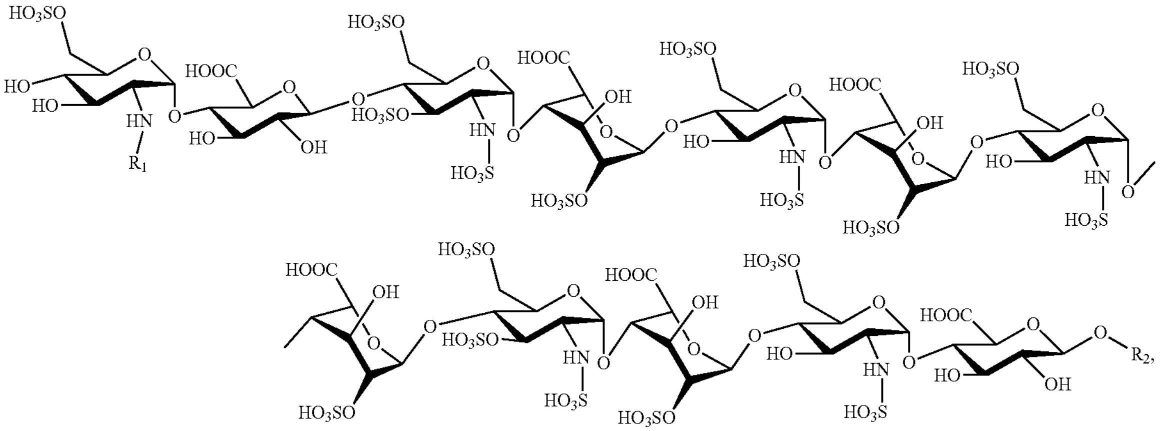

wherein $R_1$ is —$SO_3H$ or —$COCH_3$ and $R_2$ is —H, alkyl, aryl, substituted alkyl, substituted aryl, or a functional handle.

In some embodiments, the HS compound comprises the following structure:

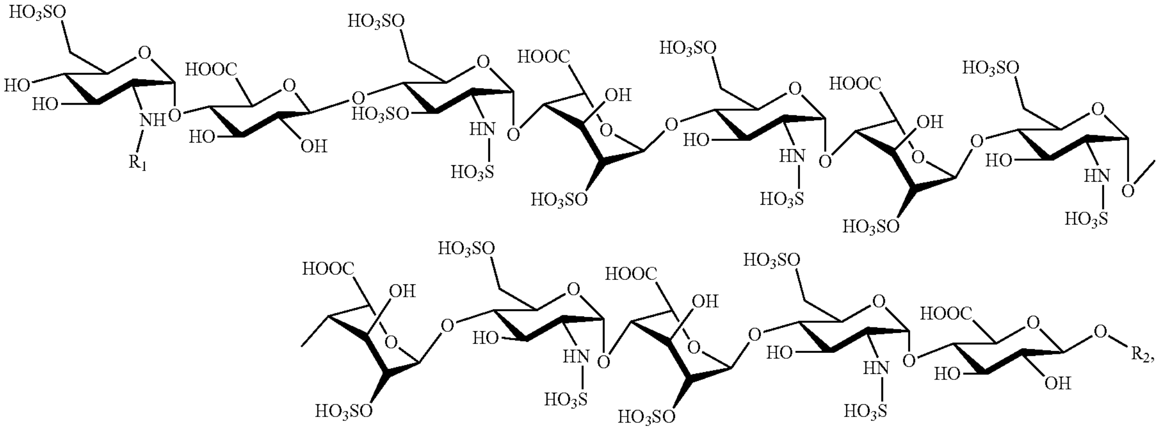

wherein $R_1$ is $-SO_3H$ or $-COCH_3$ and $R_2$ —H, alkyl, aryl, substituted alkyl, substituted aryl, or a functional handle.

In some embodiments, the HS compound comprises the following formula:

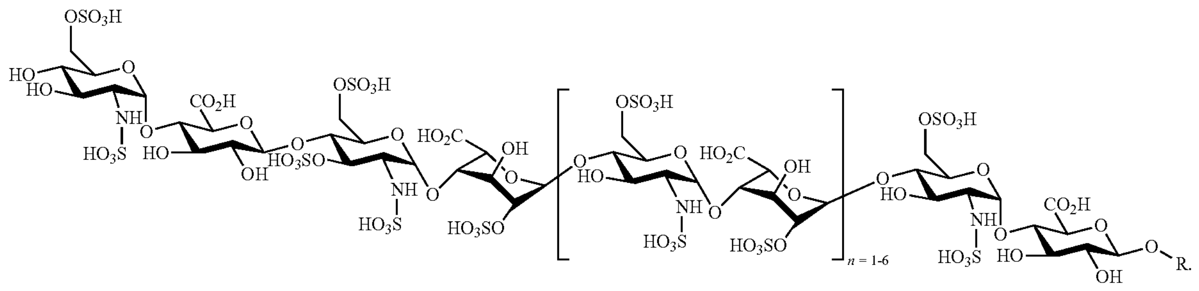

wherein R is —H, alkyl, aryl, substituted alkyl, substituted aryl, or a functional handle.

In some embodiments, the HS compound comprises the following formula:

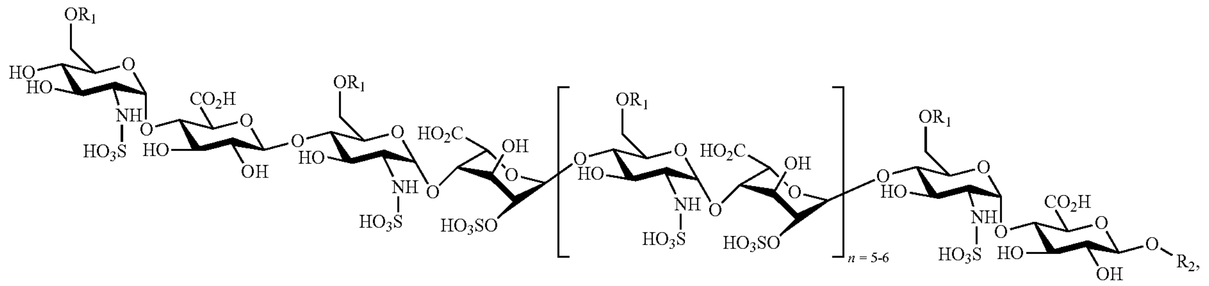

$R_1$ = $-SO_3H$ or —H wherein $R_1$ is $-SO_3H$ or —H and $R_2$ is —H, alkyl, aryl, substituted alkyl, substituted aryl, or a functional handle.

In some embodiments, the HS compound is a HS molecule that exists in non-anticoagulant heparin and low-molecular weight heparin, and comprises one of the following structural formulas:

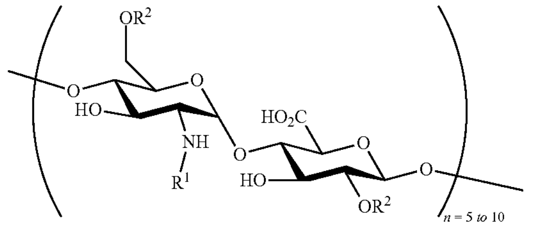

$R^1$ = $-COCH_3$ or $-SO_3H$ $R^2$ = —H or $-SO_3H$

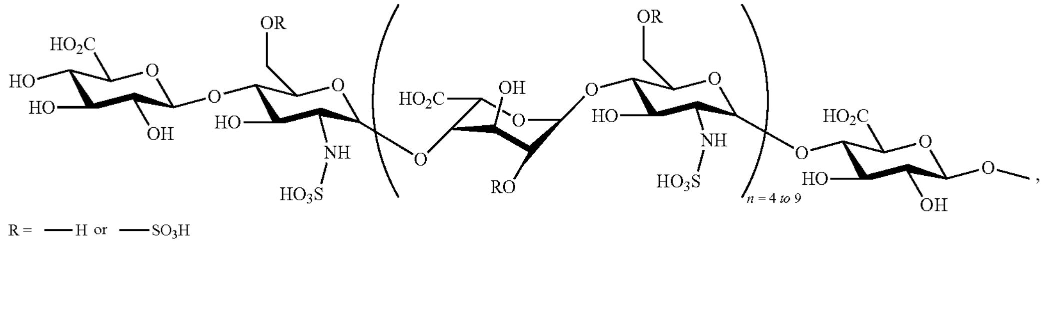

R = —H or $-SO_3H$

In some embodiments, the presently disclosed subject matter provides a HS compound, comprising a 5-mer, a 6-mer or a 7-mer. In one example, the 6-mer is the HS compound referred to herein as 6-mer-AXa (shown schematically herein in FIG. 6A). In some embodiments, the HS compound comprises the following formula:

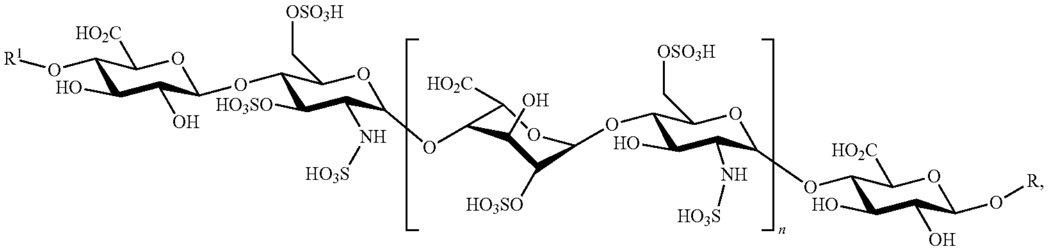

wherein R is —H, alkyl, aryl, substituted alkyl, substituted aryl, or a functional handle; and wherein $R^1$ and n are defined as follows:

in embodiment 1, R1=H, n=1;

in embodiment 2, R1=H, n=2;

in embodiments 3 ($OSO_3H$) and 4 (OH),

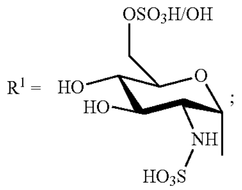

n = 1 in embodiments 5 ($OSO_3H$) and 6 (OH),

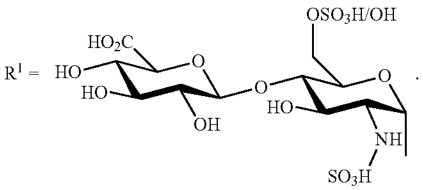

n = 1

In some embodiments, the functional handle comprises an alkyl, aryl, substituted alkyl, or substituted aryl group as defined herein, such as p-nitrophenyl. In one example, the 6-mer is the HS compound referred to herein as 6-mer-AXa (shown schematically herein in FIG. 6A). In some embodiments, the HS compound comprises the formula

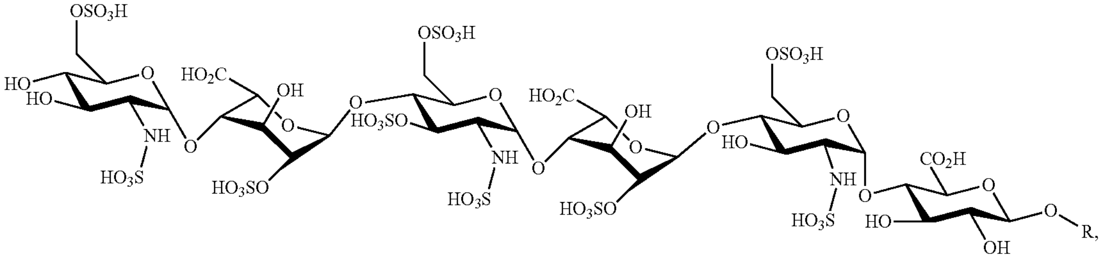

wherein R is —H, alkyl, aryl, substituted alkyl, substituted aryl, or a functional handle.

Figure 9:
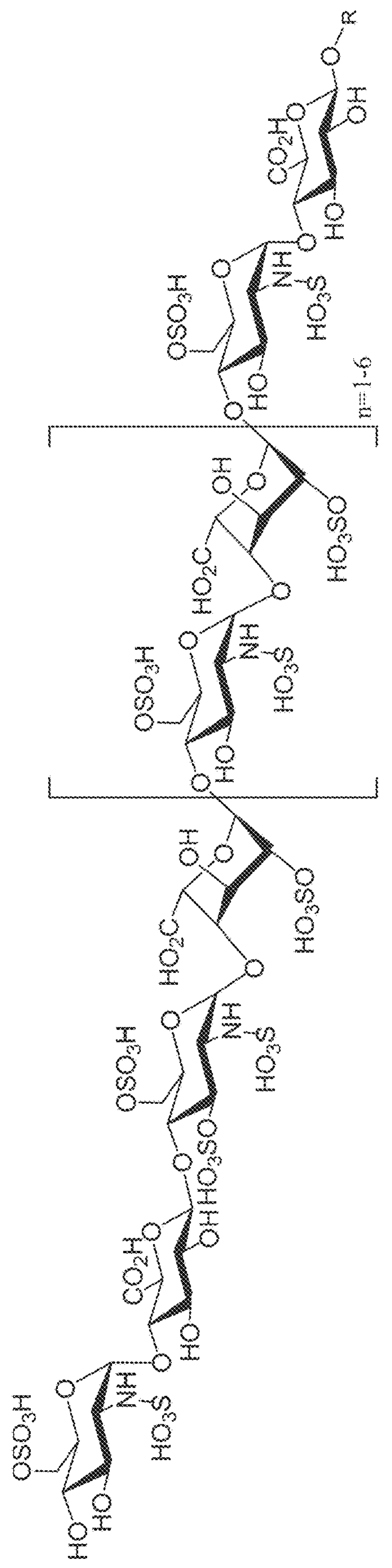
FIG. 9 is a structural formula for representative HS anticoagulant (AXa) 8-18-mer structures of the presently disclosed subject matter. The 12-mer-1 (also referred to as 12-mer AXa (n=3)) is protective in liver ischemia reperfusion mouse model. R is defined as shown and can also be defined as —H, alkyl, aryl, substituted alkyl, substituted aryl, or a functional handle.
Figure 9:
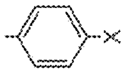

Referring to FIG. 9, presented is a structural formula for representative HS anticoagulant (AXa) 8-18-mer structures of the presently disclosed subject matter. The 12-mer AXa (n=3) is protective in liver ischemia reperfusion mouse model. R is defined as shown and can also be defined as —H, alkyl, aryl, substituted alkyl, substituted aryl, or a functional handle. In some embodiments, such HS compounds have sulfation patterns and/or size based on saccharide units that provides anti-inflammation and/or anti-coagulant activity administering the composition to the subject provides anti-inflammation and/or anti-coagulant activity in the subject.

Referring to FIG. 10, presented is a structural formula for representative HS non-anticoagulant 16-18-mer structures of the presently disclosed subject matter. These structures are non-anticoagulant. 18-mer (n=6), used in liver IR, structure includes $R_1$═H and $R_2$═ phenyl with X=nitro (para-nitrophenyl), e.g., a functional handle. $R_2$ can also be defined as —H, alkyl, aryl, substituted alkyl, or substituted aryl. Thus, in another non-limiting example, an HS compound on the larger end of the range of sizes disclosed herein have a sulfation pattern that is nonanticoagulant and that provides anti-inflammation activity to provide hepatoprotection.

In some embodiments a pharmaceutical composition can also contain a pharmaceutically acceptable carrier or adjuvant. In some embodiments, the carrier is pharmaceutically acceptable for use in humans. The carrier or adjuvant desirably should not itself induce the production of antibodies harmful to the individual receiving the composition and should not be toxic. Suitable carriers can be large, slowly metabolized macromolecules such as proteins, polypeptides, liposomes, polysaccharides, polylactic acids, polyglycolic acids, polymeric amino acids, ammo acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonate and benzoates.

Pharmaceutically acceptable carriers in therapeutic compositions can additionally contain liquids such as water, saline, glycerol and ethanol. Additionally, auxiliary substances, such as wetting or emulsifying agents or pH buffering substances, can be present in such compositions. Such carriers enable the pharmaceutical compositions to be formulated for administration to the patient.

Suitable formulations of pharmaceutical compositions of the presently disclosed subject matter include aqueous and non-aqueous sterile injection solutions which can contain anti-oxidants, buffers, bacteriostats, bactericidal antibiotics and solutes which render the formulation isotonic with the bodily fluids of the intended recipient; and aqueous and non-aqueous sterile suspensions which can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some exemplary ingredients are SDS in the range of in some embodiments 0.1 to 10 mg/ml, in some embodiments about 2.0 mg/ml; and/or mannitol or another sugar in the range of in some embodiments 10 to 100 mg/ml, in some embodiments about 30 mg/ml; and/or phosphate-buffered saline (PBS). Any other agents conventional in the art having regard to the type of formulation in question can be used. In some embodiments, the carrier is pharmaceutically acceptable. In some embodiments the carrier is pharmaceutically acceptable for use in humans.

Pharmaceutical compositions of the presently disclosed subject matter can have a pH between 5.5 and 8.5, preferably between 6 and 8, and more preferably about 7. The pH can be maintained by the use of a buffer. The composition can be sterile and/or pyrogen free. The composition can be isotonic with respect to humans. Pharmaceutical compositions of the presently disclosed subject matter can be supplied in hermetically-sealed containers.

A therapeutic method according to the presently disclosed subject matter comprises administering to a subject in need thereof a HS or related compound as disclosed herein.

An effective dose of a pharmaceutical composition of the presently disclosed subject matter is administered to a subject in need thereof. The terms "therapeutically effective amount," "therapeutically effective dose," "effective amount," "effective dose," and variations thereof are used interchangeably herein and refer to an amount of a therapeutic composition or pharmaceutical composition of the presently disclosed subject matter sufficient to produce a measurable response (e.g. reduced symptoms of liver ischemia reperfusion (I/R) injury). Actual dosage levels can be varied so as to administer an amount that is effective to achieve the desired therapeutic response for a particular subject.

In some embodiments, the quantity of a therapeutic composition of the presently disclosed subject matter administered to a subject will depend on a number of factors including but not limited to the subject's size, weight, age, the target tissue or organ, the route of administration, the condition to be treated, and the severity of the condition to be treated.

The potency of a therapeutic composition can vary, and therefore a "therapeutically effective" amount can vary. However, using the assay methods described herein below, one skilled in the art can readily assess the potency and efficacy of the pharmaceutical compositions of the presently disclosed subject matter and adjust the therapeutic regimen accordingly.

III. SUBJECTS

The subject treated in the presently disclosed subject matter is desirably a human subject, although it is to be understood that the principles of the disclosed subject matter indicate that the compositions and methods are effective with respect to invertebrate and to all vertebrate species, including mammals, which are intended to be included in the term "subject." Moreover, a mammal is understood to include any mammalian species in which treatment of liver ischemia reperfusion (I/R) conditions is desirable, particularly agricultural and domestic mammalian species.

The methods of the presently disclosed subject matter are particularly useful in the treatment of warm-blooded vertebrates. Thus, the presently disclosed subject matter concerns mammals and birds.

More particularly, provided herein is the treatment of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they are also of economical importance to humans. Thus, provided herein is the treatment of livestock, including, but not limited to, domesticated swine (pigs and hogs), ruminants, horses, poultry, and the like.

Liver ischemia reperfusion (IR) injury is a major complication of surgery during liver transplantation and hepatic tumor resection. Liver surgery often requires the use of the Pringle maneuver to reduce blood loss at the expense of potential IR injury. The initial injury starts with the ischemia phase where blood flow is disrupted to the tissue resulting in a lack of oxygen and flow of nutrients. Thus, subjects undergoing surgery during liver transplantation are representative subjects to be treated. However, any suitable subject as would be apparent to one of ordinary skill in the art upon a review of the instant disclosure can be treated, such as a subject suffering from liver I/R injury or at risk of suffering liver I/R injury.

IV. EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Materials and Methods

Chemoenzymatic Synthesis of Oligosaccharides

Figure 13:
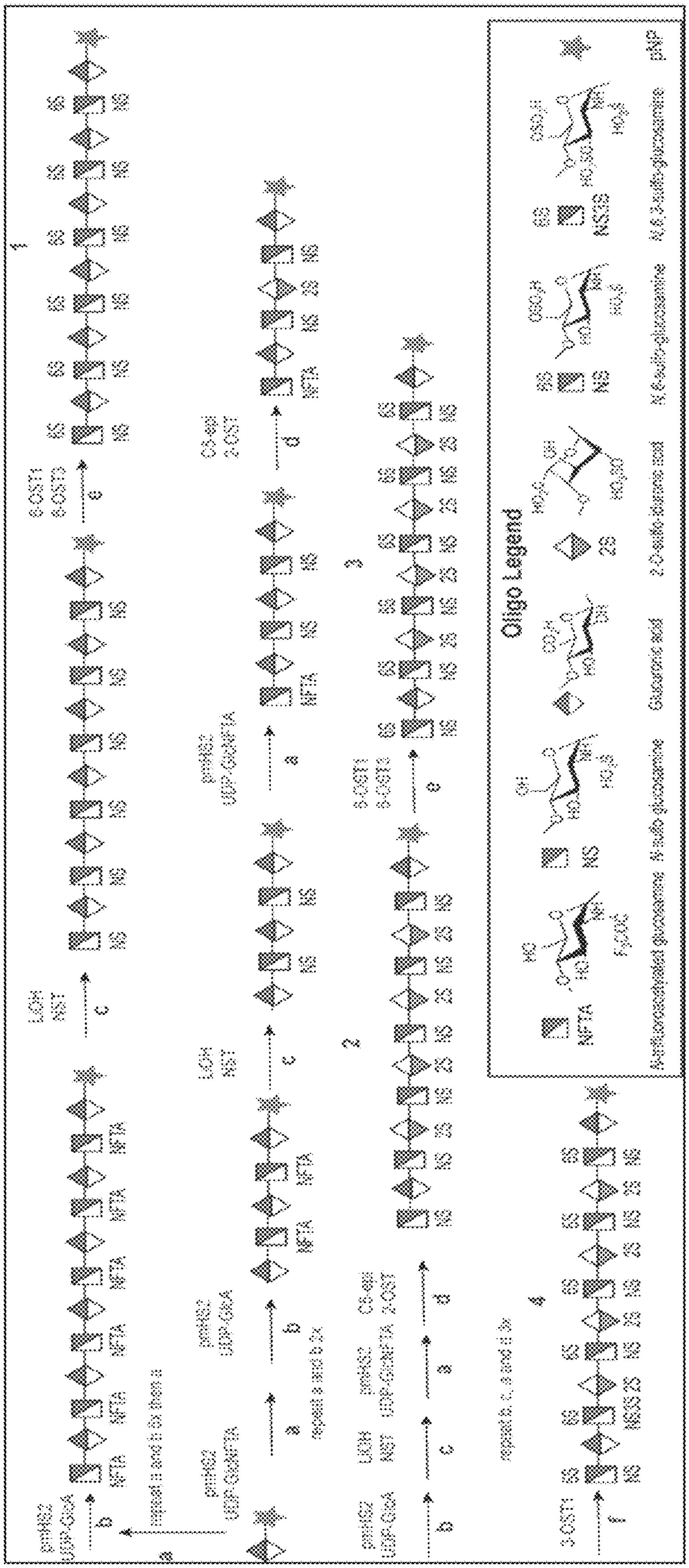
FIG. 13 is a schematic showing the chemoenzymatic synthesis of 12-mers.

The synthesis of the 12-mers and 6-mer-AXa has been previously described [15]. See also FIG. 13. Briefly, for the synthesis of 12-mer-4, glucuronic acid-pNP was elongated with UDP-GlcNTFA (step a) and UDP-GlcA (step b) using pmHS2 to reach 12-mer. Next, GlcNTFA was deprotected using LiOH then N-sulfated with NST (step c) to yield 12-mer N-sulfo glucosamine residues. Next, 6-O-sulfation was installed using 6-OST1 and 6-OST3 (step d) to yield 12-mer-4 GlcNS6S-GlcA-GlcNS6S-GlcA-GlcNS6S-GlcA-GlcNS6S-GlcA-GlcNS6S-GlcA-GlcNS6S-GlcA-pNP.

12-mer-1, -2, and -3 were synthesized by elongating the monosaccharide to a pentasaccharide intermediate. Next, GlcNTFA was deprotected using LiOH then N-sulfated with NST to yield 5-mer with two N-sulfo glucosamine residues. 5-mer NS was elongated with UDP-GlcNTFA to yield a 6-mer intermediate. The glucuronic acid residue in between the two N-sulfo glucosamine residues undergoes epimerization by C5-epimerase and 2-O-sulfation by 2-OST (step e) to yield the 6-mer intermediate GlcNTFA-GlcA-GlcNS-IdoA2S-GlcNS-GlcA-pNP. To generate 6-mer-AXa, this 6-mer intermediate by step c, d, e, and 3-O-sulfation by 3-OST1 (step f) to give GlcNS6S-GlcA-GlcNS6S3S-IdoA2S-GlcNS6S-GlcA-pNP. To generate 12-mer-2, the 6-mer intermediate underwent steps b, c, a, and e repeated three times to yield GlcNS-GlcA-GlcNS-IdoA2S-GlcNS-IdoA2S-GlcNS-IdoA2S-GlcNS-IdoA2S-GlcNS-GlcA-pNP. 12-mer-2 was converted to 12-mer-3 by 6-O-sulfation of GlcNS residues by 6-OST1 and 6-OST-3 (step e) to give the structure GlcNS6S-GlcA-GlcNS6S-IdoA2S-GlcNS6S-IdoA2S-GlcNS6S-IdoA2S-GlcNS6S-IdoA2S-GlcNS6S-GlcA-pNP. Lastly, 12-mer-3 was converted to compound 12-mer-1 by step f to give the structure GlcNS6S-GlcA-GlcNS6S3S-IdoA2S-GlcNS6S-IdoA2S-GlcNS6S-IdoA2S-GlcNS6S-IdoA2S-GlcNS6S-GlcA-pNP. The purity of different 12-mers and 6-mer-AXa were >95% as measured by high resolution DEAE-HPLC. The chemical structures were confirmed by electrospray ionization mass spectrometry (ESI-MS) and NMR[15].

The oligosaccharides were converted to biotinylated versions using the same method as described in PCT International Patent Application Serial No. PCT/US2018/059152. Briefly, 12-mers and 6-mer-AXa with a pNP tag (5-10 mg) and 0.5 mg Pd/C were dissolved in 20 mM NaOAc, pH 5.0 in a total volume of 4 ml. Reaction mixture was vacuumed and refilled with $H_2$ three times. The reaction was then incubated at room temperature for 4 h. After that, it was filtered to remove charcoal. The filtered solution was adjusted to pH 8.5 using 500 mM $Na2HPO_4$. Succinimidyl 6-azidohexanoate (20 molar equivalent of starting oligosaccharides) was added and incubated at 37° C. overnight. Reaction was purified by DEAE-HPLC column to generate azido tagged oligosaccharides. PBS ($pH_{7.4}$) buffer was bubbled with $N_2$ for 5 min to prepare the sample solution of 0.1 M $CuSO_4$, 0.1 M Tris(3-hydroxypropyl-triazolylmethyl) amine (THPTA)(Sigma), 0.15 M sodium ascorbate, 0.01 M azido tagged oligosaccharides and 0.02 M biotin-PEG4-alkyne (Sigma). The mixture of 400 THPTA and 80 μl $CuSO_4$ was vortexed, then 160 μl sodium ascorbate, 200 μl azido tagged oligomers and 200 μl biotin-PEG4-alkyne was added and bubbled with $N_2$ for 2 min, then incubated at 37° C. overnight. The reaction was purified by DEAE-HPLC column to generate biotinylated products. The biotinylated 12-mers and 6-mer-AXa products were confirmed by ESI-MS.

Affinity Purification of HMGB1 from Liver Lysate 6-mer-AXa and 12-mer biotinylated oligosaccharides were prepared using to affinity purify HMGB1 from liver lysate following the method described in PCT International Patent Application Serial No. PCT/US2018/059152. Briefly, liver lysate was prepared by snap freezing tissue in liquid nitrogen at the time of sacrifice. The tissue was mechanically homogenized in buffer containing 200 mM MES, 500 mM phosphate, and 1 mM EDTA at pH 6 followed by three rounds of freeze thawing. The lysed sample were centrifuged at 10,000× g for 15 min at 4° C. Biotinylated HS oligosaccharides (final concentration 0.1 mM) were mixed with 20 μl of fresh liver lysate (~0.6 mg) in 100 mM NaCl 20 mM HEPES pH 7.2 and incubated overnight at 4° C. The purification and biotinylated HS bound complex where achieved using avidin-Sepharose and increasing concentration of NaCl washes. The elution of each sample was separated by gel electrophoresis, transferred to nitrocellulose membrane, and blotted for HMGB1 using anti-HMGB1 primary antibody (Abcam) followed by anti-rabbit HRP (Abcam).

Determination of the In Vitro and Ex Vivo Anti-FXa Activity of Oligosaccharides Assays were based on a previously published method [16]. Briefly, human FXa (Enzyme Research Laboratories) was diluted to 50 U $ml^{-1}$ with PBS. The chromogenic substrate S-2765 (Diapharma) was diluted to 1 mg $ml^{-1}$ in water. For in vitro studies, fondaparinux (available under the trade name ARIXTRA) and 12-mer oligosaccharides were dissolved in PBS at various concentrations (0-131 nM). 16 μl of sample was incubated with 60 μl of 35 μl $ml^{-1}$ antithrombin (Cutter Biologics) for 2 min at room temperature. Next, 100 μl of FXa was added and incubated for 4 min at room temperature. 30 μl of S-2765 substrate was added and the absorbance of the reaction mixture was measured at 405 nm continuously for 5 min. PBS serves as a control sample. The maximum slope for each sample was convert to percent FXa activity by dividing by the maximum slope for the control sample.

For ex vivo studies, mouse plasma collected after the 6 hour reperfusion period and assayed the same as described above.

Liver Ischemia-Reperfusion Surgery Design

Liver ischemia-reperfusion (IR) surgery was performed by the Animal Surgery Core Laboratory of the McAllister Heart Institute, University of North Carolina Chapel Hill, NC. The mouse experiments were approved by the UNC Animal Care and Use Committees and complied with National Institutes of Health guidelines. Male C57BL/6J mice, approximately 8 weeks old, were used in the IR surgeries. Mice received a subcutaneous (SC) injection of 1 mg/kg oligosaccharide or the equivalent volume of saline 30 minutes prior to the surgical procedure. For the combination treatment of 12-mer-3+6-mer-AXa, equal concentration of each oligosaccharide was combined into a single solution. Under ketamine/xylazine anesthesia, an abdominal midline incision was made to expose the portal vein. A clamp was placed on the portal vein and bile duct to three major liver lobes to cause a 70% hepatic ischemia. Visible blanching of the ischemic liver lobes confirmed correct placement of the clamp. A temporary stitch closure of the muscle and skin over the clamp was used to prevent dehydration during the ischemia phase. Mice stayed on a heating pad and under anesthesia during the ischemia phase (60 minutes). The clamp was removed after 60 minutes and the ischemia liver lobes regained their red color as blood began to reperfusion the tissue, an indicator of correct reperfusion occurring. The incisions were closed in two layers with 5-0 silk sutures and the mice returned to their active state (no anesthesia used during the reperfusion phase). After 6 hours, the mice were re-anaesthetized, blood was drawn via cardiac puncture and ischemia liver lobes were harvested for histology (fixed in 10% formalin).

Evaluation of Liver I/R Injury

Plasma ALT was measured using the ALT Infinity reagent (Thermo Fisher) following the manufacturer's instructions. Plasma TNF-α was measured using Mouse TNF-α DuoSet Kit (R&D Systems) according to the manufacturer's instructions. Plasma HMGB1 levels were determined using HMGB1 ELISA Kit (Tecan US) according to the manufacturer's instructions. Plasma syndecan-1 levels were determined using Mouse Syndecan-1 ELISA (CellSciences) according to manufacturer's instructions. Plasms IL-6 levels were determined using Mouse IL-6 ELISA (R&D Systems).

Histology/Immunohistochemistry

Ischemia liver tissues were fixed in 10% neutral buffered formalin for 24 hours at room temperature, paraffin-embedded, and sectioned. Liver sections (4 μm) were stained with hematoxylin-eosin (H&E) or immunostained with monoclonal antibodies anti-neutrophil (Abcam, Ab 2557, NIMP-$R_{14}$) followed by goat anti-rat or goat anti-rabbit biotinylated secondary antibodies (Abcam). Embedding, sectioning and H&E staining were performed at the Animal Histopathology and Laboratory Medicine Core Facility at UNC Chapel Hill. H&E analyses were performed by the Translational Pathology Laboratory Core Facility at UNC Chapel Hill using Aperio ImageScope Software (Leica Biosystems, Concord, Canada). IHC images were captured using an HD camera attached to a bright field microscope (Leica DM 1000 LED, Leica Microsystems Inc., IL, USA) and were processed using ImageJ. For neutrophil quantitation, five 100× images were randomly selected for each sample and the average neutrophils/field were reported.

MPO Activity

Ischemia liver lobe was mechanically homogenized in 50 mM CTAB 50 mM potassium phosphate pH 6 at a ratio of 100 μl buffer per 10 mg tissue. Samples were centrifuged at 15,000×g for 20 min 4° C. and the supernatant was collected and stored at −20° C. Total protein concentration was measured by Bradford assay. 10 μl of liver lysate was incubated with 80 μl of 0.75 mM $H_2O_2$ and 110 μl of TMB (TMB liquid reagent, ready-to-use, Sigma) for 10 minutes at 37° C. with gentle agitation. The reaction was stopped by addition of 2.5 M $H_2SO_4$ and read at 450 nm. Activity (U/g protein) was calculated as absorbance of sample minus the absorbance of the blank divided by incubation time. This value was normalized by the protein concentration.

Statistical Analysis

All data are expressed as mean±SEM. Statistical significance between experimental and control groups were analyzed by two-tailed unpaired Student t test, between multiple groups by one-way ANOVA followed by Dunnett's or Tukey's multiple comparison's test, and Kaplan-Meier survival curves by log-rank test using GraphPad Prism software (version 7.03; GraphPad Software, Inc., graphpad.com/scientific-software/prism/)

Example 1

Liver IR Increases Liver Injury and Inflammation

Figure 1B:
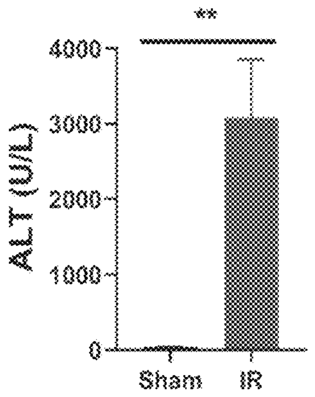
Figure 1C:
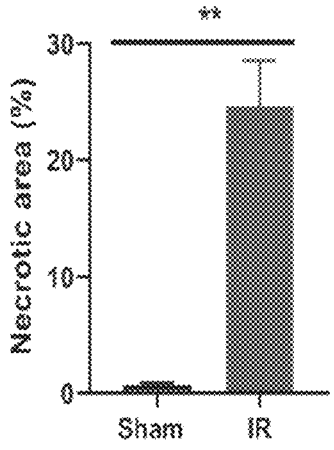
Figure 1D:
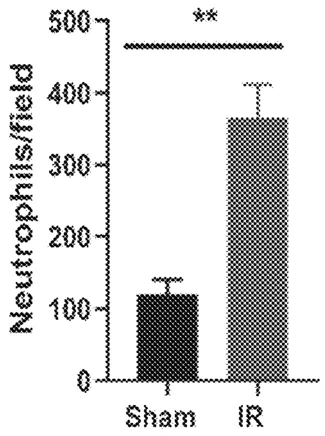
Figure 1E:
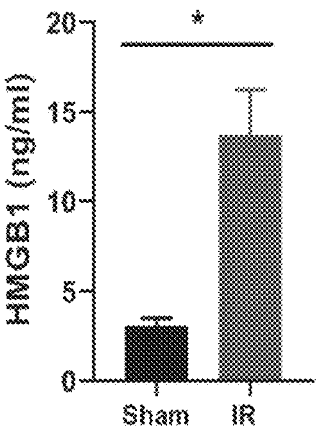
Figure 1F:
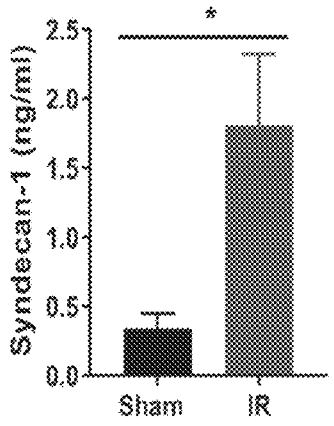

A partial liver IR injury mouse model was used to evaluate the in vivo efficacy of the oligosaccharides. In this model, a clamp was used to induced ischemia in 70% of the liver (FIG. 1A). After 1 hour, the clamp was removed and the reperfusion period begins. Animals were sacrificed after 6 hours of reperfusion. Liver injury was measured by elevations in plasma alanine aminotransferase (ALT), necrotic cell area, and neutrophil infiltration into the ischemic liver (FIGS. 1B-1D). Additionally, IR led to significant increases in plasma HMGB1 (FIG. 1E, P=0.013) and syndecan-1 (FIG. 1F, P=0.017). Elevated plasma HMGB1 and syndecan-1 levels are indicators of cell death and endothelium damage [17,18].

Example 2

HMGB1 Binds to Highly Sulfated HS Oligosaccharides

Figure 2A:
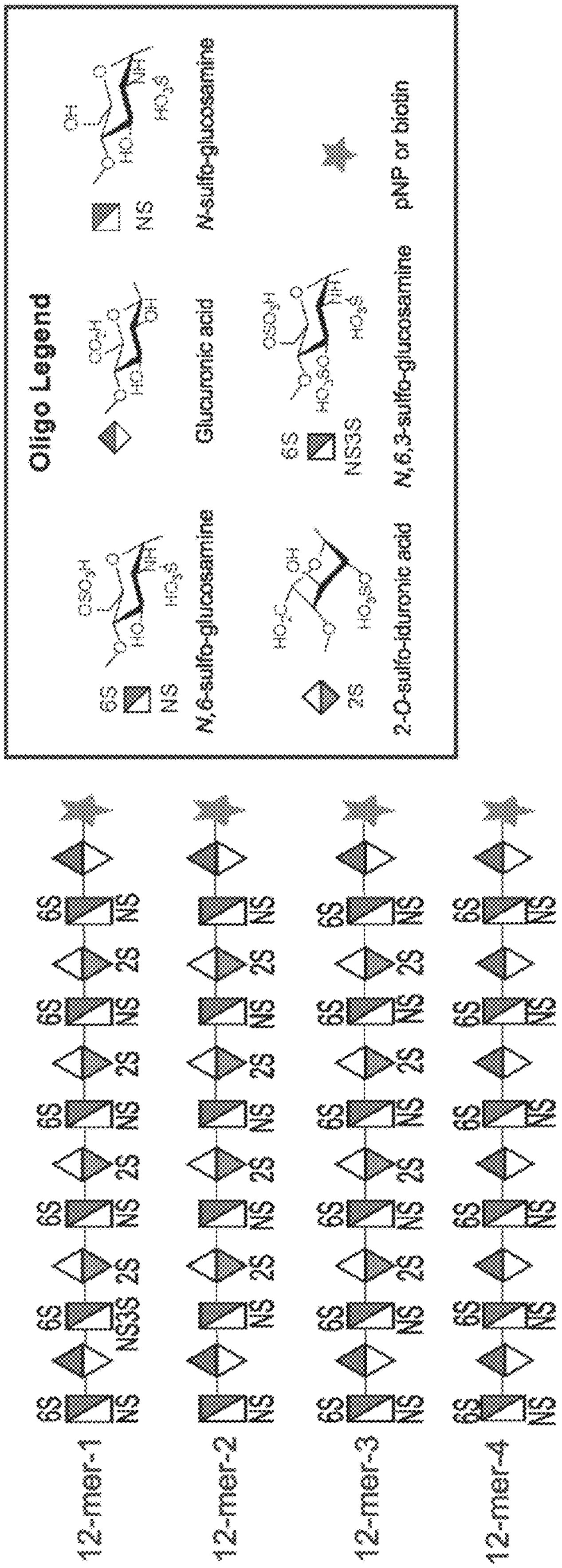
FIGS. 2A to 2C show that HMGB1 binds to highly sulfated 12-mers.
Figure 2B:
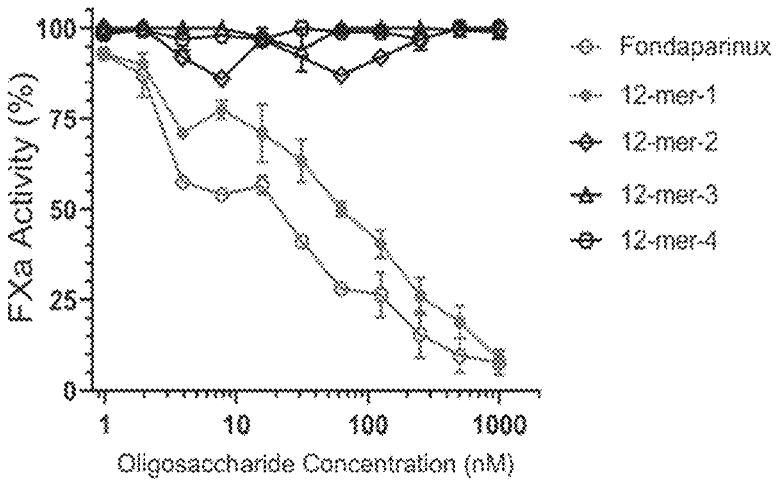
Figure 2C:
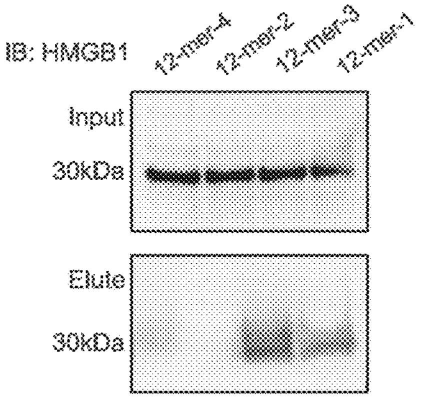

HMGB1 has been implicated in the damaging inflammation response following liver IR [17,19]. In a recent report, HMGB1 binding to HS oligosaccharides of specific residue-repeat lengths was explored [20]. In this Example a panel of 12-mers that vary in sulfation degrees and 2-O-sulfo iduronic acid residues was tested. The access to these 12-mers allowed for the further dissection of the effect of sulfations or 2-O-sulfo iduronic acid residues on HMGB1 binding (FIG. 2A). The panel included four 12-mers covering different sulfation types in the present study. 12-mer-1 has the highest degree of sulfation, carrying 17 sulfo groups and four 2-O-sulfo iduronic acid residues. 12-mer-2 has 10 sulfo groups, the lowest among four 12-mers, and contains four 2-O-sulfo iduronic acid residues. 12-mer-3 contains 16 sulfo groups and four 2-O-sulfo iduronic acid residues. The structural difference between 12-mer-1 and 12-mer-3 is that 12-mer-1 contains a 3-O-sulfo group in one glucosamine residue, but this 3-O-sulfation is not present in 12-mer-3. 12-mer-4 contains 12 sulfo groups and has no 2-O-sulfo iduronic acid residues. The anticoagulant activity of 12-mer-1 was similar to fondaparinux, an FDA approved anticoagulant drug available under the trade name ARIXTRA, as measured by inhibiting the activity of factor Xa (anti-FXa). 12-mer-1 and fondaparinux have anti-FXa $IC_{50}$ values of 63 and 18 nM respectively, while 12-mer-2, -3, and -4 did not display anti-FXa activity and thereby have no anticoagulant activity (FIG. 2B). Next, oligosaccharides appended with biotin tags were used to pull down endogenous HMGB1 from liver lysate (FIG. 2C). Interestingly, 12-mer-1 and 12-mer-3 successfully pull down HMGB1, suggesting that at this size of oligosaccharide, degree of sulfation is an important factor for HMGB1 binding.

Figures 7A, 7B:
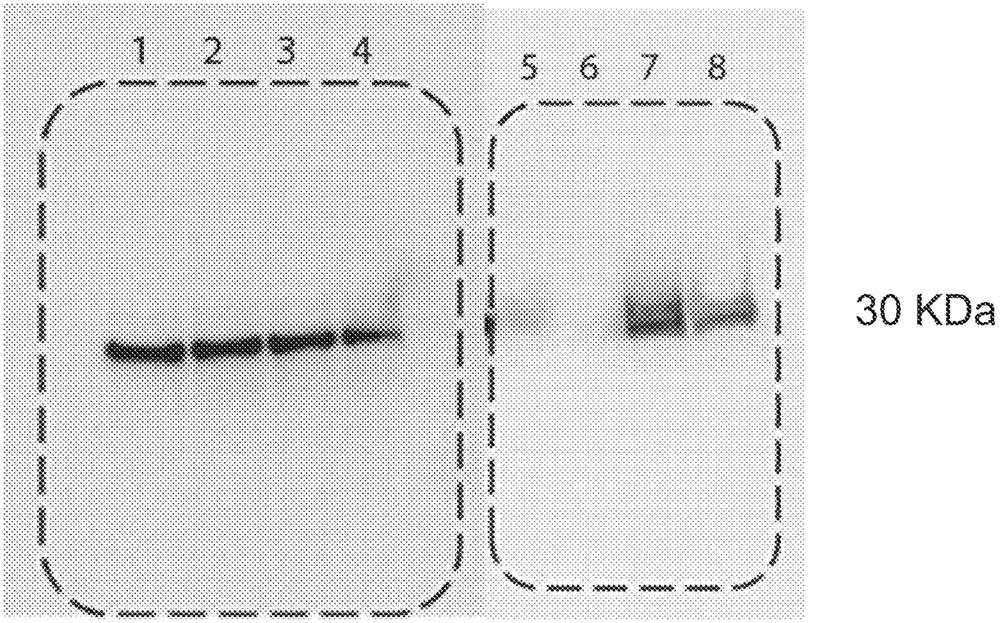
FIGS. 7A and 7B show full western blot images from HMGB1 pulldown using oligosaccharides.

Referring to FIGS. 7A and 7B, shown are western blot images from HMGB1 pulldown using oligosaccharides. FIG. 7A: Sample input. Lane 1: 12-mer-4; Lane 2: 12-mer-2; Lane 3: 12-mer-3; Lane 4: 12-mer-1. FIG. 7B: Sample elution. Lane 5: 12-mer-4; Lane 6: 12-mer-2; Lane 7: 12-mer-3; Lane 8: 12-mer-1.

Referring to FIGS. 8A and 8B, shown are full western blot images from HMGB1 pulldown using 12-mer-1 and 6-mer-AXa oligosaccharides. FIG. 8A: Sample input. Lane 1: 12-mer-3; Lane 2: 12-mer-1; Lane 3: 6-mer-AXa. FIG. 8B: Sample elution. Lane 4: 12-mer-3; Lane 5: 12-mer-1; Lane 6: 6-mer-AXa.

Example 3

12-mer-1 Decreases Liver Injury After IR

Figure 3A:
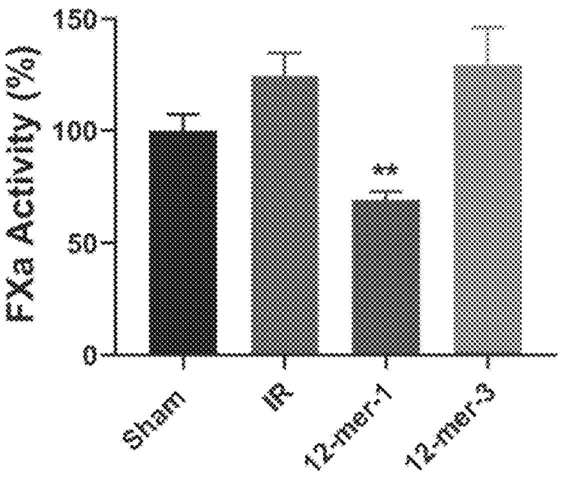
FIGS. 3A and 3B show in vivo determination of anticoagulation and liver injury after IR using 12-mer-1 and 12-mer-3. Plasma FXa activity (FIG. 3A) and ALT (FIG. 3B) was measured from mice that underwent a sham or IR procedure with 12-mer-1 or 12-mer-3 administration. 12-mer-1 significantly decreased FXa activity (12-mer-1 vs IR, P=0.0057) and ALT compared to IR (Sham vs IR, P=0.0233; 12-mer-1 vs. IR, P=0.0480; 12-mer-3 vs IR, P=0.6200). Data represent mean±SEM. N=5-6 for all groups. *P<0.05 and **P<0.01 by one way ANOVA followed by Dunnett's test.
Figure 3B:
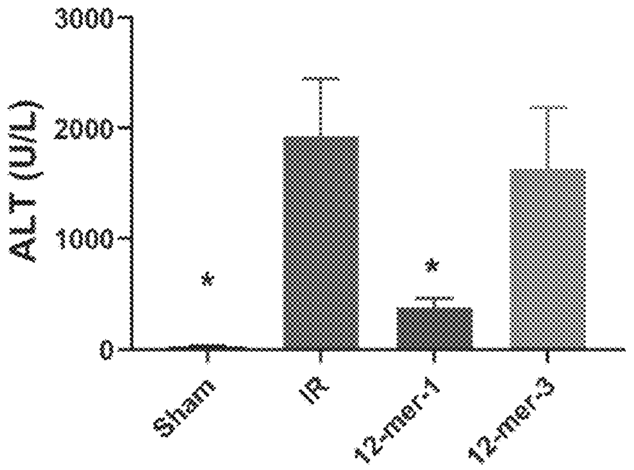
Figure 4A:
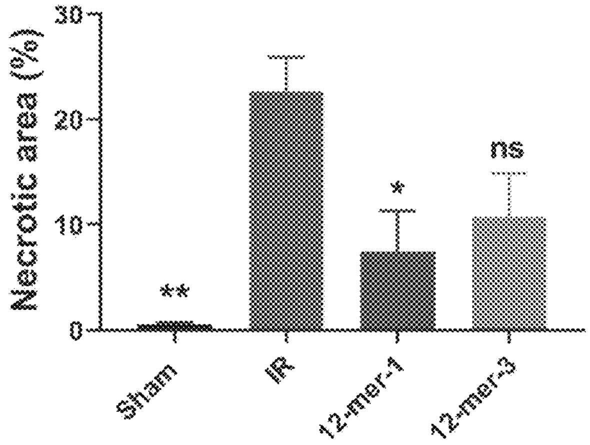
FIGS. 4A through 4E show that 12-mer-1 decreases hepatic necrotic area in ischemia lobe after liver IR.
Figure 4B:
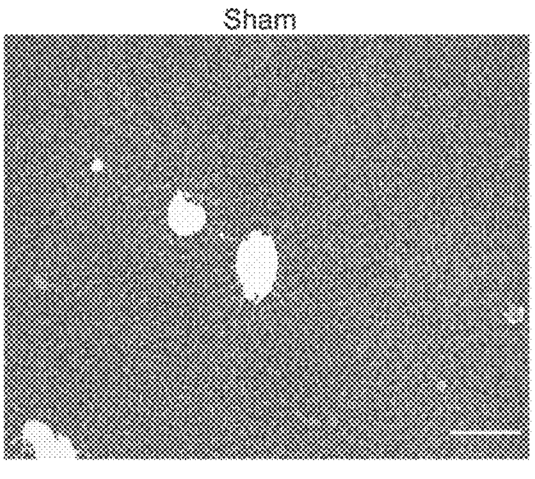
Figure 4C:
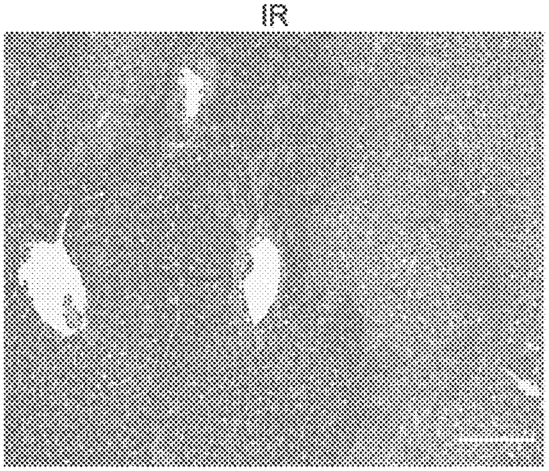
Figure 4D:
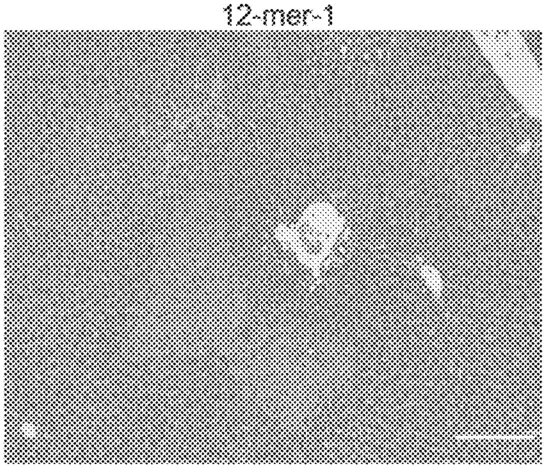
Figure 4E:
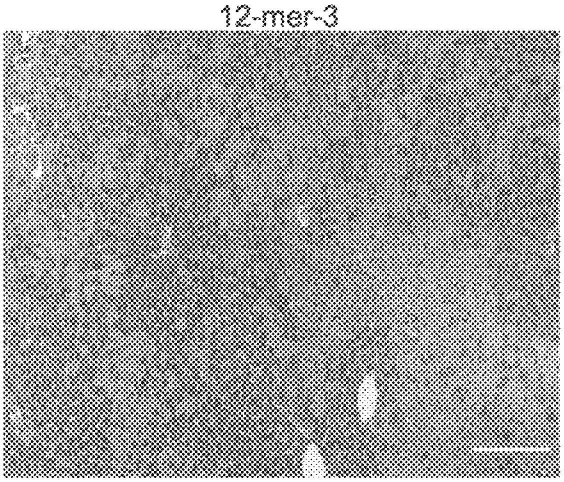

Based on the ability to bind to HMGB1, 12-mer-1 and 12-mer-3 were used in the in vivo model of liver IR. The compounds were administered 30 minutes prior to ischemia. Anticoagulant activity of 12-mer-1 was confirmed in the plasma (FIG. 3A). Although both 12-mer-1 and 12-mer-3 bind to HMGB1, only 12-mer-1 significantly decreased plasma ALT (FIG. 3B; 12-mer-1 vs IR P=0.048, 12-mer-3 vs IR P=0.620). 12-mer-1 also decreased hepatic necrosis in the ischemic liver lobe compared to the IR group (FIG. 4; 12-mer-1 vs IR P=0.0287, 12-mer-3 vs IR P=0.1059). This suggests that 12-mer-1's anticoagulant and anti-inflammatory properties offer protection against liver IR injury.

Example 4

12-mer-1 Decreases Neutrophil Accumulation and MPO to Ischemic Liver

In liver IR, neutrophils are rapidly recruited during the reperfusion phase to the post-ischemic tissue [8]. After neutrophils migrate into the liver, they release cytotoxic compounds including reactive oxygen species and proteases to clear damaged tissue [21]. Neutrophils and their potent cargo are key effectors in sterile inflammation due to the lack of specificity for damage vs healthy tissue. As a result, neutrophil recruitment continues and perpetuates inflammation.

Figure 5A:
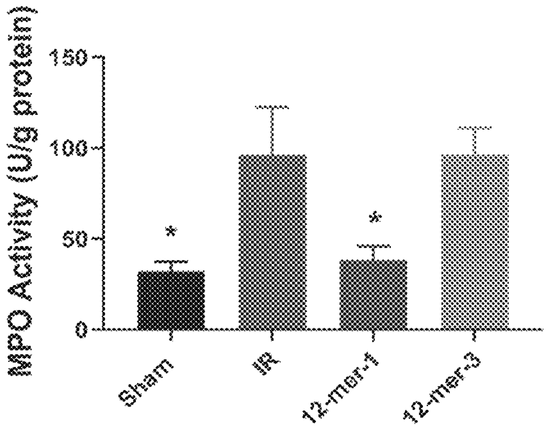
FIG. 5A through FIG. 5F show 12-mer-1 decreases neutrophil accumulation in the ischemia liver.
Figure 5B:
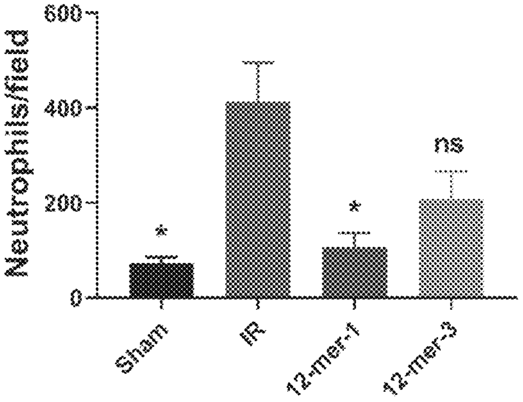
Figure 5C:
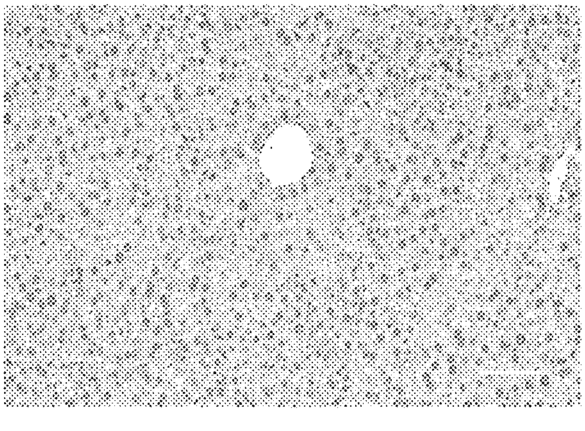
Figure 5D:
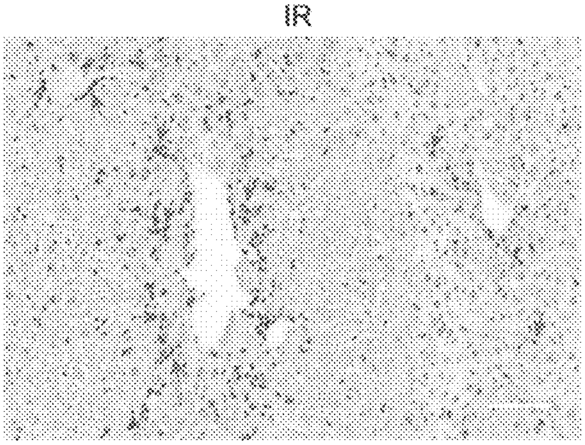
Figure 5E:
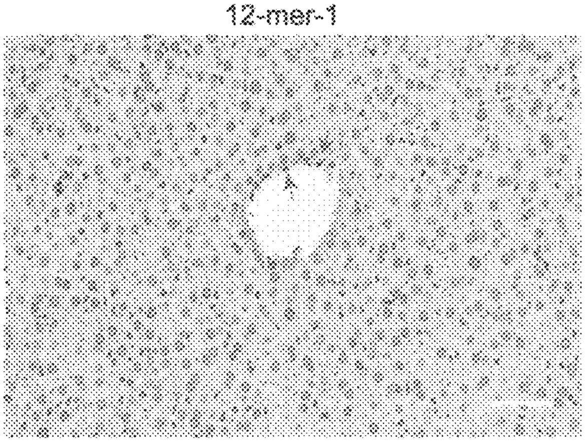
Figure 5F:
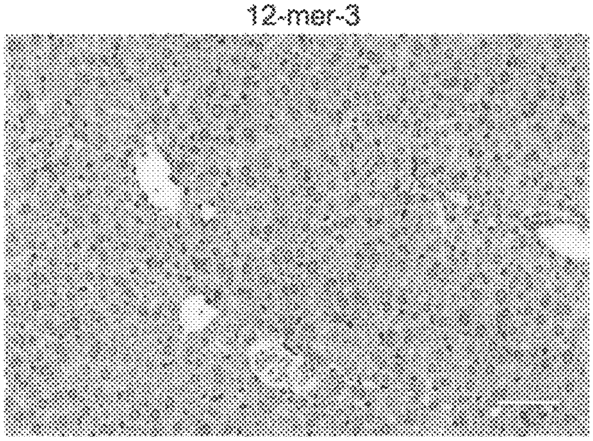

Neutrophil-derived proteases including elastase, MMP-9, cathepsin G, proteinase-3, and myeloperoxidase (MPO) are reportedly implicated in IR induced liver injury [8]. In particular, MPO is highly expressed in neutrophils and serves as a marker of neutrophil accumulation. MPO contributes to oxidative stress in the tissue by reacting with hydrogen peroxide [8]. MPO activity was measured in the ischemic liver lysate (FIG. 5A). 12-mer-1 treatment decreased MPO activity 60% compared to the IR group. In contrast, MPO activity was nearly identical between the 12-mer-3 and IR groups (96.00 vs 96.33 U/g protein, respectively). Furthermore, neutrophil accumulation was measured in the ischemic tissue by immunohistochemistry (FIG. 5B-5F). Similar to the MPO trend, 12-mer-1 decreased neutrophil infiltration whereas 12-mer-3 did not (12-mer-1 vs IRP=0.0142, 12-mer-3 vs IRP=0.0705).

Example 5

Anticoagulation Alone is Not Sufficient for Hepatoprotection

Figure 6B:
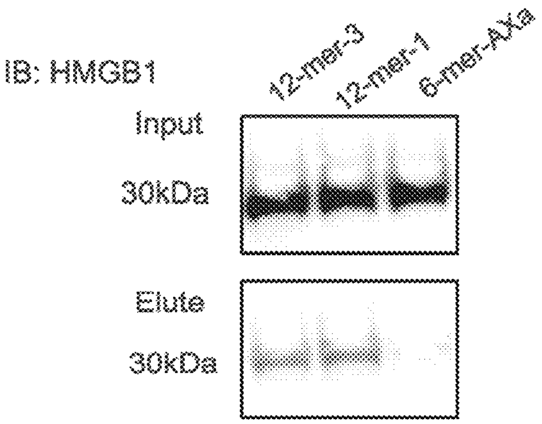
Figure 6C:
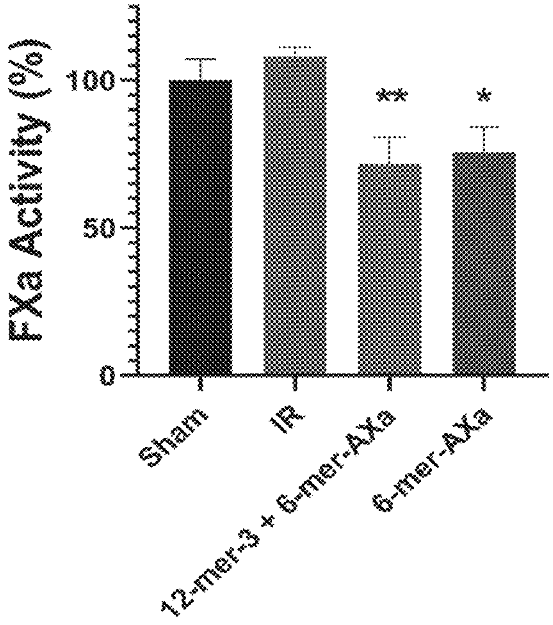
Figure 6D:
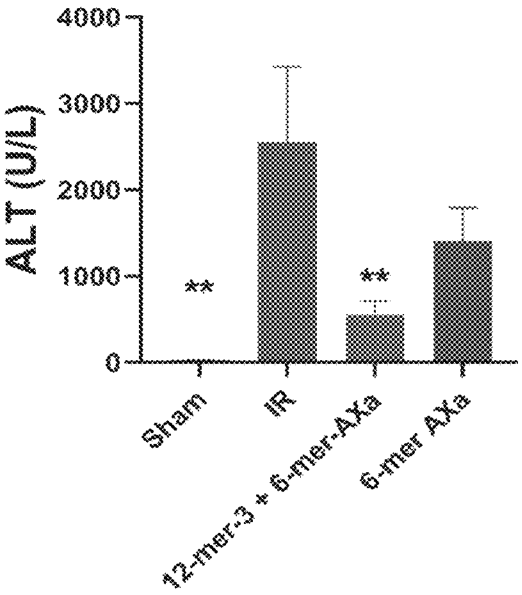

Next, whether hepatoprotection requires anticoagulant activity was investigated. To accomplish this, a 6-mer-AXa oligosaccharide (FIG. 6A) was used. Similar to 12-mer-1, 6-mer-AXa has anticoagulant activity through inhibition of FXa as previously demonstrated [15]. Biotinylated 6-mer-AXa does not pull down HMGB1 from liver lysate (FIG. 6B), and thus serves as a control for anticoagulant activity without HMGB1 binding. To determine if anti-inflammation (e.g., HMGB1 binding) and anticoagulation from a heparan sulfate oligosaccharide are both necessary for hepatoprotection after IR with respect to sizes and sulfation patterns of representative HS compounds, a 6-mer-AXa oligosaccharide alone or in combination with 12-mer-3 was used. Anticoagulant levels are similar between both treatment groups (FIG. 6C), however only the combination treatment of oligosaccharides having HMGB1 binding ability (12-mer-3) and anticoagulant activity (6-mer-AXa) decrease plasma ALT after IR with statistical significance. There was no statistical difference in the concentration of ALT between IR-injured group and 6-mer AXa-treated group. This result demonstrates that both activities, either stemming from one compound with dual activity or a combination of two compounds with separate functions, play a role for hepatoprotection.

Discussion of Examples 1-5

Unlike acetaminophen-induced liver injury, liver IR is reported to involve coagulation disturbances in addition to inflammation and thus described as thromboinflammation [3]. Anticoagulant HS oligosaccharides were ineffective in acetaminophen-induced liver injury [20]; however, since liver IR involves thromboinflammation anticoagulant 12-mer-1 was included in this study to explore how anticoagulant activity and HMGB1 binding effected hepatoprotection in liver IR injury. In doing so, it is demonstrated that synthetic HS oligosaccharides are a therapeutic in another disease model.

In EXAMPLES 1-5, the structure-activity relationship of HS oligosaccharides for HMGB1 binding was explored by screening a panel of 12-mer oligosaccharides with various sulfation patterns. 12-mer-1 and 12-mer-3, which are both highly sulfated oligosaccharides, were the only successful compounds to pull down HMGB1 from liver lysates. However, in vivo it was observed that 12-mer-1 but not 12-mer-3 decreased ALT and necrosis in the ischemic liver lobe. 12-mer-1's anti-inflammatory activity is associated with the ability to bind to HMGB1, decrease tissue MPO, and decrease neutrophil accumulation in ischemic liver lobe. Interestingly, binding the HMGB1 is not sufficient for hepatoprotection as demonstrated by 12-mer-3 in vivo. It was shown that both anticoagulation and anti-inflammatory activity play a role to achieve hepatoprotection by using 6-mer-AXa in combination with 12-mer-3 or alone in the IR model. In this way, anticoagulation in the absence or presence of HMGB1 binding was examined Treatment with 6-mer-AXa alone did not decrease the concentration of ALT that has statistical significance, however the combination treatment did. While it is not desired to be bound by any particular theory of operation, it appears that the 12-mer-1's hepatoprotective effect can be attributed to the dual activities of anticoagulation and anti-inflammation as both mechanisms are essential in the pathophysiology of liver IR.

EXAMPLES 1-5 demonstrate that 2-mer-1 is an active anti-inflammatory agent as well as an anticoagulant. In addition to 12-mer-1's protective mechanism in liver IR, 12-mer-1 also has several favorable drug-like properties. Renal clearance of 12-mer-1 is considered since most liver transplant patients also have impaired renal function [23]. The renal clearance impairment of 12-mer-1 was demonstrated using a kidney IR model [16]. However, 12-mer-1 is amenable to dose adjustments since it is a homogeneous compound with uniform anticoagulant activity and potentially a safe option for renally impaired patients. Bleeding issues have been reported, with 9% of liver transplant recipients on heparin therapy requiring surgical intervention for bleeding complications [24]. LMWH lowers the bleeding risk but it is incompletely reversed by protamine [16]. 12-mer-1 anticoagulant activity is reversible by protamine, which adds an additional benefit to ameliorate bleeding complications [16]. Thus, controlling the dose and having the potential of reversibility by protamine are aspects of 12-mer-1. Additionally, 12-mer-1 displayed no toxicity in a rat model at elevated doses [20]. Therefore, the anti-thromboinflammatory properties, reversibility by protamine, lack of toxicity and ability to precisely control the dose make 12-mer-1 an appealing therapeutic for liver transplant/IR patients. Pharmacokinetic studies investigate the relationship of 12-mer-1 dose and response against liver IR injury.

Heparin and de-sulfated heparin bind to P-selectin [J. Wang; Geng, J., *Thromb Haemost* 90, 7 (2003)], a tethering molecule for neutrophils in most organs and tissues. Interestingly, neutrophil recruitment to the liver has several differences compared to the classical model. For example, there is little evidence for the requirement of selectin or β2-integrin mediated adhesion for neutrophil migration to the liver [8]. Rather, neutrophils are physically trapped in the liver sinusoids where nearly 80% of leukocyte trafficking takes place [S. L. Maas, O. Soehnlein, J. R. Viola, *Frontiers in Immunology* 9, (2018)]. Therefore, without wishing to be bound by any particular theory of operation, it appears that the decrease of neutrophil accumulation after treatment with 12-mer AXa is not due to selectin inhibition.

Dalteparin, a low molecular weight heparin, decreases liver IR injury in rats [22]. Interestingly, in this study they observed no protection when using a selective factor Xa inhibitor, DX9065a, suggesting that dalteparin's protective effect is not solely due to anticoagulation. Dalteparin decreased MPO levels suggesting an effect on neutrophil recruitment. However, due to the incomplete structural characterization of dalteparin, further biochemical analysis is very difficult if not impossible. The chemoenzymatic synthesis technology generates heparin oligosaccharides with or without anticoagulant activity. As heparin is becoming increasingly recognized for its anti-inflammatory properties [25], the presently disclosed subject matter helps to solve the issues of using a heterogenous mixture of oligosaccharides for characterization of biological effects.

The chemoenzymatic synthesis technology generates structurally defined HS oligosaccharides. As heparin is becoming increasingly recognized for its anti-inflammatory properties [25], the presently disclosed subject matter contributes to the transformation of the therapeutic field from one using heterogeneous mixtures of oligosaccharides to a new class of homogeneous, precision-based oligosaccharide therapeutics.

Example 6

HS Oligosaccharides Effect in Liver Ischemia Reperfusion Injury—Description of 18-Mer Results Background:

18-mer with repeating units of N-sulfo glucosamine and 2-O-sulfo iduronic acid was used in the liver ischemia reperfusion (IR) mouse model (FIG. 10). This compound is non-anticoagulant because it is missing particular sulfations required for anticoagulation. As discussed herein above, in some embodiments, if a larger HS compound, such as an 18-mer is used, nonanticoagulant 18-mer displays the protection effect. 18-mer treatment decreases the severity of liver IR injury.

Figure 11A:
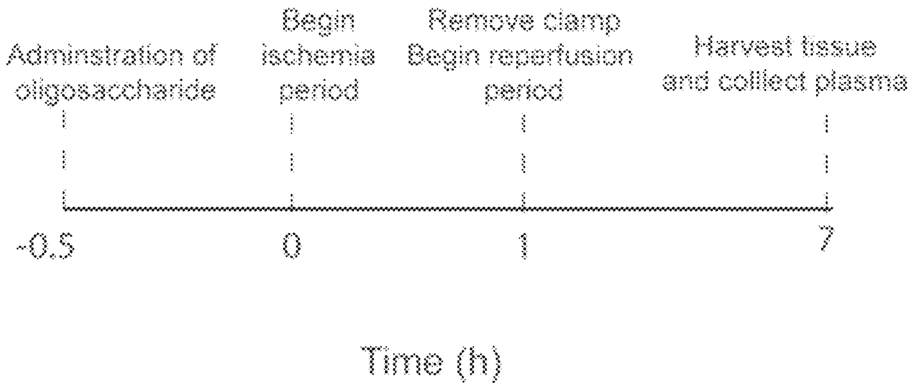
FIGS. 11A to 11F show that the 18-mer of FIG. 10 decreases injury after liver ischemia reperfusion.

IR Procedure:

1 mg/kg of 18-mer or equal volume of sterile saline was administered by subcutaneous injection 30 minutes prior to start of the ischemia phase. Ischemia to 70% of the liver was caused by clamping the portal vein and bile duct for 60 minutes. After the clamp was removed, the reperfusion phase last 6 hours before the animals were sacrificed for collection of liver tissue and blood. For surgical controls, a sham operation was performed such that the animal experienced the same anesthesia, abdominal midline incision, and suturing as the IR mice (FIG. 11A).

Figure 11B:
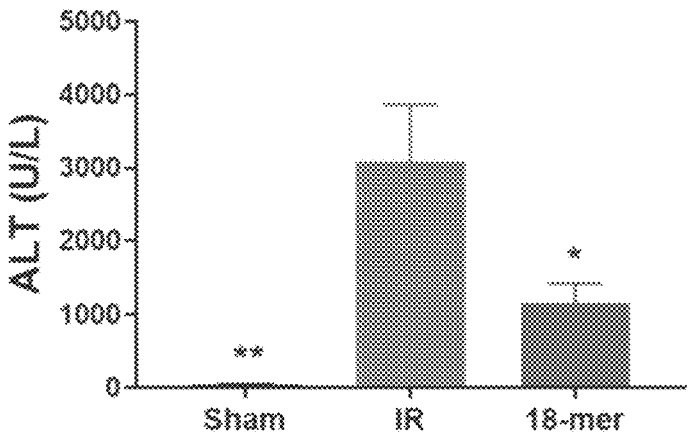
Figure 11C:
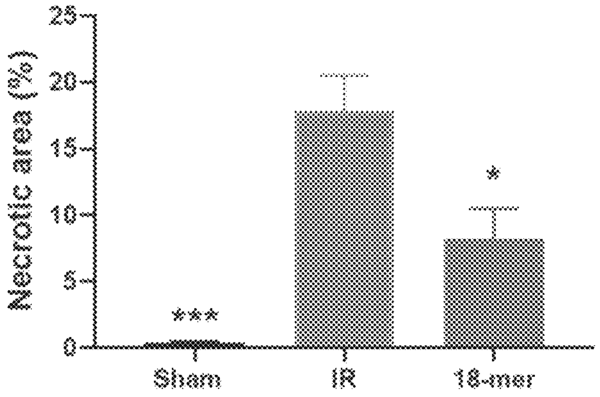
Figure 11D:
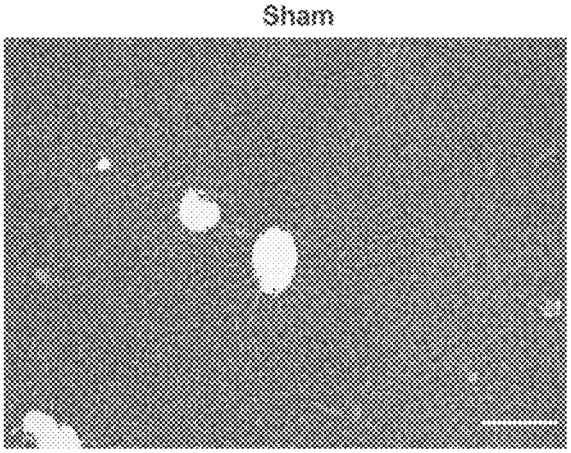
Figure 11E:
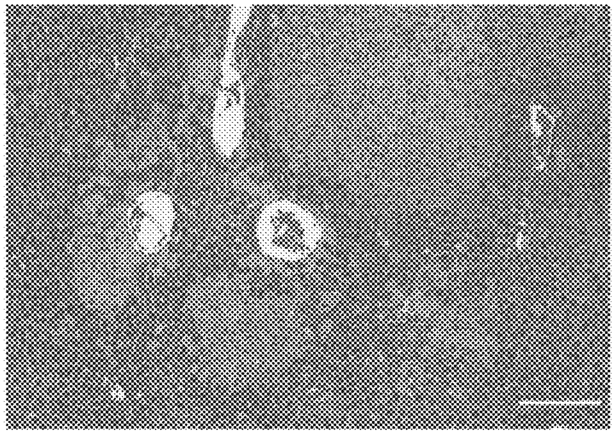
Figure 11F:
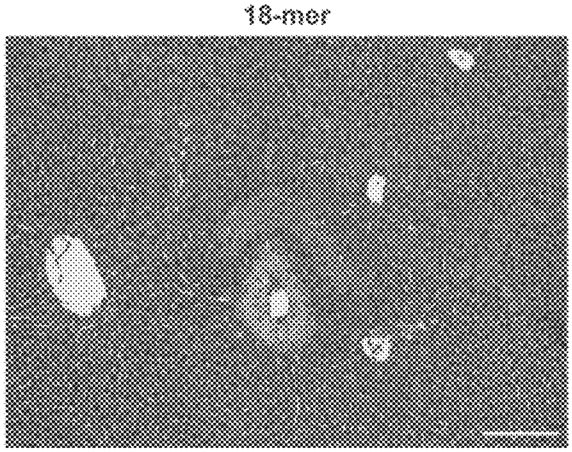

Results:

Treatment with 18-mer decreased liver injury after IR. Plasma alanine aminotransferase (ALT) is a marker of liver injury. 18-mer treatment reduced ALT levels compared to the IR group (FIG. 11B).

For histological evidence of 18-mer's protection, the ischemia liver lobes were stained with H&E for quantification of necrotic area. 18-mer significantly decreased the necrotic area compared to IR (FIGS. 11C-11F).

Figure 12A:
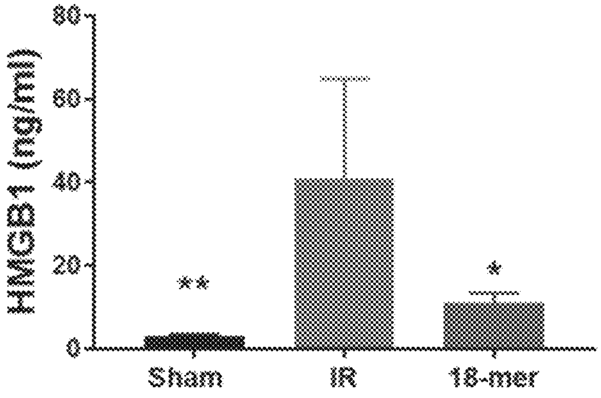
FIGS. 12A-12D are a set of graphs showing that the 18-mer of FIG. 10 decreases inflammatory markers.
Figure 12B:
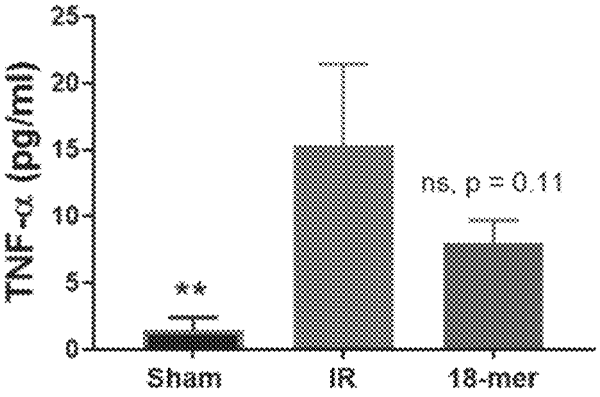
Figure 12C:
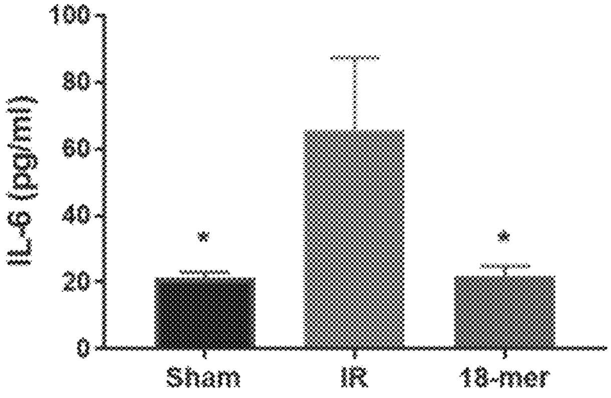
Figure 12D:
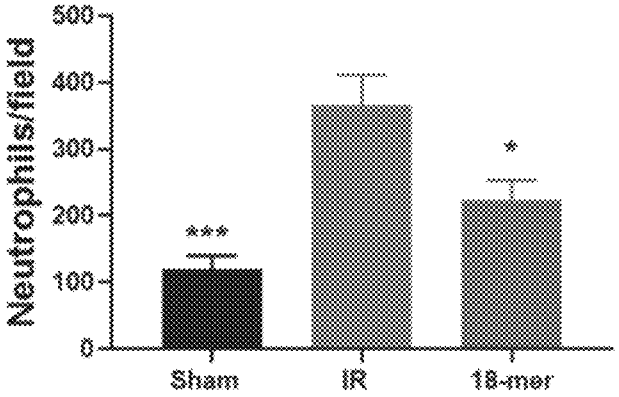

In addition to decreasing necrotic area, 18-mer also had a profound effect on many inflammatory mediators (FIGS. 12A-12D). HMGB1, a known damage associated molecular pattern released after IR, has been implicated in sterile inflammation and propagation of liver injury [A. Tsung et al., *The Journal of experimental medicine* 204, 2913-2923 (2007); J. C. Evankovich, S W; Zhang, R; Cardinal, J; et. al., *J Bio Chem* 285, 9 (2010)]. It was observed that 18-mer decreased plasma HMGB1 (FIG. 12A) and neutrophil infiltration to the ischemic liver lobes (FIG. 12D). Furthermore, other plasma inflammatory markers including IL-6 and TNF-α are decreased with 18-mer treatment.

Conclusion 18-mer decreases liver IR injury possibly by inhibiting HMGB1-mediated neutrophil infiltration and attenuating sterile inflammation. It is likely that other compounds with a similar structure, including 16-mer with the same repeating disaccharide units of N-sulfo glucosamine and 2-O-sulfo iduronic acid, will also be effective in vivo. Additionally, the compounds can be modified to have N-, 6-O-sulfo glucosamine and glucuronic acid residues, which also may be effective in vivo. Also, the compounds can be functionalized with different chemical handles to studying binding in vitro and further elucidate the protective mechanism in liver IR (FIG. 10, $R_2$ position).

REFERENCES

All references listed herein including but not limited to all patents, patent applications and publications thereof, scientific journal articles, and database entries (e.g., GENBANK® database entries and all annotations available therein) are incorporated herein by reference in their entireties to the extent that they supplement, explain, provide a background for, or teach methodology, techniques, and/or compositions employed herein.

1 Konishi, T. & Lentsch, A. B. Hepatic ischemia/reperfusion: mechanisms of tissue injury, repair, and regeneration. *Gene Expr* 17, 277-287, doi:10.3727/105221617X15042750874156 (2017).
2 Man, K. et al. Tolerance of the liver to intermittent pringle maneuver in hepatectomy for liver tumors. *JAMA Surgery* 134, 533-539, doi:10.1001/archsurg.134.5.533 (1999).
3 Jackson, S. D., R; Schoenwaelder, S M. Thromboinflammation: challenges of therapeutically targeting coagulation and other host defense mechanisms. *Blood* 133, 12 (2019).
4 Iba, T., Levy, J. H., Raj, A. & Warkentin, T. E. Advance in the management of sepsis-induced coagulopathy and disseminated intravascular coagulation. *J Clin Med* 8, 728 (2019).
5 Pierce, A. & Pittet, J.-F. Inflammatory response to trauma: implications for coagulation and resuscitation. *Curr Opin Anesthesio* 27, 246-252, doi:10.1097/aco.0000000000000047 (2014).
6 Tsung, A. et al. HMGB1 release induced by liver ischemia involves Toll-like receptor 4 dependent reactive oxygen species production and calcium-mediated signaling. *J Exp Med* 204, 2913-2923, doi:10.1084/jem.20070247 (2007).
7 Huebener, P. et al. The HMGB1/RAGE axis triggers neutrophil-mediated injury amplification following necrosis. *J Clin Invest* 125, 539-550 (2015).
8 Oliveira, T. H. C. d., Marques, P. E., Proost, P. & Teixeira, M. M. M. Neutrophils: a cornerstone of liver ischemia and reperfusion injury. *Lab Invest* 98, 51-62, doi: 10.1038/labinvest.2017.90 (2018).
9 Lu, L. et al. Innate Immune Regulations and Liver Ischemia-Reperfusion Injury. *Transplantation* 100, 2601-2610 (2016).
10 Gama, C. et al. Sulfation patterns of glycosaminoglycans encode molecular recognition and activity. *Nat Chem Biol* 2, 467-473 (2006).
11 Feltracco, P. et al. Perioperative thrombotic complications in liver transplantation. *World J Gastroenterol* 21, 8004-8013, doi:10.3748/wjg.v21.i26.8004 (2015).
12 Jaimes, F. et al. Unfractioned heparin for treatment of sepsis: A randomized clinical trial (The HETRASE Study) *. *Crit Care Med* 37, 1185-1196, doi:10.1097/CCM.0b013e31819c06bc (2009).
13 Liu, J. & Linhardt, R. J. Chemoenzymatic synthesis of heparan sulfate and heparin. *Nat Prod Rep* 31, 1676-1685 (2014).
14 Xu, Y. et al. Chemoenzymatic synthesis of homogeneous ultra-low molecular weight heparin. *Science* 334, 498-501 (2011).
15 Xu, Y. et al. Homogeneous low-molecular-weight heparins with reversible anticoagulant activity. *Nat Chem Biol* 10, 248-250, doi: 10.1038/nchembio. 1459 (2014).
16 Xu, Y. et al. Synthetic oligosaccharides can replace animal-sourced low-molecular weight heparins. *Sci Transl Med* 9, eaan5954, doi:10.1126/scitranslmed.aan5954 (2017).
17 Tsung, A. et al. The nuclear factor HMGB1 mediates hepatic injury after murine liver ischemia-reperfusion. *J Exp Med* 201, 1135-1143, doi:10.1084/jem.20042614 (2005).
18 Teng, Y. H.-F., Aquino, R. S. & Park, P. W. Molecular functions of syndecan-1 in disease. *Matrix Biol* 31, 3-16, doi: 10.1016/j.matbio.2011.10.001 (2012).
19 Yamamoto, T. & Tajima, Y. HMGB1 is a promising therapeutic target for acute liver failure. *Expert Rev Gatroenterol Hepatol* 11, 673-682 (2017).
20 Arnold, K. et al. Design of anti-inflammatory heparan sulfate to protect against acetaminophen-induced acute liver failure. *Sci Transl Med* 12, eaav8075, doi: 10.1126/scitranslmed.aav8075 (2020).
21 Kubes, P. & Mehal, W. Z. Sterile inflammation in the liver. *Gastroenterology* 143, 1158-1172, doi:https://doi.org/10.1053/j.gastro.2012.09.008 (2012).
22 Naoaki Harada, M. K. O., M D; Mitsuhiro Uchiba, MD. Dalteparin, a low molecular weight heparin, attenuates inflammatory responses and reduces ischemia-reperfusion-induced liver injury in rats. *Crit Care Med* 34, 8 (2006).
23 Weber, M. L., Ibrahim, H. N. & Lake, J. R. Renal dysfunction in liver transplant recipients: Evaluation of the critical issues. *Liver Transplant* 18, 1290-1301, doi: 10.1002/1t.23522 (2012).
24 Kaneko, J. et al. Coagulation and fibrinolytic profiles and appropriate use of heparin after living-donor liver transplantation. *Clin Transplant* 19, 804-809, doi:10.1111/j.1399-0012.2005.00425.x (2005).
25 Oduah, E. I., Linhardt, R. J. & Sharfstein, S. T. Heparin: Past, present, and future. *Pharmaceuticals* (Basel) 9, 38, doi:10.3390/ph9030038 (2016).
26 U.S. Pat. No. 9,951,149, issued Apr. 24, 2018.
27 PCT International Patent Application Serial No. PCT/US2018/059152, published as WO 2019/090203, published May 9, 2019.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method of treating a subject suffering from liver ischemia reperfusion (I/R) injury or at risk of suffering liver I/R injury, the method comprising administering to the subject one or more synthetic heparan sulfate (HS) compounds, wherein:

(i) the one or more synthetic HS compounds comprise a synthetic HS compound having the following structure:

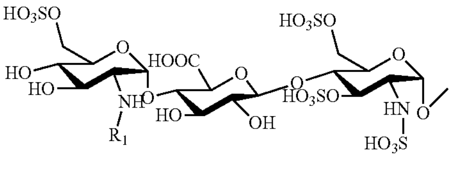

-continued

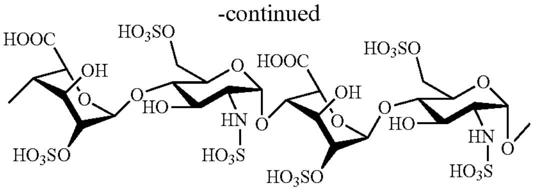

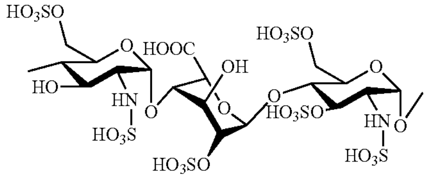

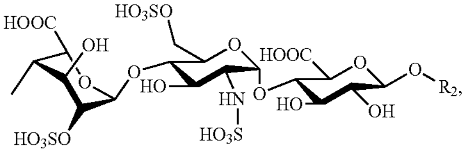

wherein $R_1$ is —$SO_3H$ or —$COCH_3$ and $R_2$ is —H, alkyl, aryl, substituted alkyl, substituted aryl, or a functional handle;

(ii) the one or more synthetic HS compounds comprise one synthetic HS compound having the structure GlcNS6S-GlcA-GlcNS6S-IdoA2S-GlcNS6S-IdoA2S-GlcNS6S-IdoA2S-GlcNS6S-IdoA2S-GlcNS6S-GlcA-pNP and comprise one synthetic HS compound having the structure:

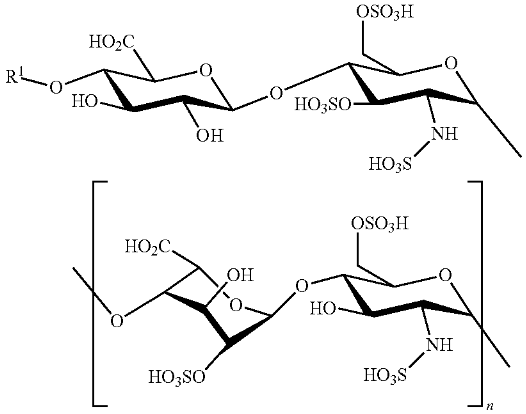

-continued

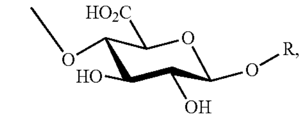

wherein R is —H, alkyl, aryl, substituted alkyl, substituted aryl, or a functional handle; and wherein $R^1$=H and n=1; $R^1$=H and n=2; $R^1$=GlcNS- or GlcNS6S- and n=1; or where $R^1$=GlcA-GlcNS- or GlcA-GlcNS6S- and n=1; or (iii) the one or more synthetic HS compounds comprise a synthetic HS compound having the structure:

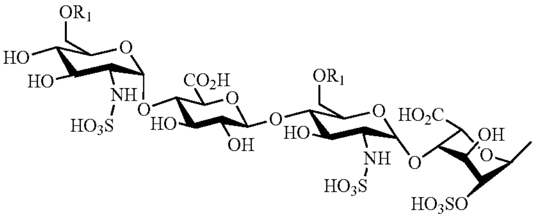

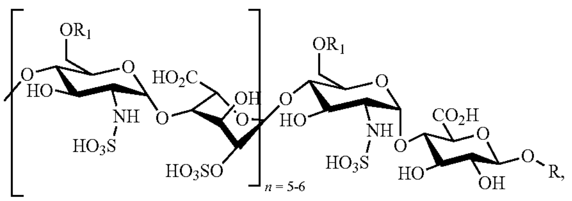

wherein $R_1$ is —$SO_3H$ or —H and $R_2$ is —H, alkyl, aryl, substituted alkyl, substituted aryl, or a functional handle.

2. The method of claim 1, wherein the one or more synthetic HS compounds comprises a synthetic HS compound having the following structure:

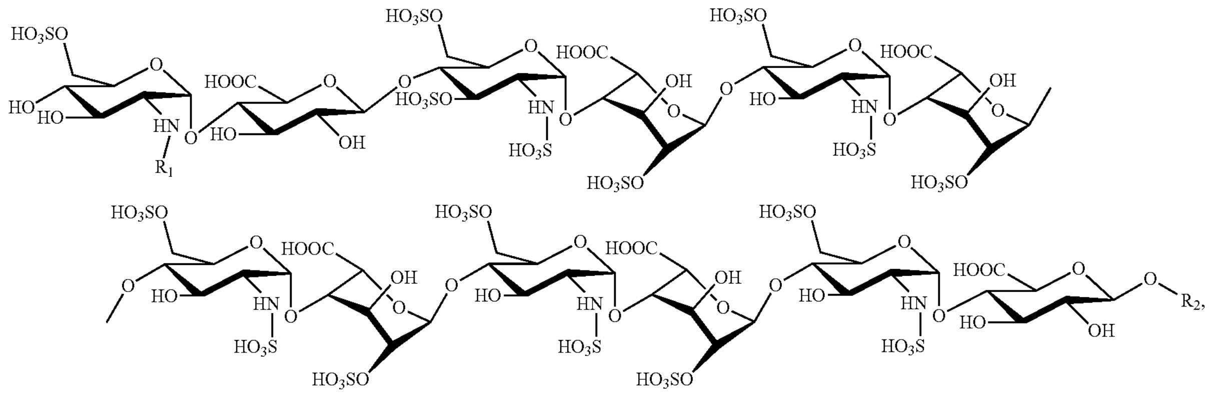

wherein $R_1$ is —$SO_3H$ and $R_2$ —H, alkyl, aryl, substituted alkyl, substituted aryl, or a functional handle.

3. The method of claim 1, wherein the one or more HS compounds comprises a synthetic HS compound having the following formula:

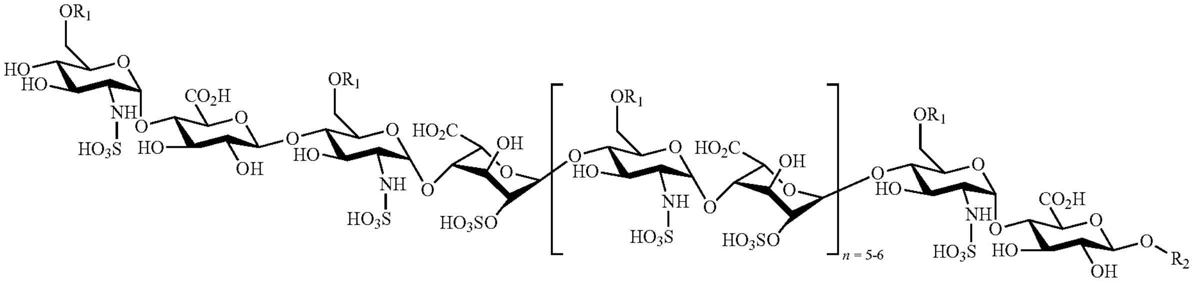

wherein $R_1$ is —$SO_3H$ or —H and $R_2$ is —H, alkyl, aryl, substituted alkyl, substituted aryl, or a functional handle.

4. The method of claim 1, wherein the one or more synthetic HS compounds comprises a synthetic HS compound having the following formula:

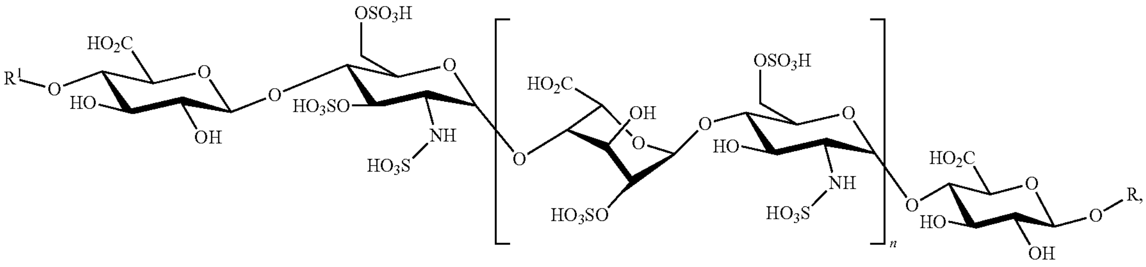

wherein R is —H, alkyl, aryl, substituted alkyl, substituted aryl, or a functional handle; and wherein R1=H and n=1;

R1=H and n=2;

$R^1$=GlcNS- or GlcNS6S and n=1; or

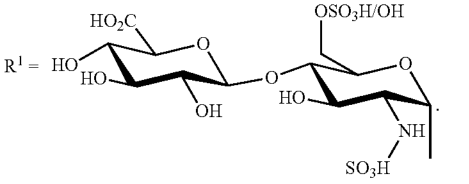

n = 1

$R^1$=GlcA-GlcNS or GlcA-GlcNS6S and n=1.

5. The method of claim 1, wherein the one or more synthetic HS compounds comprises a synthetic HS compound having the following formula:

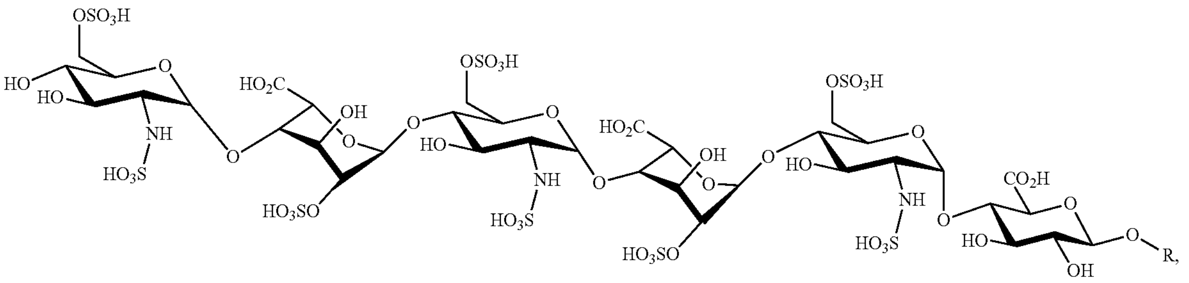

wherein R is —H, alkyl, aryl, substituted alkyl, substituted aryl, or a functional handle.

6. The method of claim 1, wherein at least one of the one or more synthetic HS compounds binds HMGB1.

7. The method of claim 1, wherein the subject in need of treatment is a mammalian subject.

8. The method of claim 1, wherein the one or more synthetic HS compounds is administered as part of a pharmaceutical composition.

9. The method of claim 8, wherein the pharmaceutical composition comprises a synthetic HS compound and a pharmaceutically acceptable carrier or adjuvant for administration of the synthetic HS compound.

10. The method of claim 1, wherein the administering comprises administering two or more synthetic HS compounds, optionally wherein the two or more synthetic HS compounds are administered separately but at the same time, optionally wherein the two or more synthetic HS compounds are administered at different times, optionally wherein the two or more synthetic HS compounds are administered in a single composition.

* * * * *